US010519125B2

(12) United States Patent
Marion et al.

(10) Patent No.: US 10,519,125 B2
(45) Date of Patent: Dec. 31, 2019

(54) FLAVAGLINE DERIVATIVES

(71) Applicant: PIERRE FABRE MEDICAMENT, Boulogne-Billancourt (FR)

(72) Inventors: Frédéric Marion, Toulouse (FR); El Bachir Kaloun, Roquettes (FR); Frédéric Lieby-Muller, Portet-sur-Garonne (FR); Michel Perez, Castres (FR); Jean-Philippe Annereau, Toulouse (FR); Laurent Creancier, Portet sur Garonne (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/829,630

(22) Filed: Dec. 1, 2017

(65) Prior Publication Data

US 2018/0086729 A1 Mar. 29, 2018

Related U.S. Application Data

(63) Continuation of application No. 15/323,650, filed as application No. PCT/EP2015/065294 on Jul. 6, 2015, now Pat. No. 10,047,064.

(30) Foreign Application Priority Data

Jul. 4, 2014 (FR) ...................................... 14 56474

(51) Int. Cl.
*C07D 307/93* (2006.01)
*C07D 413/04* (2006.01)
*C07D 491/048* (2006.01)
*C07D 498/04* (2006.01)
*C07D 405/04* (2006.01)
*A61P 35/00* (2006.01)

(52) U.S. Cl.
CPC ............ *C07D 307/93* (2013.01); *A61P 35/00* (2018.01); *C07D 405/04* (2013.01); *C07D 413/04* (2013.01); *C07D 491/048* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 6,710,075 B2 * | 3/2004 | Meurer-Grimes | ... C07D 307/93 514/452 |
| 8,137,509 B2 | 3/2012 | Porco, Jr. et al. | |
| 8,404,088 B2 | 3/2013 | Porco, Jr. et al. | |
| 2009/0018113 A1 | 1/2009 | Diedrichs et al. | |

FOREIGN PATENT DOCUMENTS

| | | |
|---|---|---|
| EP | 2189453 A1 | 5/2010 |
| JP | 2007-538031 A | 12/2007 |
| JP | 2012-510964 A | 5/2012 |
| WO | WO 2010/063471 A1 | 6/2010 |

OTHER PUBLICATIONS

Huang et al. "Bortezonnib Suppresses the Growth of Leukemia Cells with Notch1 Overexpression in vivo and in vitro". Cancer Chemother Pharmacol. 2012; 70:801-809. (Year: 2012).*
Wellcome Trust Sanger Institute [Online]. "The Measure of Man". [Retrieved Feb. 5, 2013]. Retrieved from the Internet: <URL: http://www.sanger.ac.uk/about/press/2002/021205.html.> Published Dec. 5, 2002. (Year: 2002).*
Ohse et al. "Cyclopentabenzofuran Lignan Protein Synthesis Inhibitors from Aglaia odorata". J Nat Prod. 1996; 59:650-652. (Year: 1996).*
Wang et al. "Cytotoxic Cyclopenta[b]benzofuran Derivatives from the Stem Bark of Aglaia formosana". Planta Med. 2001; 67:555-557. (Year: 2001).*
Li-Weber M. "Molecular Mechanisms and Anti-Cancer Aspects of the Medicinal Phytochemicals Rocaglamides (=Flavaglines)". International Journal of Cancer. 2015; 137:1791-1799. (Published Online Jun. 11, 2014). (Year: 2014).*
Adams et al., "Total Synthesis of the Potent Anticancer Aglaia Metabolites (−)-Silvestrol and (−)-Episilvestrol and the Active Analogue (−)-4′-Desmethoxyepisilvestrol," Journal of the American Chemical Society, vol. 131, No. 4, 2009 (published on Web Jan. 13, 2009), pp. 1607-1616.
Cencic et al., "Antitumor Activity and Mechanism of Action of the Cyclopenta[b]benzofuran, Silvestrol," PLoS One, vol. 4, Iss. 4, Apr. 29, 2009, pp. 1-14.
Corbett et al., "Preclinical anticancer activity of cryptophycin-8," Journal of Experimental Therapeutics & Oncology, vol. 1, 1996, pp. 95-108.
Desaubry et al. (2010): STN International, HCAPLUS database (Columbus, OH), Accession No. 2010: 679927.
Gerard et al, "Enantioselective Photocycloaddition Mediated by Chiral Brønsted Acids: Asymmetric Synthesis of the Rocaglamides," Journal of the American Chemical Society, vol. 128, No. 24, 2006 (published on Web May 25, 2006), pp. 7754-7755.
Gerard et al. (2007): STN International, HCAPLUS database (Columbus, OH), Accession No. 2007: 1226249.
Hausott et al., "Flavaglines: A Group of Efficient Growth Inhibitors Block Cell Cycle Progression and Induce Apoptosis in Colorectal Cancer Cells," International Journal of Cancer, vol. 109, 2004, pp. 933-940.

(Continued)

*Primary Examiner* — Leslie A. Royds Draper
(74) *Attorney, Agent, or Firm* — Birch, Stewart, Kolasch & Birch, LLP

(57) ABSTRACT

The invention relates to compounds of the following general formula (I) in the form of one of the enantiomers thereof or a mixture of the enantiomers thereof, and the pharmaceutically acceptable salts and/or solvates thereof, especially for the use thereof as a medicament, more specifically in cancer treatment. The invention also relates to pharmaceutical compositions containing same and to the methods for the production thereof.

11 Claims, No Drawings

(56) References Cited

OTHER PUBLICATIONS

Hawkins et al., "Simplified Silvestrol Analogues with Potent Cytotoxic Activity," ChemMedChem, vol. 9, 2014. pp. 1556-1566.

International Search Report (Form PCT/ISA/210) issued in PCT/EP2015/065294, dated Aug. 24, 2015, together with an English translation.

Kim et al., "Potential of Cyclopenta[b]benzofurans from *Aglaia* Species in Cancer Chemotherapy," Anti-Cancer Agents in Medicinal Chemistry, vol. 6, No. 4, 2006, pp. 319-345.

Kraus et al., "A Synthetic Approach to Rocaglamide via Reductive Cyclization of δ-Keto Nitriles," Journal of Organic Chemistry, vol. 54, No. 1, 1989, pp. 77-83.

Li et al., "Aqueous Phosphoric Acid as a Mild Reagent for Deprotection of tert-Butyl Carbamates, Esters, and Ethers," Journal of Organic Chemistry, vol. 71, No. 24, 2006 (published on Web Oct. 28, 2006), pp. 9045-9050.

Liu et al. (2012): STN International, HCAPLUS database (Columbus, OH), Accession No. 2012: 1430066.

Liu et al., "Synthetic Silvestrol Analogues as Potent and Selective Protein Synthesis Inhibitors," Journal of Medicinal Chemistry, vol. 55, 2012 (published Oct. 1, 2012), pp. 8859-8878.

Ohse et al., "Cyclopentabenzofuran Lignan Protein Synthesis Inhibitors from Aglaia odorata," Journal of Natural Products, vol. 59, No. 7, 1996 (abstract published in advance, ACS Abstracts, Jun. 15, 1996), pp. 650-652.

Ribeiro et al., "Recent advances in the biology and chemistry of the flavaglines," Bioorganic & Medicinal Chemistry, vol. 20, 2012 (available online Oct. 20, 2011), pp. 1857-1864.

Rodrigo et al. (2011): STN International, HCAPLUS database (Columbus, OH), Accession No. 2011: 1555591.

Gerard et al., "Enantioselective Synthesis of the Complex Rocaglate (−)-Silvestrol", Angew. Chem., Itn. Ed., vol. 46, 2007, pp. 7831-7834 (67 pages total).

Lajkiewicz et al., "Remodeling Natural Products: Chemistry and Serine Hydrolase Activity of a Rocaglate-Derived β-Lactone", Journal of the American Chemical Society, vol. 136, Jan. 21, 2014, pp. 2659-2664 (7 pages total).

Wang et al., "Studies on Synthesis and Biological Activity of Oxidative Aglafolin", Journal of Heterocyclic Chemistry, vol. 51, Mar. 25, 2014, pp. 1430-1434 (6 pages total).

\* cited by examiner

FLAVAGLINE DERIVATIVES

CROSS-REFERENCE TO RELATED APPLICATIONS

This application is a Divisional of copending application Ser. No. 15/323,650, filed on Jan. 3, 2017, which is the National Phase under 35 U.S.C. § 371 of International Application No. PCT/EP2015/065294, filed on Jul. 6, 2015, which claims the benefit under 35 U.S.C. § 119(a) to patent application Ser. No. 1456474, filed in France on Jul. 4, 2014, all of this are hereby expressly incorporated by reference into the present application.

The present invention has as an object novel flavagline derivatives, processes for manufacturing same, pharmaceutical compositions containing same and the use of same as a drug, particularly in the treatment of cancer.

The flavaglines are a family of natural products comprising a unique cyclopenta[b]benzofuran skeleton, whose members include silvestrol and rocaglamide.

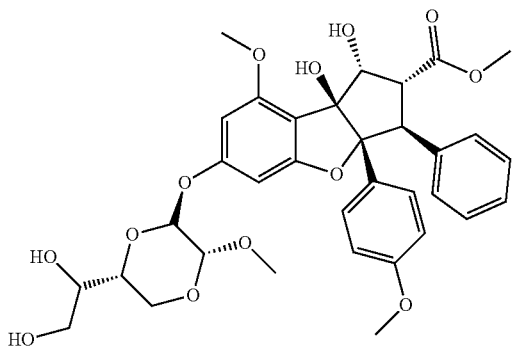
silvestrol

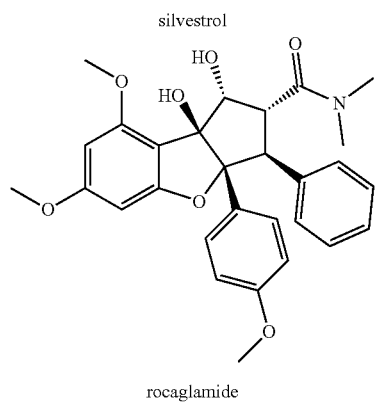
rocaglamide

This family has numerous biological properties, in particular including antiproliferative activities (Hausott et al. Int. J. Cancer: 109, 933-940 (2004)). This ability to inhibit the growth of cancer cell lines has been linked for certain of these members, such as silvestrol, to the inhibition of protein synthesis through inactivation of the helicase eIF4A (Cencic et al. PloS ONE 2009, 4(4): e5223). These properties make the flavagline family interesting for a potential application in the treatment of hyperproliferative diseases, such as cancer for example. Despite several efforts (Ribeiro et al. Bioorg. Med. Chem. 20 (2012) 1857-1864; Liu et al. J. Med. Chem. 2012, 55, 8859-8878), heretofore no natural product or flavagline derivative has shown sufficient potential to lead to an use as a drug.

The present invention thus relates to novel flavagline derivatives having advantageous antiproliferative activities for application as an anticancer treatment in particular. The inventors have thus shown that, unexpectedly, substantial modifications of the cyclopenta[b]benzofuran skeleton, or sets of modifications, lead to compounds which are more powerful than silvestrol and which have higher antitumor activity.

The present invention thus has as an object a compound of the following general formula (I):

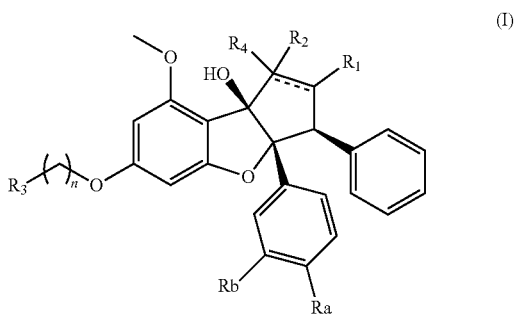

(I)

in the form of one of the enantiomers thereof or a mixture of the enantiomers thereof such as a racemic mixture,
or a pharmaceutically acceptable salt and/or solvate thereof,
wherein:
$\rule[0.5ex]{2em}{0.4pt}$ represents a single bond or a double bond,
n represents an integer between 1 and 10,
$R_1$ represents $CO_2R_{10}$, $CONH_2$, $NR_{11}R_{12}$, $NR_{13}COR_{14}$, $NR_{15}CONR_{16}R_{17}$, $NR_{18}CSNR_{19}R_{20}$, $NR_{21}SO_2R_{22}$, $NR_{23}CO_2R_{24}$ or an optionally substituted heteroaryl preferentially selected from optionally substituted triazoles and oxadiazoles,
$R_2$ represents OH, or
$R_1$ and $R_2$ together form, with the carbon atoms which bear them, an optionally substituted heterocycle, preferentially selected from optionally substituted pyrimidine, pyrazole, pyrazolone, oxazoline, isoxazoline, oxazalanone, oxazalanethione, morpholinone and oxazepane rings, the optionally substituted heterocycle not being:

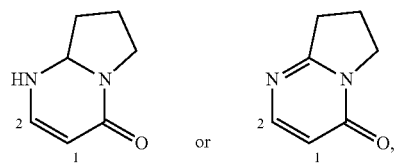 [SMILES: O=C1C=CNC2CCCN12 ; "or" ; O=c1ccnc2n1CCC2]

carbon 1 designating the carbon atom bearing the group $R_1$ and carbon 2 designating the carbon atom bearing the group $R_2$,
$R_3$ represents H, $OR_{25}$, $CHOHCH_2OH$, $CHO$, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_w NR_{33}(CH_2)_x)_y(CH_2)_zR_{34}$, $ONR_{84}R_{85}$, optionally substituted aryl or optionally substituted heteroaryl,
$R_4$ is absent when $\rule[0.5ex]{2em}{0.4pt}$ represents a double bond and $R_4$ represents H or OH when $\rule[0.5ex]{2em}{0.4pt}$ represents a single bond,
$R_{10}$ to $R_{30}$, $R_{32}$, $R_{33}$, $R_{38}$ and $R_{39}$ represent, independently of each other, H or a $(C_1-C_6)$alkyl, aryl, aryl-$(C_1-C_6)$alkyl or $(C_1-C_6)$alkyl-aryl group, said group being optionally substituted by one or more groups selected from $(C_1-C_6)$alkyl, $OR_{35}$ and $NR_{36}R_{37}$, or $R_{11}$ and $R_{12}$, or $R_{16}$ and $R_{17}$, or $R_{19}$ and $R_{20}$, or $R_{26}$ and $R_{27}$, or $R_{29}$ and $R_{30}$, together form, with the nitrogen atom which bears them, an optionally substituted nitrogen-containing heterocycle, $R_{31}$ and $R_{34}$ represent, independently of each other, H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, said group being optionally substituted by one or more groups selected from $(C_1-C_6)$alkyl, $OR_{35}$ and $NR_{36}R_{37}$, $R_{35}$ to $R_{37}$ and $R_{84}$ to $R_{87}$ represent, independently of each other, H or a $(C_1-C_6)$alkyl, aryl or aryl-$(C_1-C_6)$alkyl group, Ra represents a halogen atom (for example Br or Cl), CN or a $(C_1-C_6)$alkoxy group (such as methoxy), Rb represents H or a $(C_1-C_6)$alkoxy group (such as methoxy), or Ra and Rb together form an —OCH$_2$O— chain, and m, p, r, q, w, x, y, z represent, independently of each other, an integer between 1 and 4, provided that when $R_1$ represents $CO_2R_{10}$ or $CONH_2$ and n=1 or 2 then $R_3$ represents $OR_{25}$, $CHOHCH_2OH$, CHO, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$ or $ONR_{84}R_{85}$ with $R_{25}\neq H$.

Preferably, when $R_1$ represents $CO_2R_{10}$ or $CONH_2$, then $R_3$ represents $OR_{25}$, $CHOHCH_2OH$, CHO, $N_3$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$ or $ONR_{84}R_{85}$ with $R_{25}\neq H$.

In the present invention, by "pharmaceutically acceptable" is meant that which is useful in the preparation of a pharmaceutical composition which is generally safe, non-toxic and neither biologically nor otherwise undesirable and which is acceptable for veterinary as well as human pharmaceutical use.

By "pharmaceutically acceptable salt and/or solvate" of a compound is meant a salt and/or solvate which is pharmaceutically acceptable, as defined herein, and which has the desired pharmacological activity of the parent compound.

Pharmaceutically acceptable salts include in particular:

(1) pharmaceutically acceptable acid addition salts formed with pharmaceutically acceptable inorganic acids such as hydrochloric acid, hydrobromic acid, phosphoric acid, sulfuric acid and the like; or formed with pharmaceutically acceptable organic acids such as acetic acid, trifluoroacetic acid, propionic acid, succinic acid, fumaric acid, malic acid, tartaric acid, citric acid, ascorbic acid, maleic acid, glutamic acid, benzoic acid, salicylic acid, toluenesulfonic acid, methanesulfonic acid, stearic acid, lactic acid and the like, and (2) pharmaceutically acceptable base addition salts formed when an acid proton present in the parent compound is either replaced by a metal ion, for example an alkali metal ion, an alkaline-earth metal ion or an aluminum ion; or is coordinated with a pharmaceutically acceptable organic base such as lysine, arginine and the like; or with a pharmaceutically acceptable inorganic base such as soda, potassium hydroxide, calcium hydroxide and the like.

These salts may be prepared from the compounds according to the invention containing a basic or acidic function and the corresponding acids or bases according to conventional chemical methods.

Acceptable solvates for pharmaceutical use of the compounds according to the present invention include conventional solvates such as those formed, during the last step of the process for preparing the compounds according to the invention, with the reaction solvent(s). By way of example, mention may be made of solvates formed with water (commonly called hydrates) or with ethanol.

By "enantiomers" is meant compounds which are non-superimposable mirror images of each other.

A mixture containing equal amounts of two individual enantiomeric forms of opposite chirality is referred to as a "racemic mixture".

By "$(C_1-C_6)$alkyl" is meant, within the meaning of the present invention, a saturated, linear or branched hydrocarbon chain comprising 1 to 6 carbon atoms. By way of example, mention may be made of methyl, ethyl, propyl, isopropyl, butyl, isobutyl, secbutyl, tert-butyl, pentyl or hexyl groups.

By "$(C_1-C_6)$alkoxy" group is meant, within the meaning of the present invention, a $(C_1-C_6)$alkyl group as defined above, linked to the remainder of the molecule via an oxygen atom. By way of example, mention may be made of methoxy, ethoxy, propoxy, isopropoxy, butoxy or tert-butoxy groups. It will be in particular a methoxy group.

By "aryl" is meant, within the meaning of the present invention, an aromatic hydrocarbon group comprising preferably 6 to 10 carbon atoms and which may comprise one or two fused rings. By way of example, mention may be made of a phenyl or a naphthyl. Advantageously it is phenyl.

By "heteroaryl" is meant, within the meaning of the present invention, an aromatic group comprising one or more, particularly 1 or 2, fused hydrocarbon rings, wherein one or more carbon atoms, advantageously 1 to 4 and even more advantageously 1 or 2, are each replaced by a heteroatom selected from sulfur, nitrogen and oxygen atoms. Exemplary heteroaryl groups include furyl, thienyl, pyrrolyl, pyridinyl, pyrimidinyl, pyrazolyl, imidazolyl, oxazolyl, isoxazolyl, oxadiazolyl, triazolyl, tetrazolyl and indyl groups.

By "heterocycle" is meant, within the meaning of the present invention, a saturated, unsaturated or aromatic hydrocarbon group comprising 1 or 2 fused rings and wherein one or more, advantageously 1 to 4, even more advantageously 1 or 2, of the carbon atoms are each replaced by a heteroatom selected from oxygen, nitrogen and sulfur. Advantageously, the heterocycle will comprise 5 to 10 carbon atoms and heteroatoms. By way of example, mention may be made of furan, pyrrole, thiophene, thiazole, triazoles, isothiazole, oxadiazole, imidazole, oxazole, isoxazole, pyrazole, pyridine, pyrimidine, piperazine, piperidine, pyrazolone, oxazoline, isoxazoline, oxazalanone, oxazalanethione, morpholinone, oxazepane, quinazoline, quinoline, quinoxaline, benzofuran, benzothiophene, indoline, indolizine, benzothiazole, benzothiophene, benzopyran, benzoxazole, benzo[1,3]dioxole, benzisoxazole, benzimidazole, chromane, chromene, dihydrobenzofuran, dihydrobenzothiophene, dihydroisoxazole, isoquinoline, dihydrobenzo[1,4]dioxine, imidazo[1,2-a]pyridine, furo[2,3-c]pyridine, 2,3-dihydro-1H-indene, [1,3]dioxolo[4,5-c]pyridine, pyrrolo[1,2-c]pyrimidine, pyrrolo[1,2-a]pyrimidine, tetrahydronaphthalene and benzo[b][1,4]oxazine rings.

By "nitrogen-containing heterocycle" is meant, within the meaning of the present invention, a heterocycle as defined above comprising at least one nitrogen atom, preferably saturated. It may be in particular a ring with 5 or 6 members optionally comprising, in addition to the nitrogen atom, another heteroatom selected preferably from oxygen and nitrogen. It will be in particular a piperidine, piperazine, morpholine or pyrrolidine group.

By "aryl-$(C_1-C_6)$alkyl" is meant, within the meaning of the present invention, an aryl group as defined above linked to the remainder of the molecule via an alkyl group as defined above and comprising 1 to 6, advantageously 1 to 4, preferably 1 or 2, carbon atoms. It will be in particular a benzyl or phenethyl group.

By "$(C_1-C_6)$alkyl-aryl" is meant, within the meaning of the present invention, a $(C_1-C_6)$alkyl group as defined above, linked to the remainder of the molecule via an aryl group as defined above. By way of example, mention may be made of the tolyl group ($CH_3Ph$).

By "optionally substituted" is meant, within the meaning of the present invention, that the group in question is optionally substituted by one or more substituents which may be selected in particular from a halogen atom, an $SO_2$, CN, $NO_2$, $OR_{95}$, $SR_{96}$, $NR_{97}R_{98}$, $(C_1-C_6)$alkyl, $(C_1-C_6)$alkyl-aryl, aryl-$(C_1-C_6)$alkyl, heterocycle or aryl group, with $R_{95}$ to $R_{98}$ representing, independently of each other, H or a $(C_1-C_6)$alkyl, aryl, aryl-$(C_1-C_6)$alkyl or $(C_1-C_6)$alkyl-aryl group, said group being optionally substituted by one or more groups selected from $(C_1-C_6)$alkyl, $OR_{99}$ and $NR_{100}R_{101}$, $R_{99}$ to $R_{101}$ representing, independently of each other, H or a $(C_1-C_6)$alkyl group, or $R_{97}$ and $R_{98}$ together forming, with the nitrogen atom which bears them, an optionally substituted nitrogen-containing heterocycle.

Preferably, $R_{95}$ to $R_{98}$ represent, independently of each other, H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{97}$ and $R_{98}$ together form, with the nitrogen atom which bears them, a nitrogen-containing heterocycle optionally substituted by a $(C_1-C_6)$alkyl group, the heterocycle being in particular a heterocycle with 5 or 6 members optionally comprising, in addition to the nitrogen atom, another heteroatom selected from oxygen and nitrogen, such as a piperidine, piperazine, morpholine or pyrrolidine group.

By "halogen atom" is meant, within the meaning of the present invention, fluorine, chlorine, bromine and iodine atoms. It will be in particular a chlorine or bromine atom.

By "polyamine" is meant, within the meaning of the present invention, a linear hydrocarbon chain comprising 4 to 15 carbon atoms, of which at least two of these carbon atoms are replaced by nitrogen atoms, wherein two nitrogen atoms may not be located in adjacent positions. Said polyamine may have in particular the following formula:

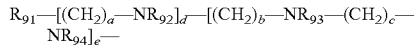

$$R_{91}-[(CH_2)_a-NR_{92}]_d-[(CH_2)_b-NR_{93}-(CH_2)_c-NR_{94}]_e-$$

with a, b and c representing, independently of each other, an integer between 1 and 5 and d and e each representing 0, 1 or 2 but not representing 0 at the same time and d not representing 1 when e=0 and with $R_{91}$ to $R_{94}$ representing H or a $(C_1-C_6)$alkyl, aryl, $(C_1-C_6)$alkyl-aryl or aryl-$(C_1-C_6)$alkyl group.

Advantageously, n is between 1 and 4.

According to a particular embodiment, Ra=$(C_1-C_6)$alkoxy such as OMe and Rb=H.

A particularly valued class of compounds corresponds to compounds of formula (I) wherein:

=== represents a single bond, $R_1$ represents $CO_2R_{10}$ or $CONH_2$, particularly $CO_2R_{10}$, $R_3$ represents $OR_{25}$, $CHOHCH_2OH$, CHO, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$, $ONR_{84}R_{85}$, optionally substituted aryl or optionally substituted heteroaryl, particularly $OR_{25}$, $CHOHCH_2OH$, CHO, $N_3$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$, $ONR_{84}R_{85}$, optionally substituted aryl or optionally substituted heteroaryl, and $R_4$ represents H.

In this case, $R_{10}$ represents advantageously H or a $(C_1-C_6)$alkyl group such as methyl.

Preferably, $R_3$ will represent $OR_{25}$, $CHOHCH_2OH$, CHO, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$ or $ONR_{84}R_{85}$; particularly $OR_{25}$, $CHOHCH_2OH$, CHO, $N_3$, $NR_{26}R_{27}$, $CO_2R_{28}$, $CONR_{29}R_{30}$, $(NR_{32}(CH_2)_wNR_{33}(CH_2)_x)_y(CH_2)_zR_{34}$ or $ONR_{84}R_{85}$; advantageously $NR_{26}R_{27}$, $CONR_{29}R_{30}$, $(NR_{32}(CH_2)_wNR_{33}(CH_2)_x)_y(CH_2)_zR_{34}$ or $ONR_{84}R_{85}$ with $R_{25}$ to $R_{34}$, $R_{38}$, $R_{39}$, $R_{84}$ and $R_{85}$ as defined above and particularly with:

$R_{25}$ being as defined above and representing advantageously H or a $(C_1-C_6)$alkyl group, particularly H, $R_{26}$ and $R_{27}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{26}$ and $R_{27}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, particularly $R_{26}$ and $R_{27}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, $R_{28}$, $R_{32}$, $R_{33}$, $R_{38}$ and $R_{39}$ representing, independently of each other, H or a $(C_1-C_6)$alkyl, aryl, aryl-$(C_1-C_6)$alkyl or $(C_1-C_6)$alkyl-aryl group, preferably H or a $(C_1-C_6)$alkyl group, $R_{29}$ and $R_{30}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{29}$ and $R_{30}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, and $R_{31}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $OR_{35}$ or a $(C_1-C_6)$alkyl group, $R_{34}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $NR_{36}R_{37}$ or a $(C_1-C_6)$alkyl group, and $R_{35}$ to $R_{37}$ and $R_{84}$ to $R_{87}$ being as defined above and representing advantageously H or a $(C_1-C_6)$alkyl group.

$R_3$ may represent also advantageously $OR_{25}$, $CHOHCH_2OH$, CHO, $N_3$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$ or $ONR_{84}R_{85}$; particularly $OR_{25}$, $CHOHCH_2OH$, CHO, $N_3$, $CO_2R_{28}$, $CONR_{29}R_{30}$, $(NR_{32}$ $(CH_2)_wNR_{33}(CH_2)_x)_y(CH_2)_zR_{34}$ or $ONR_{84}R_{85}$; advantageously $CONR_{29}R_{30}$, $(NR_{32}(CH_2)_wNR_{33}(CH_2)_x)_y(CH_2)_zR_{34}$ or $ONR_{84}R_{85}$ with $R_{25}$ to $R_{34}$, $R_{38}$, $R_{39}$, $R_{84}$ and $R_{85}$ as defined above and particularly with:

$R_{25}$ being as defined above and representing advantageously H or a $(C_1-C_6)$alkyl group, particularly H, $R_{28}$, $R_{32}$, $R_{33}$, $R_{38}$ and $R_{39}$ representing, independently of each other, H or a $(C_1-C_6)$alkyl, aryl, aryl-$(C_1-C_6)$alkyl or $(C_1-C_6)$alkyl-aryl group, preferably H or a $(C_1-C_6)$ alkyl group, $R_{29}$ and $R_{30}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{29}$ and $R_{30}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, and $R_{31}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $OR_{35}$ or a $(C_1-C_6)$alkyl group, $R_{34}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $NR_{36}R_{37}$ or a $(C_1-C_6)$alkyl group, and $R_{35}$ to $R_{37}$ and $R_{84}$ to $R_{87}$ being as defined above and representing advantageously H or a $(C_1-C_6)$alkyl group.

Another particularly valued class of compounds corresponds to compounds of formula (I) wherein:

=== represents a single bond, $R_1$ represents $NR_{11}R_{12}$, $NR_{13}COR_{14}$, $NR_{15}CONR_{16}R_{17}$, $NR_{18}CSNR_{19}R_{20}$ or $NR_{21}SO_2R_{22}$, and $R_4$ represents H.

Preferably $R_3$ is as defined above, preferably $R_3$ represents H.

$R_{11}$ to $R_{22}$ are as defined above and preferably:

$R_{11}$ to $R_{22}$ represent, independently of each other, H or a $(C_1-C_6)$alkyl group, optionally substituted by one or more groups selected from $(C_1-C_6)$alkyl, $OR_{35}$ and $NR_{36}R_{37}$, preferably selected from $OR_{35}$ and $NR_{36}R_{37}$, such as $NR_{36}R_{37}$, or $R_{11}$ and $R_{12}$, or $R_{16}$ and $R_{17}$, or $R_{19}$ and $R_{20}$, together form, with the nitrogen atom which bears them, a nitrogen-containing heterocycle optionally substituted by a $(C_1-C_6)$ alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group.

Preferably, $R_{11}$ to $R_{22}$ represent, independently of each other, H or a $(C_1-C_6)$alkyl group, optionally substituted by one or more groups selected from $(C_1-C_6)$alkyl, $OR_{35}$ and $NR_{36}R_{37}$, preferably selected from $OR_{35}$ and $NR_{36}R_{37}$, such as $NR_{36}R_{37}$.

Another particularly valued class of compounds corresponds to compounds of formula (I) wherein:

=== represents a single bond, $R_1$ represents

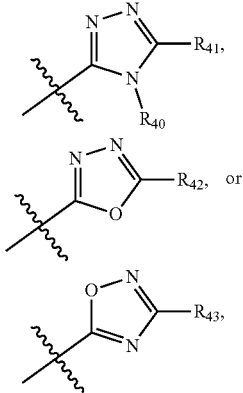

$R_4$ represents H, $R_{40}$ represents H or a $(C_1-C_6)$alkyl, aryl or aryl-$(C_1-C_6)$ alkyl group, particularly H or a $(C_1-C_6)$alkyl group, advantageously H, $R_{41}$ to $R_{43}$ represent, independently of each other, H or a $(C_1-C_6)$alkyl, aryl, aryl-$(C_1-C_6)$alkyl, $OR_{44}$, $SR_{45}$ or $NR_{46}R_{47}$ group, particularly H or a $(C_1-C_6)$alkyl, $OR_{44}$, $SR_{45}$ or $NR_{46}R_{47}$ group, particularly a $(C_1-C_6)$alkyl, $OR_{44}$, $SR_{45}$ or $NR_{46}R_{47}$ group, $R_{44}$ to $R_{47}$ represent, independently of each other, H or a $(C_1-C_6)$alkyl, aryl or aryl-$(C_1-C_6)$alkyl group, said group being optionally substituted by one or more groups selected from $(C_1-C_6)$alkyl, $OR_{48}$, $NR_{49}R_{50}$ and polyamines, particularly selected from $(C_1-C_6)$alkyl, $OR_{48}$ and $NR_{49}R_{50}$, particularly selected from $OR_{48}$ and $NR_{49}R_{50}$, such as $NR_{49}R_{50}$, or $R_{46}$ and $R_{47}$ together form, with the nitrogen atom which bears them, a nitrogen-containing heterocycle optionally substituted by a $(C_1-C_6)$alkyl group, and $R_{48}$ to $R_{50}$ represent, independently of each other, H or a $(C_1-C_6)$alkyl, aryl or aryl-$(C_1-C_6)$alkyl group.

The nitrogen-containing heterocycle will be advantageously a heterocycle having 5 or 6 members optionally comprising, in addition to the nitrogen atom, another heteroatom selected from oxygen and nitrogen, such as a piperidine, piperazine, morpholine or pyrrolidine group.

Preferably, $R_{44}$ to $R_{47}$ represent, independently of each other, H or a $(C_1-C_6)$alkyl group optionally substituted by one or more groups selected from $(C_1—C_6)$alkyl, $OR_{48}$, $NR_{49}R_{50}$ and polyamines, particularly selected from $(C_1-C_6)$alkyl, $OR_{48}$ and $NR_{49}R_{50}$, particularly selected from $OR_{48}$ and $NR_{49}R_{50}$, such as $NR_{49}R_{50}$.

Advantageously, $R_3$ will represent H, $OR_{25}$, $CHOHCH_2OH$, $CHO$, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$ or $ONR_{84}R_{85}$; particularly H, $OR_{25}$, $CHOHCH_2OH$, $CHO$, $N_3$, $NR_{26}R_{27}$, $CO_2R_{28}$, $CONR_{29}R_{30}$ or $(NR_{32}(CH_2)_wNR_{33}(CH_2)_x)_y(CH_2)_zR_{34}$, with $R_{25}$ to $R_{34}$, $R_{38}$, $R_{39}$, $R_{84}$ and $R_{85}$ as defined above and particularly with:

$R_{25}$ representing H or a $(C_1-C_6)$alkyl group, particularly H, $R_{26}$ and $R_{27}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{26}$ and $R_{27}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, $R_{28}$, $R_{32}$, $R_{33}$, $R_{38}$ and $R_{39}$ representing, independently of each other, H or a $(C_1$-$C_6)$alkyl, aryl, aryl-$(C_1$-$C_6)$alkyl or $(C_1$-$C_6)$alkyl-aryl group, preferably H or a $(C_1$-$C_6)$ alkyl group, $R_{29}$ and $R_{30}$ representing H or a $(C_1$-$C_6)$alkyl, aryl, aryl-$(C_1$-$C_6)$alkyl or $(C_1$-$C_6)$alkyl-aryl group, preferably H or a $(C_1$-$C_6)$alkyl group, or $R_{29}$ and $R_{30}$ together form, with the nitrogen atom which bears them, a nitrogen-containing heterocycle optionally substituted by a $(C_1$-$C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, and $R_{31}$ representing H, $OR_{35}$, $NR_{36}R_{37}$, $ONR_{86}R_{87}$ or a $(C_1$-$C_6)$alkyl, aryl, aryl-$(C_1$-$C_6)$alkyl or $(C_1$-$C_6)$alkyl-aryl group, preferably H, $OR_{35}$ or a $(C_1$-$C_6)$alkyl group, $R_{34}$ representing H, $OR_{35}$, $NR_{36}R_{37}$, $ONR_{86}R_{87}$ or a $(C_1$-$C_6)$alkyl, aryl, aryl-$(C_1$-$C_6)$alkyl or $(C_1$-$C_6)$alkyl-aryl group, preferably H, $NR_{36}R_{37}$ or a $(C_1$-$C_6)$alkyl group, and $R_{35}$ to $R_{37}$ and $R_{84}$ to $R_{87}$ being as defined above and representing advantageously H or a $(C_1$-$C_6)$alkyl group.

Another particularly valued class of compounds corresponds to compounds of

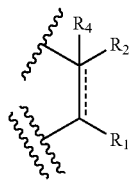

formula (I) wherein the moiety

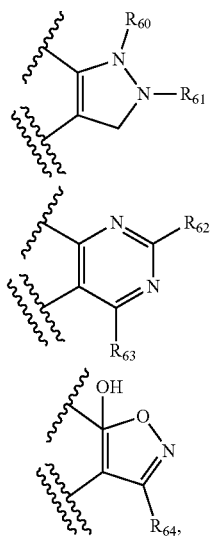

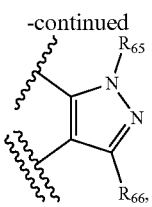

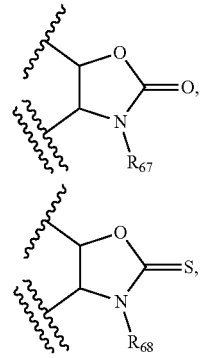

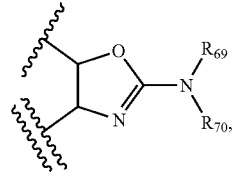

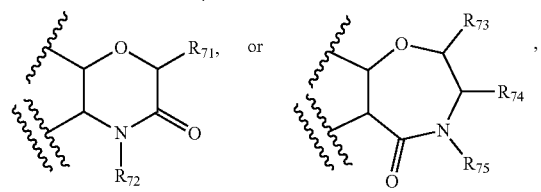

represents:

with:

$R_{60}$, $R_{61}$, $R_{65}$, $R_{67}$, $R_{68}$, $R_{72}$ and $R_{75}$ representing, independently of each other, H or a $(C_1$-$C_6)$alkyl, aryl or aryl-$(C_1$-$C_6)$alkyl group, particularly H or a $(C_1$-$C_6)$ alkyl group, preferably H, $R_{69}$ and $R_{70}$ representing, independently of each other, H or a $(C_1$-$C_6)$alkyl, aryl or aryl-$(C_1$-$C_6)$alkyl group, or together forming, with the nitrogen atom which bears them, a nitrogen-containing heterocycle optionally substituted by a $(C_1$-$C_6)$alkyl group, $R_{62}$, $R_{63}$, $R_{64}$, $R_{66}$, $R_{71}$, $R_{73}$ and $R_{74}$ representing, independently of each other, H or a $(C_1$-$C_6)$alkyl, aryl, aryl-$(C_1$-$C_6)$alkyl, $OR_{76}$, $SR_{77}$ or $NR_{78}R_{79}$ group, and $R_{76}$ to $R_{79}$ representing, independently of each other, H or a $(C_1$-$C_6)$alkyl, aryl, aryl-$(C_1$-$C_6)$alkyl or CN group, or $R_{78}$ and $R_{79}$ together forming, with the nitrogen atom which bears them, a nitrogen-containing heterocycle optionally substituted by a $(C_1$-$C_6)$alkyl group.

The nitrogen-containing heterocycle will be advantageously a heterocycle having 5 or 6 members optionally comprising, in addition to the nitrogen atom, another heteroatom selected from oxygen and nitrogen, such as a piperidine, piperazine, morpholine or pyrrolidine group.

Preferably $R_{69}$ and $R_{70}$ represent, independently of each other, H or a $(C_1$-$C_6)$alkyl, aryl or aryl-$(C_1$-$C_6)$alkyl group, particularly H or a $(C_1$-$C_6)$alkyl group, particularly H.

Advantageously, $R_{62}$, $R_{63}$, $R_{64}$ and $R_{66}$ represent, independently of each other, H or a $(C_1$-$C_6)$alkyl, $OR_{76}$, $SR_{77}$ or $NR_{78}R_{79}$ group, particularly an $OR_{76}$, $SR_{77}$ or $NR_{78}R_{79}$ group.

Advantageously, $R_{71}$, $R_{73}$ and $R_{74}$ represent, independently of each other, H or a $(C_1-C_6)$alkyl, aryl or aryl-$(C_1-C_6)$alkyl group, particularly H or a $(C_1-C_6)$alkyl group, particularly H.

$R_{76}$ to $R_{79}$ represent in particular, independently of each other, a $(C_1-C_6)$alkyl, aryl, aryl-$(C_1-C_6)$alkyl or CN group, particularly a $(C_1-C_6)$alkyl, aryl or aryl-$(C_1-C_6)$alkyl group.

According to a particular embodiment, when === represents a single bond, then $R_1$ and $R_2$ are located on the same side of the cyclopentane ring to which they are linked, and preferably on the side opposite to the OH, phenyl and m-Rb-p-Ra-phenyl groups also linked to this cyclopentane ring.

Advantageously, $R_3$ will represent H, $OR_{25}$, $CHOHCH_2OH$, CHO, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, or $(NR_{32}(CH_2)_wNR_{33}(CH_2)_x)_y(CH_2)_zR_{34}$ or $ONR_{84}R_{85}$; particularly H, $OR_{25}$, $CHOHCH_2OH$, CHO, $N_3$, $NR_{26}R_{27}$, $CO_2R_{28}$, $CONR_{29}R_{30}$ or $(NR_{32}(CH_2)_wNR_{33}(CH_2)_x)_y(CH_2)_zR_{34}$, with $R_{25}$ to $R_{34}$, $R_{38}$, $R_{39}$, $R_{84}$ and $R_{85}$ as defined above and particularly with:

- $R_{25}$ representing H or a $(C_1-C_6)$alkyl group, particularly H,
- $R_{26}$ and $R_{27}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{26}$ and $R_{27}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group,
- $R_{28}$, $R_{32}$, $R_{33}$, $R_{38}$ and $R_{39}$ representing, independently of each other, H or a $(C_1-C_6)$alkyl, aryl, aryl-$(C_1-C_6)$alkyl or $(C_1-C_6)$alkyl-aryl group, preferably H or a $(C_1-C_6)$ alkyl group,
- $R_{29}$ and $R_{30}$ representing H or a $(C_1-C_6)$alkyl, aryl, aryl-$(C_1-C_6)$alkyl or $(C_1-C_6)$alkyl-aryl group, preferably H or a $(C_1-C_6)$alkyl group, or $R_{29}$ and $R_{30}$ together form, with the nitrogen atom which bears them, a nitrogen-containing heterocycle optionally substituted by a $(C_1-C_6)$alkyl group, the heterocycle being in particular a heterocycle having 5 or 6 members optionally comprising, in addition to the nitrogen atom, another heteroatom selected from oxygen and nitrogen, such as a piperidine, piperazine, morpholine or pyrrolidine group, and
- $R_{31}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $OR_{35}$ or a $(C_1-C_6)$alkyl group,
- $R_{34}$ representing H, $OR_{35}$, $NR_{36}R_{37}$, $ONR_{86}R_{87}$ or a $(C_1-C_6)$alkyl, aryl, aryl-$(C_1-C_6)$alkyl or $(C_1-C_6)$alkyl-aryl group, preferably H, $NR_{36}R_{37}$ or a $(C_1-C_6)$alkyl group, and
- $R_{35}$ to $R_{37}$ and $R_{84}$ to $R_{87}$ being as defined above and representing advantageously H or a $(C_1-C_6)$alkyl group.

The compounds of the present invention may be selected from compounds 1 to 55 exemplified below, in the form of one of the enantiomers thereof or a mixture of the enantiomers thereof such as a racemic mixture, and pharmaceutically acceptable salts and/or solvates thereof.

The present invention also has as an object a compound according to the invention of formula (I) as defined above, for use as a drug, in particular intended for the treatment of cancer.

The present invention also relates to the use of a compound of formula (I) as defined above, for the manufacture of a drug, in particular intended for the treatment of cancer.

The present invention also relates to a method for treating cancer, comprising administering to a person in need thereof an effective dose of a compound of formula (I) as defined above.

The cancer may be more particularly in this case colon cancer, breast cancer, kidney cancer, liver cancer, pancreatic cancer, prostate cancer, glioblastoma, non-small cell lung cancer, neuroblastoma, inflammatory myofibroblastic tumor, diffuse large B-cell lymphoma or anaplastic large-cell lymphoma.

The present invention also relates to a pharmaceutical composition comprising at least one compound of formula (I) as defined above, and at least one pharmaceutically acceptable excipient.

The pharmaceutical compositions according to the invention may be formulated particularly for oral administration or for administration by injection, said compositions being intended for mammals, including humans.

The active ingredient may be administered in unit forms of administration, mixed with conventional pharmaceutical carriers, to animals or humans. The compounds of the invention as active ingredients may be used at doses between 0.01 mg and 1000 mg per day, given in a single dose once per day or administered in several doses throughout the day, for example twice per day in equal doses. The administered dose per day is advantageously between 5 mg and 500 mg, even more advantageously between 10 mg and 200 mg. It may be necessary to use doses beyond these ranges, which would be self-evident to the person skilled in the art.

The pharmaceutical compositions according to the invention may further comprise at least one other active ingredient, such as an anticancer agent.

The present invention also has as an object a pharmaceutical composition comprising:

(i) at least one compound of formula (I) as defined above, and (ii) at least one other active ingredient, such as an anticancer agent, as a combination product, for simultaneous, separate or sequential use.

The present invention also relates to a pharmaceutical composition as defined above for use as a drug, particularly intended for the treatment of cancer.

The present invention also relates to a method for treating cancer, comprising administering to a person in need thereof an effective dose of a pharmaceutical composition as defined above.

The present invention also has as an object processes for preparing compounds of formula (I) according to the invention.

A first process for preparing a compound of formula (I) according to the invention wherein $R_3$=H comprises reacting a compound of the following formula (II):

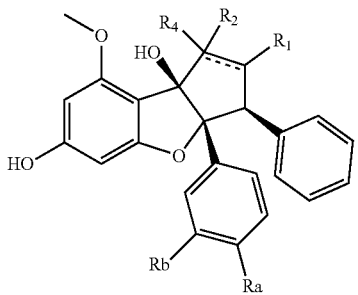

(II)

wherein Ra, Rb, $R_1$, $R_2$ and $R_4$ are as defined above,
with an alcohol of formula H—$(CH_2)_n$OH, wherein n is as defined above, under Mitsunobu conditions.

Such a reaction may be carried out in the presence of DEAD (diethyl azodicarboxylate) or DMEAD (bis(2-methoxyethyl) azodicarboxylate) and PPh$_3$.

A second process for preparing a compound of formula (I) according to the invention wherein $R_3$=$N_3$, $NR_{38}COR_{39}$ or $NR_{26}R_{27}$ comprises:

(a1) to obtain a compound of formula (I) wherein $R_3$=$N_3$, reacting a compound of the following formula (III):

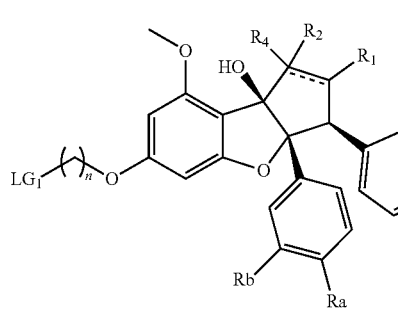

(III)

wherein Ra, Rb, $R_1$, $R_2$, $R_4$ and n are as defined above and
  LG$_1$ represents a leaving group such as a halogen atom or an activated hydroxyl function,
with an azide of formula MN$_3$, M representing an alkali metal or an SiRR'R" group with R, R' and R" each representing, independently of each other, a ($C_1$-$C_6$) alkyl or aryl group,
(b1) to obtain a compound of formula (I) wherein $R_3$=$NH_2$, reducing the azide function of a compound of formula (I) wherein $R_3$=$N_3$ optionally obtained according to step (a1),
(c1) to obtain a compound of formula (I) wherein $R_3$=$NR_{38}COR_{39}$ or $NR_{26}R_{27}$ and at least one of $R_{26}$ and $R_{27}$ does not represent a hydrogen atom, substituting a compound of formula (I) wherein $R_3$=$NH_2$ optionally obtained according to step (b1).

Step (a1):
By "leaving group" is meant, within the meaning of the present invention, a chemical group which can be easily displaced by a nucleophile during a nucleophilic substitution reaction, the nucleophile being in the present case an azide. Such a leaving group may be more particularly a halogen atom such as a chlorine or bromine atom or a sulfonate. The sulfonate may be particularly an —OSO$_2$—R$_{90}$ group with R$_{90}$ representing a ($C_1$-$C_6$)alkyl, aryl, aryl-($C_1$-$C_6$)alkyl or ($C_1$-$C_6$)alkyl-aryl group, said group being optionally substituted by one or more halogen atoms such as fluorine atoms. The sulfonate may be in particular a mesylate (—OS(O$_2$)—CH$_3$), a triflate (—OS(O)$_2$—CF$_3$) or a tosylate (—OS(O)$_2$-(p-Me-C$_6$H$_4$)).

The leaving group may also be an alcohol (OH) function activated in the presence of, for example, DPPA (diphenylphosphine azide) and DBU (1,8-diazabicyclo[5.4.0]undec-7-ene).

The alkali metal may be in particular Na, K or Li.

R, R' and R" each will represent in particular, independently of each other, a methyl or phenyl group, in particular methyl.

M will represent in particular Na or SiMe$_3$.

Step (b1):
The step of azide reduction may in particular be carried out in the presence of hydrogen. A hydrogenation catalyst such as palladium on carbon may be used.

Step (c1):
When $R_3$=$NR_{26}R_{27}$, substitution of the amine function may be carried out by methods well-known to the person skilled in the art, in particular by a nucleophilic substitution reaction in the presence of $R_{26}LG_4$ and/or $R_{27}LG_5$, where LG$_4$ and LG$_5$ each represent, independently of each other, a leaving group. Such a reaction is advantageously carried out in the presence of a base. When $R_{26}$ and $R_{27}$ do not represent a hydrogen atom, two successive reactions may be carried out in order to introduce groups $R_{26}$ and $R_{27}$ successively.

When $NR_{38}COR_{39}$, this step may be carried out by methods well-known to the person skilled in the art, for example by peptide coupling or by using acyl chlorides of formula $R_{39}$COCl.

A third process for preparing a compound of formula (I) according to the invention, wherein $R_3$=CHOHCH$_2$OH, CHO, CO$_2$R$_{28}$, CONR$_{29}$R$_{30}$, OR$_{25}$, (O(CH$_2$)$_m$O(CH$_2$)$_p$)$_r$ (CH$_2$)$_q$R$_{31}$, NR$_{26}$R$_{27}$ or (NR$_{32}$(CH$_2$)$_w$NR$_{33}$(CH$_2$)$_x$)$_y$(CH$_2$)$_z$R$_{34}$, comprises:

(a2) to obtain a compound of formula (I) wherein $R_3$=CHOHCH$_2$OH, dihydroxylation reaction of the vinyl function of a compound of the following formula (IV):

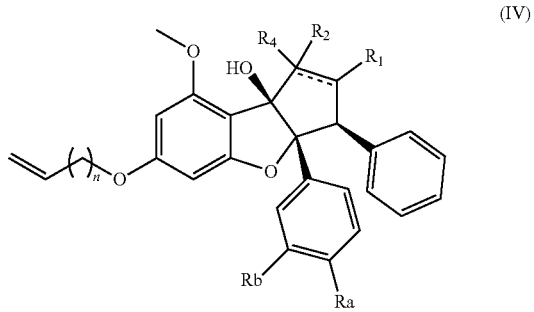

(IV)

wherein Ra, Rb, $R_1$, $R_2$, $R_4$ and n are as defined above,
(b2) to obtain a compound of formula (I) wherein $R_3$=CHO, oxidative cleavage of the CHOHCH$_2$OH group of a compound of formula (I) wherein $R_3$=CHOHCH$_2$OH optionally obtained according to step (a2),
(c2) to obtain a compound of formula (I) wherein $R_3$=CO$_2$H, oxidation of the aldehyde function of a compound of formula (I) wherein $R_3$=CHO optionally obtained according to step (b2),
(d2) to obtain a compound of formula (I) wherein $R_3$=CO$_2$R$_{28}$ and $R_{28}$≠H, substitution of the carboxylic acid function of a compound of formula (I) wherein $R_3$=CO$_2$H optionally obtained according to step (c2), (e2) to obtain a compound of formula (I) wherein $R_3=CONR_{29}R_{30}$, reacting a compound of formula (I) wherein $R_3=CO_2R_{28}$, optionally obtained according to step (b2) or (c2), with an amine of formula $HNR_{29}R_{30}$, (f2) to obtain a compound of formula (I) wherein $R_3=OH$, reduction of the aldehyde function of a compound of formula (I) wherein $R_3=CHO$ optionally obtained according to step (b2), (g2) to obtain a compound of formula (I) wherein $R_3=OR_{25}$ or $(O(CH_2)_mO(CH_2)_p)_r(CH_2)_qR_{31}$, $NR_{26}R_{27}$ with $R_{25}\ne H$, substitution of the hydroxyl function of a compound of formula (I) wherein $R_3=OH$ optionally obtained according to step (f2), (h2) to obtain a compound of formula (I) wherein $R_3=NR_{26}R_{27}$, reductive amination of the aldehyde function of a compound of formula (I) wherein $R_3=CHO$, optionally obtained according to step (b2), in the presence of an amine of formula $HNR_{26}R_{27}$.

Step (a2):

Such a reaction may be carried out particularly in the presence of $OsO_4$ and NMO (4-methylmorpholine N-oxide).

Step (b2):

This reaction may be carried out particularly in the presence of $NaIO_4$.

Step (c2):

Oxidation conditions are well-known to the person skilled in the art.

Step (d2) or (g2):

Such a reaction may be carried out under nucleophilic substitution conditions well-known to the person skilled in the art. The carboxylic acid function may be activated first, particularly in acyl chloride or anhydride form. Likewise, the alcohol function may be transformed into a leaving group such as a halogen atom or a sulfonate, for example.

Step (e2):

Such a reaction may be carried out under peptide coupling conditions or by nucleophilic substitution after activation of the carboxylic acid function, particularly in acyl chloride or anhydride form.

Step (f2):

Reduction conditions are well-known to the person skilled in the art. $NaBH_4$ may in particular be used as the reducing agent.

Step (h2):

Reductive amination conditions are well-known to the person skilled in the art. Such a reaction may be carried out in the presence of $NaBHOAc_3$ as the reducing agent.

A fourth process for preparing a compound of formula (I) according to the invention, wherein $R_1$ represents

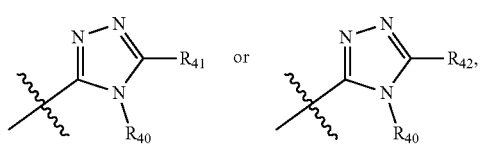

comprises reacting a compound of the following formula (V):

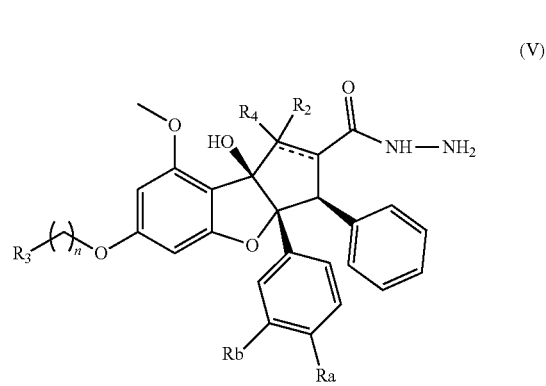

wherein Ra, Rb, $R_2$, $R_3$, $R_4$ and n are as defined above, with:

(1) a cyanogen of formula Hal-CN, wherein Hal represents a halogen atom such as Br, or an isothiocyanate of formula

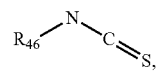

particularly in the presence of a base such as $NaHCO_3$, optionally followed by one or more substitution steps to give a compound of formula (I) wherein $R_1$ represents

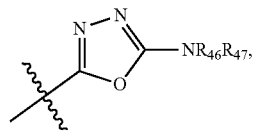

or
(2) carbon disulfide ($CS_2$) in the presence of a base such as NaOH or KOH, optionally followed by one or more substitution steps to give a compound of formula (I) wherein $R_1$ represents

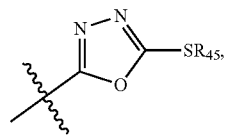

or
(3) carbonyldiimidazole in the presence of a base such as triethylamine, optionally followed by one or more substitution steps to give a compound of formula (I) wherein $R_1$ represents

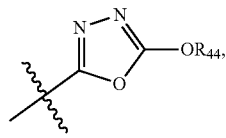

or
(4) a carboxylic acid of formula $R_{42}COOH$, wherein $R_{42}$ represents a $(C_1\text{-}C_6)$alkyl, aryl or aryl-$(C_1\text{-}C_6)$alkyl group, in the presence of POCl$_3$ to give a compound of formula (I) wherein R$_1$ represents O

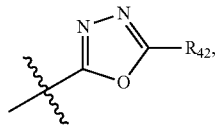

or
(5) an isothiourea of formula

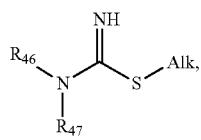

wherein Alk represents a (C$_1$-C$_6$)alkyl group, in the presence of a base such as NaOH or KOH, optionally followed by one or more substitution steps to give a compound of formula (I) wherein R$_1$ represents

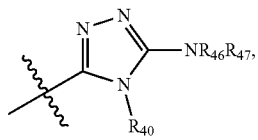

or
(6) an imidate of formula

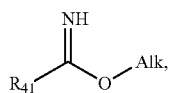

wherein R$_{41}$ represents a (C$_1$-C$_6$)alkyl, aryl or aryl-(C$_1$-C$_6$)alkyl group and Alk represents a (C$_1$-C$_6$)alkyl group, in the presence of a base such as triethylamine, optionally followed by one or more substitution steps to give a compound of formula (I) wherein R$_1$ represents

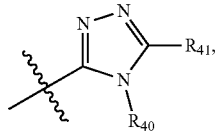

(7) triethyl orthoformate optionally followed by one or more substitution steps to give a compound of formula (I) wherein R$_1$

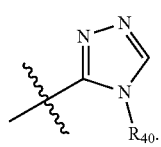

The reaction conditions for these various reactions are well-known to the person skilled in the art and are generally exemplified in the experimental section below. The same applies to the substitution reactions.

When R$_1$ represents

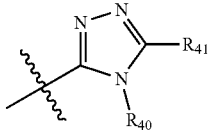

with R$_{41}$=H, the compound of formula (I) according to the invention may be prepared by reacting a compound of formula (I) wherein R$_1$=CONH$_2$ with dimethylformamide dimethylacetate, then reacting the product obtained with hydrazine.

When R$_1$ represents

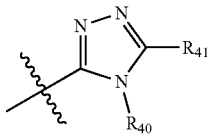

with R$_{41}$=OR$_{44}$, the compound of formula (I) according to the invention may be prepared by reacting a compound of formula (I) wherein

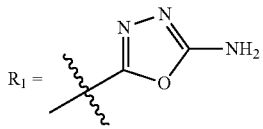 [SMILES: *c1nnc(N)o1]

by rearrangement of the amino-oxadiazole in the presence of KOH and an alcohol R$_{44}$OH.

When R$_1$ represents

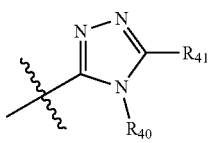

with R$_{41}$=SR$_{45}$, the compound of formula (I) according to the invention may be prepared by reacting a compound of formula (I) wherein R$_1$=COOH with a thiosemicarbazide.

A fifth process for preparing a compound of formula (I) according to the invention, wherein R$_1$ represents

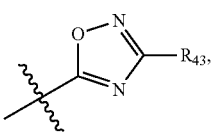

comprises reacting a compound of formula (I) with R$_1$=CO$_2$R$_{10}$ and R$_{10}$ represents a (C$_1$-C$_6$)alkyl group, with a hydroxy-imidamide of formula

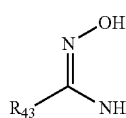

in the presence of a base such as $K_2CO_3$.

The reaction conditions for such a reaction are exemplified in the present patent application.

A sixth process for preparing a compound of formula (I) according to the invention, wherein

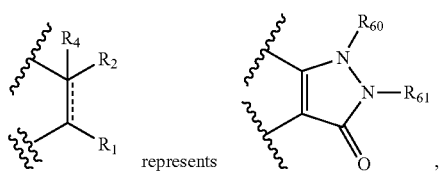

comprises reacting a compound of formula (I), wherein --- represents a double bond, $R_1=CO_2R_{10}$, $R_2$=OH, $R_4$=H and $R_{10}$=($C_1$-$C_6$)alkyl, with a hydrazine of formula $H_2N$—$NH_2$, optionally followed by one or more substitution steps.

The reaction conditions for such a coupling reaction with hydrazine are exemplified in the present patent application. The person skilled in the art also knows how to carry out a substitution reaction.

A seventh process for preparing a compound of formula (I) according to the invention, wherein

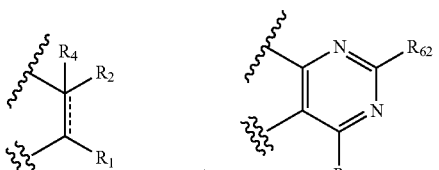

comprises reacting a compound of the following formula (VI):

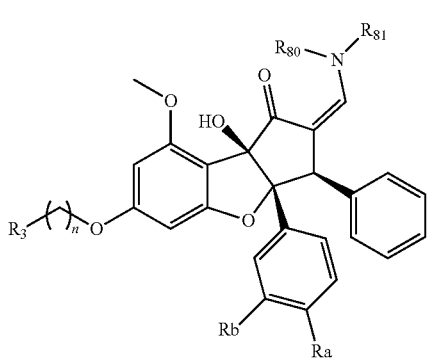

wherein Ra, Rb, $R_3$ and n are as defined above, and $R_{80}$ and $R_{81}$ represent, independently of each other, a ($C_1$-$C_6$)alkyl group, with a guanidine derivative of formula

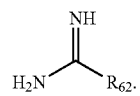

The reaction conditions for such a coupling reaction with a guanidine derivative are exemplified in the present patent application.

An eighth process for preparing a compound of formula (I) according to the invention, wherein

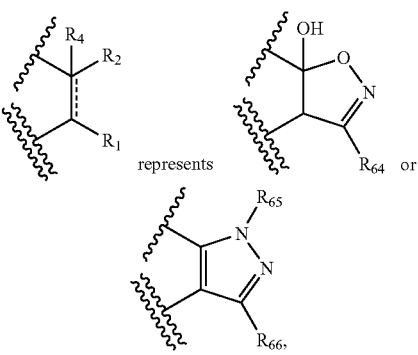

comprises reacting a compound of the following formula (VII):

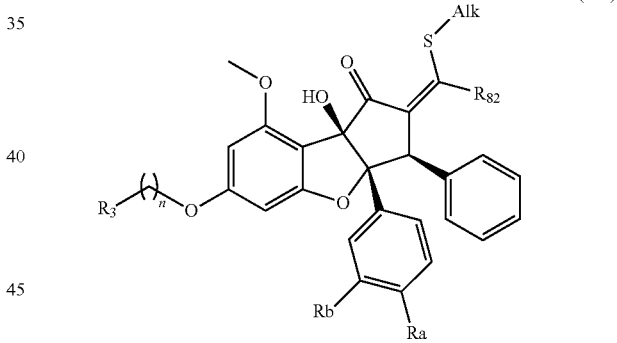

wherein Ra, Rb, $R_3$ and n are as defined above, Alk represents a ($C_1$-$C_6$)alkyl group, and $R_{82}$ represents $R_{64}$ or $R_{66}$, with:

(1) the hydroxylamine of formula HO—$NH_2$ in the presence of a base such as triethylamine, to give a compound of formula (I) wherein

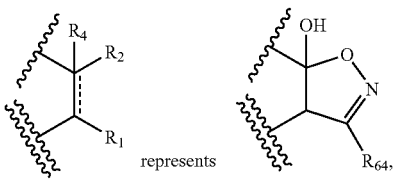

or (2) a hydrazine of formula $H_2N$—$NH_2$, optionally followed by one or more substitution steps to give a compound of formula (I) wherein

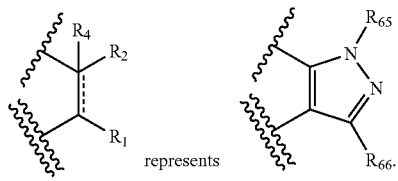 represents 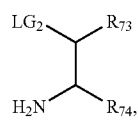

The reaction conditions for these coupling reactions are exemplified in the present patent application. The person skilled in the art also knows how to carry out a substitution reaction.

A ninth process for preparing a compound of formula (I) according to the invention, wherein

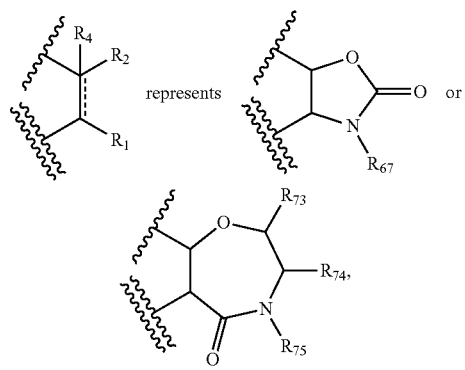

comprises reacting a compound of the following formula (VIII):

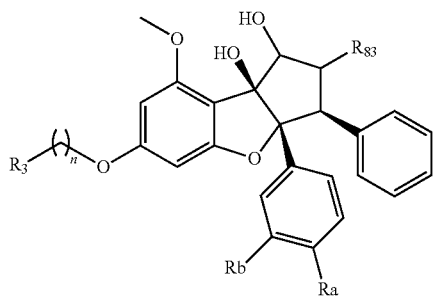

(VIII)

wherein Ra, Rb, $R_3$ and n are as defined above, and $R_{83}$ represents a $CO_2H$ group optionally in an activated form, with:
(1) an azide, under Curtius rearrangement conditions, optionally followed by one or more substitution steps, to give a compound of formula (I) wherein

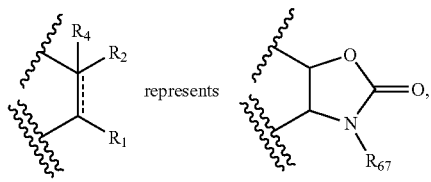

or
(2) an amine of formula $$LG_2 \diagup R_{73}$$
$$H_2N \diagdown R_{74},$$

wherein $LG_2$ represents a leaving group such as a halogen, in the presence of a base such as diisopropylethylamine (DIEA), optionally followed by one or more substitution steps, to give a compound of formula (I) wherein

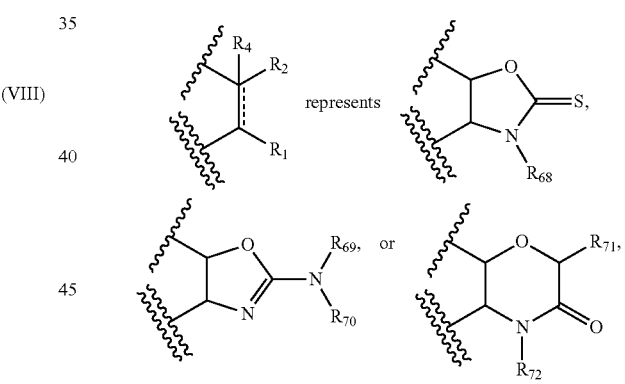

The Curtius rearrangement of step (1) is a reaction well-known to the person skilled in the art. It may be carried out particularly in the presence of diphenylphosphoryl azide (DPPA) and a base such as triethylamine. The compound (VIII) bears more particularly a group $R_{83}$=COOH.

The reaction conditions for step (2) and for optional subsequent substitution reactions are well-known to the person skilled in the art.

A tenth process for preparing a compound of formula (I) of the invention, wherein

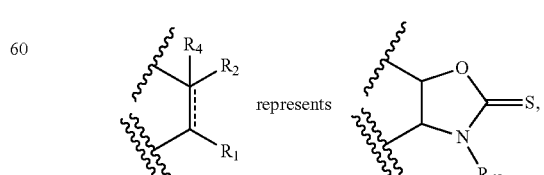

comprises reacting a compound of formula (I), wherein ⸺ represents a single bond, $R_1$=$NH_2$, $R_2$=OH and $R_4$=H, with:
(1) carbon disulfide ($CS_2$) in the presence of a base such as sodium carbonate, optionally followed by one or more substitution steps, to give a compound of formula (I) wherein or (2) a cyanogen of formula Hal-CN, wherein Hal represents a halogen atom such as Br, in the presence of a base such as $NaHCO_3$, optionally followed by one or more substitution steps, to give a compound of formula (I) wherein

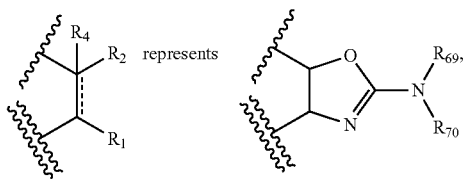

or (3) an ester of formula

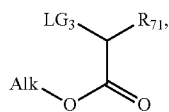

wherein Alk represents a $(C_1-C_6)$alkyl group and $LG_3$ represents a leaving group such as a halogen atom such as Cl, in the presence of a base such as NaH, optionally followed by one or more substitution steps, to give a compound of formula (I) wherein

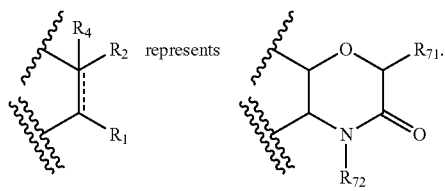

The reaction conditions for these steps and for the optional subsequent substitution reactions are known to the person skilled in the art.

The compounds of formulas (II) to (VIII) may be prepared by methods described in the prior art or in the present patent application.

The compound of formula (I) obtained by one of the above-mentioned processes may be separated from the reaction medium by methods well-known to the person skilled in the art, such as for example by extraction, solvent evaporation or by precipitation and filtration.

The compound may also be purified if necessary by techniques well-known to the person skilled in the art, such as by recrystallization if the compound is crystalline, by distillation, by silica-gel column chromatography or by high-performance liquid chromatography (HPLC).

The following examples illustrate the invention without however limiting its scope.

EXAMPLES

1—Synthesis of the Compounds According to the Invention

The following abbreviations were used in the examples below:
ES: Electrospray
HPLC: High-performance liquid chromatography
HRMS: High-resolution mass spectrum
LCMS: Liquid chromatography coupled to mass spectrometry
NMR: Nuclear magnetic resonance
RT: Room temperature The names of the compounds according to the present invention were assigned by Autonom.

1.1. Compounds with $R_1=CO_2Me$, $CO_2H$ or $CONH_2$ and $R_2=OH$

The compounds according to the invention can be synthesized according to the following reaction diagram:

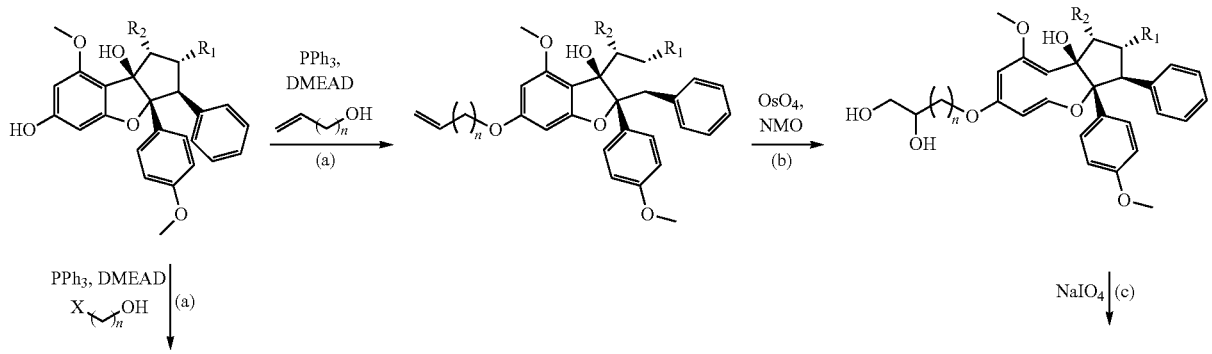

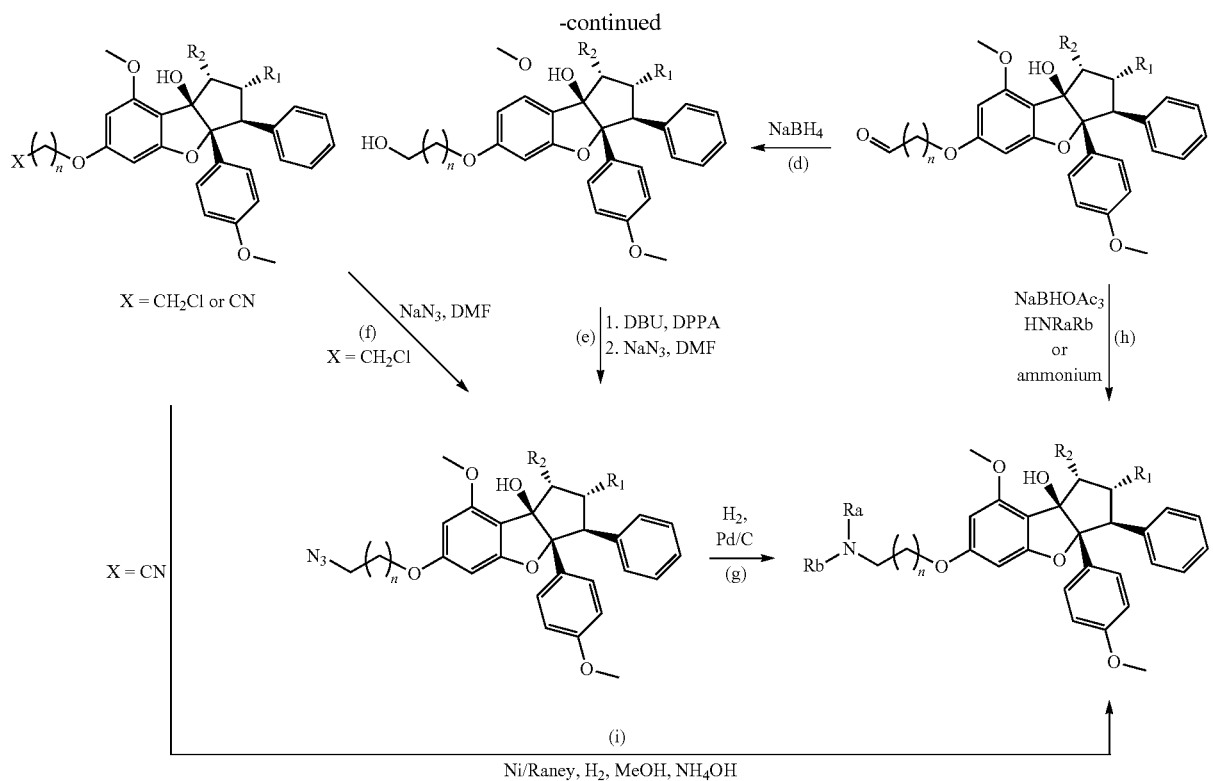

(a) Procedure for the substitution reaction of the phenol (example R₁=CO₂Me, R₂=OH, n=3, alcohol=4-chloro-1-butanol): In a one-liter round-bottom flask, dissolve rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate (R₁=CO₂Me, R₂=OH, 10.25 g, 21.42 mmol) in 200 mL of toluene then add 4-chloro-1-butanol (12.57 mL, 107 mmol) and PPh₃ (28.1 g, 107 mmol). At 0° C. and under nitrogen, add dropwise bis(2-methoxyethyl) azodicarboxylate (DMEAD, 8.1 g, 120 mmol) dissolved in 155 mL of toluene. Stir at 0° C. for 10 min then at room temperature for 4.5 hours. Add a little water then extract twice with ethyl acetate, wash once with H₂O/NaCl then dry the organic phases over MgSO₄, filter then evaporate under reduced pressure. The orange oil obtained is taken up in diethyl ether, a white precipitate forms, the white solid is removed by filtration and the filtrate is evaporated. The residue is purified on silica gel using as eluent an 80:20 to 50:50 cyclohexane/AcOEt mixture.

(b) Procedure for the dihydroxylation reaction (example R₁=CO₂Me, R₂=OH, n=3): To a solution of rac-methyl (1R,2R,3S,3aR,8bS)-1,8b-dihydroxy-8-methoxy-3a-(4-methoxyphenyl)-6-(pent-4-en-1-yloxy)-3-phenyl-2,3,3a,8b-tetrahydro-1H-cyclopenta[b]benzofuran-2-carboxylate (1.4 g, 2.56 mmol) in tetrahydrofuran (THF, 17 mL), under argon atmosphere, add 4-methylmorpholine N-oxide monohydrate (NMO, 0.535 g, 3.84 mmol) dissolved in water (2.5 mL) then osmic acid (3.24 mL, 0.512 mmol). Stir vigorously magnetically at room temperature for 1 hour. Add saturated NaHSO₃ solution, extract with ethyl acetate twice, dry the organic phase over Na₂SO₄, filter then evaporate. The residue is purified on silica gel using as eluent a 95:5 to 80:20 CH₂Cl₂/MeOH mixture.

(c) Procedure for the oxidative cleavage reaction (example R₁=CO₂Me, R₂=OH, n=3): To a solution of rac-methyl (1R,2R,3S,3aR,8bS)-6-((4,5-dihydroxypentyl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate (102 mg, 0.176 mmol) in THF (1.5 mL) and water (1.5 mL), add sodium periodate (39 mg, 1.05 equiv.) at 0° C., then allow the mixture to return to room temperature and stir magnetically for 3 hours. Add water and dichloromethane (DCM), extract 3 times with dichloromethane then ethyl acetate. Dry the organic phases over Na₂SO₄, filter then evaporate. Use the crude product without further purification.

(d) Procedure for the aldehyde reduction reaction (example R₁=CO₂Me, R₂=OH, n=3): In a round-bottom flask, introduce rac-methyl (1R,2R,3S,3aR,8bS)-1,8b-dihydroxy-8-methoxy-3a-(4-methoxyphenyl)-6-(4-oxobutoxy)-3-phenyl-2,3,3a,8b-tetrahydro-1H-cyclopenta[b]benzofuran-2-carboxylate (2.66 g, 4.85 mmol) dissolved in methanol (50 mL), add NaBH₄ (0.275 g, 7.27 mmol) and stir at room temperature for 1.5 hours. Add saturated NH₄Cl solution (75 mL), concentrate then extract 3 times with ethyl acetate. Combine the organic phases, wash with NaCl then dry over Na₂SO₄, filter and concentrate under reduced pressure. The residue is purified on silica gel using as eluent DCM to 80:20 DCM/MeOH.

(e) Procedure for synthesizing the azide from the alcohol (example R₁=CO₂Me, R₂=OH, n=3): In the round-bottom flask containing rac-methyl (1R,2R,3S,3aR,8bS)-1,8b-dihydroxy-6-(4-hydroxybutoxy)-8-methoxy-3a-(4-methoxyphenyl)-3-phenyl-2,3,3a,8b-tetrahydro-1H-cyclopenta[b]benzofuran-2-carboxylate (1 g, 1.816 mmol), add tetrahydrofuran (8 mL). Reduce the temperature to 0° C. and add diphenylphosphoryl azide (DPPA, 0.866 mL, 4.00 mmol) and 1,8-diazabicyclo[5.4.0]undec-7-ene (DBU, 0.706 mL, 4.72 mmol). Allow to return to room temperature and stir magnetically for 1 hour. Evaporate the crude product then dilute it with dimethylformamide (DMF, 20 mL), add sodium azide (0.354 g, 5.44 mmol) and heat the mixture to 110° C. for 5 hours. Evaporate the DMF under reduced pressure and purify the residue on silica gel using as eluent a 100:0 to 85:15 $CH_2Cl_2$/AcOEt mixture.

(f) Procedure for synthesizing the azide from the chlorinated compound (example R=$CO_2Me$, $R_2$=OH, n=3): In the round-bottom flask containing rac-methyl (1R,2R,3S,3aR,8bS)-6-(4-chlorobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate (3.6 g, 6.34 mmol) introduce DMF (35 mL), add sodium azide (0.825 g, 12.69 mmol) and heat the mixture to 110° C. for 5 hours. Evaporate the DMF under reduced pressure and purify the residue on silica gel using as eluent 100:0 to 85:15 $CH_2Cl_2$/AcOEt.

(g) Azide reduction procedure (example $R_1$=$CO_2Me$, $R_2$=OH, n=3): In a 500 mL round-bottom flask, dissolve rac-(1R,2R,3S,3aR,8bS)-methyl 6-(4-azidobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate (3.65 g, 6.34 mmol) in ethanol (68 mL) and tetrahydrofuran (68.0 mL). Purge under nitrogen then add palladium on carbon (1.350 g, 1.268 mmol) under nitrogen. Place the reaction mixture under hydrogen atmosphere and stir at room temperature for 3 hours. Filter the palladium on a Dicalite® cake then rinse with ethanol and THF, evaporate the filtrate under reduced pressure. The residue obtained is purified on silica gel using as eluent a 30:70 cyclohexane/AcOEt then 90:9:1 $CH_2Cl_2$/MeOH/$NH_4OH$ (7 N in methanol) mixture.

(h) Reductive amination procedure (example $R_1$=$CO_2Me$, $R_2$=OH, n=3): In a round-bottom flask, introduce rac-methyl (1R,2R,3S,3aR,8bS)-1,8b-dihydroxy-8-methoxy-3a-(4-methoxyphenyl)-6-(4-oxobutoxy)-3-phenyl-2,3,3a,8b-tetrahydro-1H-cyclopenta[b]benzofuran-2-carboxylate (0.050 g, 0.091 mmol) dissolved in 1,2-dichloroethane (2 mL) and methanol (0.5 mL), add ammonium acetate (5 equiv.) then sodium triacetoxyborohydride (2.0 equiv.), stir at room temperature for 18 hours. Add saturated $NaHCO_3$ solution then dilute with DCM, extract twice with DCM then combine the organic phases and wash with saturated NaCl solution, dry the organic phase over $Na_2SO_4$, filter and concentrate under reduced pressure. The residue is purified on silica gel using as eluent a 90:10 DCM/MeOH mixture.

(i) Nitrile reduction procedure (example $R_1$=$CO_2Me$, $R_2$=OH, n=3): In a hydrogenation reactor, mix Raney nickel (100 mg, 0.852 mmol), rac-(1R,2R,3S,3 aR,8bS)-methyl-6-(3-cyanopropoxy)-1,8b-dihydroxy-8-methoxy-3a-(4-methoxyphenyl)-3-phenyl-2,3,3a,8b-tetrahydro-1H-cyclopenta[b]benzofuran-2-carboxylate (100 mg, 0.183 mmol) and 7 N $NH_4OH$ in MeOH (5 mL) and a little MeOH (=rinsing the used equipment). The mixture is place under hydrogen atmosphere and stirred at room temperature for 18 hours. Filter on a 0.45 m Acrodisc® then rinse well with methanol, evaporate, a white solid is obtained (m=101 mg, quantitative yield).

The compounds obtained by these various processes are characterized below.

Compound 1 rac-(1R,2R,3S,3aR,8bS)-methyl 6-(2,3-dihydroxypropoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

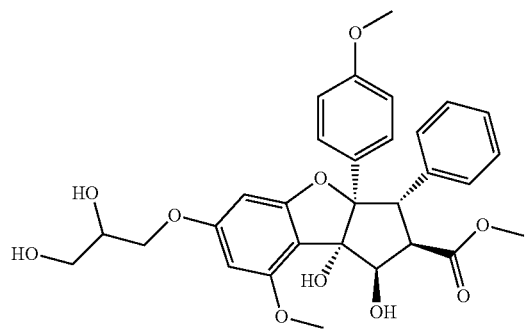 [SMILES: COC(=O)[C@H]1[C@@H](O)[C@@]2(O)c3c(OC)cc(OCC(O)CO)cc3O[C@@]2(c2ccc(OC)cc2)[C@@H]1c1ccccc1]

White solid, 30.1 mg (31%); obtained from rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate by following the phenol substitution procedure with prop-2-en-1-ol as the alcohol, then the dihydroxylation procedure.

$^1$H NMR ($CDCl_3$, 400 MHz, δ, ppm): 7.10 (d, 2H, J=8.6 Hz), 7.06 (m, 3H), 6.87 (m, 2H), 6.67 (d, 2H, J=8.6 Hz), 6.29 (s, 1H), 6.15 (s, 1H), 5.02 (d, 1H, J=6.5 Hz), 4.30 (d, 1H, J=14.1 Hz), 4.11 (m, 1H), 4.05 (m, 2H), 3.90 (dd, 1H, J=6.6 Hz, 14.1 Hz), 3.84 (dd, 1H, J=3.6 Hz, 11.7 Hz), 3.78 (s, 3H), 3.73 (m, 1H), 3.70 (s, 3H), 3.64 (s, 3H); LCMS (ES+, m/z): 534.93 [M−OH]$^+$; LCMS (ES−, m/z): 596.83 [M+HCOO$^-$]$^-$.

Compound 2 rac-(1R,2R,3S,3aR,8bS)-methyl 6-(2-aminoethoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

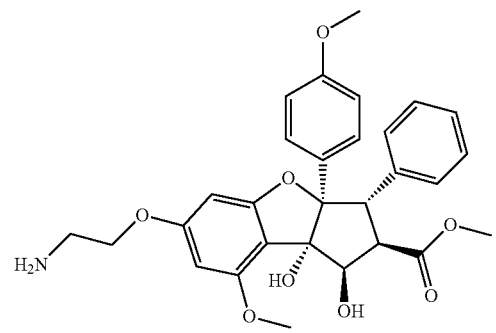 [SMILES: COC(=O)[C@H]1[C@@H](O)[C@@]2(O)c3c(OC)cc(OCCN)cc3O[C@@]2(c2ccc(OC)cc2)[C@@H]1c1ccccc1]

White solid, 16 mg (66%); obtained from rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate by following the phenol substitution procedure with 2-chloroethan-1-ol as the alcohol, then the azide synthesis and reduction procedures.

¹H NMR (CDCl₃, 400 MHz, δ, ppm): 7.12 (d, 2H, J=8.7 Hz), 7.05 (m, 3H), 6.83 (m, 2H), 6.67 (d, 2H, J=8.7 Hz), 6.20 (d, 1H, J=1.6 Hz), 6.10 (d, 1H, J=1.6 Hz), 5.02 (d, 1H, J=6.7 Hz), 4.26 (d, 1H, J=14.1 Hz), 3.84 (m, 6H), 3.71 (s, 3H), 3.63 (s, 3H), 2.87 (m, 2H); LCMS (ES+, m/z): 503.97 [M−OH]⁺; LCMS (ES−, m/z): 565.87 [M+HCOO⁻]⁻.

Compound 3 rac-(1R,2R,3S,3aR,8bS)-methyl 6-((4,5-dihydroxypentyl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

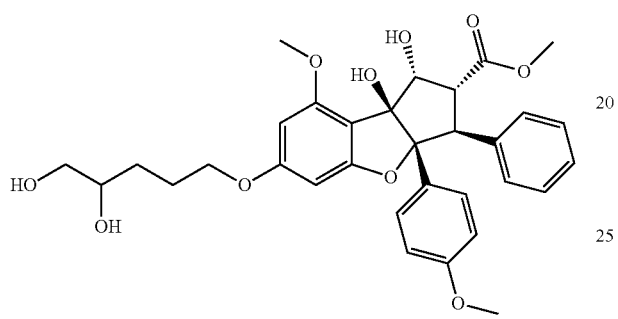

White solid, obtained from rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate by following the phenol substitution procedure with pent-4-en-1-ol as the alcohol, then the dihydroxylation procedure.

¹H NMR (CDCl₃, 400 MHz, δ, ppm): 7.05 (m, 5H), 6.84 (m, 2H), 6.63 (m, 2H), 6.23 (d, 1H, J=1.4 Hz), 6.09 (d, 1H, J=1.4 Hz), 4.99 (d, 1H, J=6.7 Hz), 4.25 (d, 1H, J=14.1 Hz), 3.96 (m, 2H), 3.86 (m, 1H), 3.82 (s, 3H), 3.65 (s, 3H), 3.62 (s, 3H), 3.51 (dd, 1H, J=2.8 Hz, 11.2 Hz), 3.32 (dd, 1H, J=7.6 Hz, 11.2 Hz), 1.84 (m, 2H), 1.51 (m, 2H); LCMS (ES+, m/z): 563.0 [M−OH]; LCMS (ES−, m/z): 625.0 [M+HCOO⁻]⁻.

Compound 4 rac-(1R,2R,3S,3aR,8bS)-methyl 1,8b-dihydroxy-8-methoxy-3a-(4-methoxyphenyl)-6-(4-oxobutoxy)-3-phenyl-2,3,3a,8b-tetrahydro-1H-cyclopenta[b]benzofuran-2-carboxylate

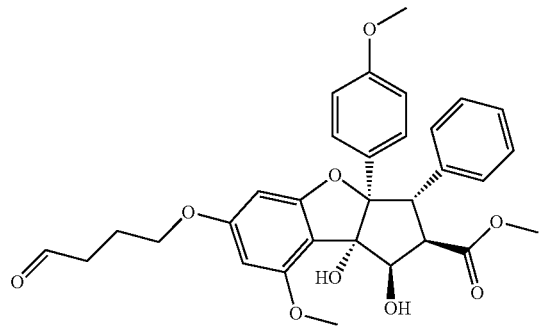 [SMILES: COC(=O)[C@H]1[C@@H](O)[C@@]2(O)c3c(OC)cc(OCCCC=O)cc3O[C@@]2(c2ccc(OC)cc2)[C@@H]1c1ccccc1]

White solid; obtained from compound 3 by following the oxidative cleavage procedure.

¹H NMR (CDCl₃, 400 MHz, δ, ppm): 9.80 (s, 1H), 7.06 (m, 5H), 6.85 (m, 2H), 6.64 (m, 2H), 6.23 (d, 1H, J=1.7 Hz), 6.08 (d, 1H, J=1.7 Hz), 5.00 (d, 1H, J=6.7 Hz), 4.27 (d, 1H, J=14.1 Hz), 3.99 (t, 2H, J=6.1 Hz), 3.87 (dd, 1H, J=6.7 Hz, 14.1 Hz), 3.84 (s, 3H), 3.67 (m, 1H), 3.66 (s, 3H), 3.62 (s, 3H), 2.64 (dd, 2H, J=6.7 Hz, 7.2 Hz), 2.10 (m, 2H); LCMS (ES+, m/z): 530.98 [M−OH]⁺; LCMS (ES−, m/z): 592.97 [M+HCOO⁻]⁻.

Compound 5 rac-(1R,2R,3S,3aR,8bS)-methyl 1,8b-dihydroxy-6-(4-hydroxybutoxy)-8-methoxy-3a-(4-methoxyphenyl)-3-phenyl-2,3,3a,8b-tetrahydro-1H-cyclopenta[b]benzofuran-2-carboxylate

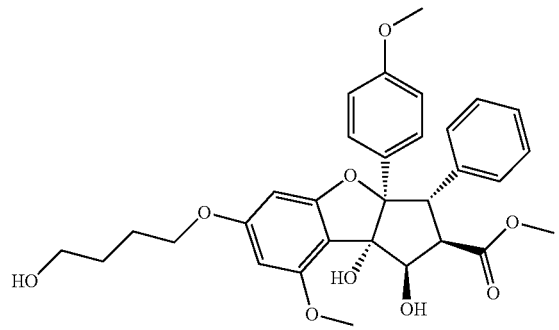 [SMILES: COC(=O)[C@H]1[C@@H](O)[C@@]2(O)c3c(OC)cc(OCCCCO)cc3O[C@@]2(c2ccc(OC)cc2)[C@@H]1c1ccccc1]

White foam, 1.72 g (64%); obtained from compound 4 by following the reduction procedure.

¹H NMR (DMSO-D₆, 400 MHz, δ, ppm): 7.02 (m, 5H), 6.87 (d, 1H, J=7.4 Hz), 6.58 (d, 2H, J=8.7 Hz), 6.26 (s, 1H), 6.09 (s, 1H), 5.07 (s, 1H), 5.02 (d, 1H, J=5.0 Hz), 4.68 (t, 1H, J=5.0 Hz), 4.47 (t, 1H, J=5.0 Hz), 4.13 (d, 1H, J=14.0 Hz), 4.00 (t, 2H, J=6.5 Hz), 3.91 (dd, 1H, J=5.0 Hz, 14.0 Hz), 3.73 (s, 3H), 3.60 (s, 3H), 3.54 (s, 3H), 3.47 (m, 2H), 1.75 (m, 2H), 1.58 (m, 2H); LCMS (ES+, m/z): 532.97 [M−OH]⁺; LCMS (ES−, m/z): 594.99 [M+HCOO⁻]⁻.

Compound 6 rac-(1R,2R,3S,3aR,8bS)-methyl 6-(4-((3-((4-((3-aminopropyl)amino)butyl)amino)propyl)amino)butoxy)-1,8b-dihydroxy-8-methoxy-3a-(4-methoxyphenyl)-3-phenyl-2,3,3a,8b-tetrahydro-1H-cyclopenta[b]benzofuran-2-carboxylate, hydrochloric Acid Salt

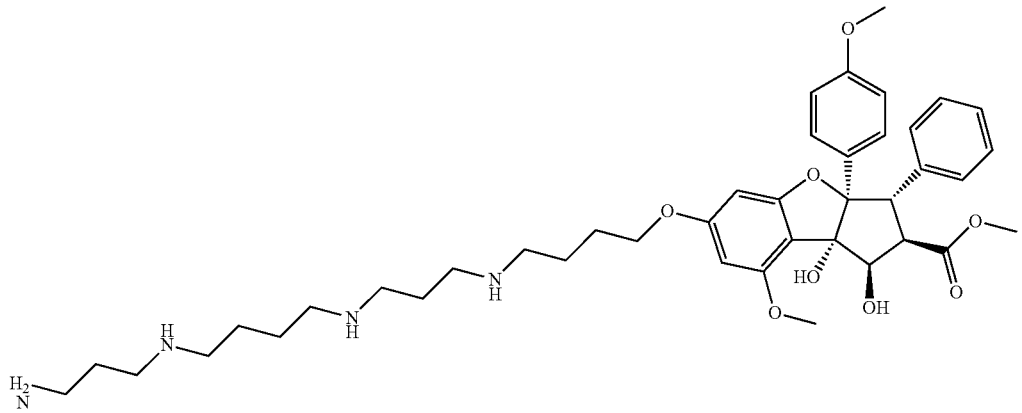 [SMILES: COC(=O)[C@H]1[C@@H](O)[C@@]2(O)c3c(OC)cc(OCCCCNCCCNCCCCNCCCN)cc3O[C@@]2(c2ccc(OC)cc2)[C@@H]1c1ccccc1]

White solid, 20 mg (66%); obtained from compound 4 by following the reductive amination procedure using tert-butyl (4-((3-aminopropyl)(tert-butoxycarbonyl)amino)butyl)(3-((tert-butoxycarbonyl)amino)propyl)carbamate as the amine. The final deprotection is carried out according to the conditions described in [J. Org. Chem. 2006, 71, 9045-9050].

$^1$H NMR (DMSO-D$_6$, 400 MHz, δ, ppm): 7.03 (m, 5H), 6.87 (m, 2H), 6.59 (m, 2H), 6.29 (s, 1H), 6.09 (s, 1H), 5.11 (m, 1H), 5.09 (s, 1H), 4.70 (m, 1H), 4.12 (d, 1H, J=14.4 Hz), 4.05 (m, 2H), 3.94 (dd, 1H, J=14.4 Hz, 5.8 Hz), 3.73 (s, 3H), 3.61 (s, 3H), 3.55 (s, 3H), 3.16 (m, 5H), 2.94 (m, 7H), 2.03-1.58 (m, 11H); HRMS: C41H59N4O8 [M+H]$^+$ calc. 735.4327 found 735.4335.

Compound 7 rac-(1R,2R,3S,3aR,8bS)-methyl 1,8b-dihydroxy-8-methoxy-6-(4-methoxy-4-oxobutoxy)-3a-(4-methoxyphenyl)-3-phenyl-2,3,3a,8b-tetrahydro-1H-cyclopenta[b]benzofuran-2-carboxylate

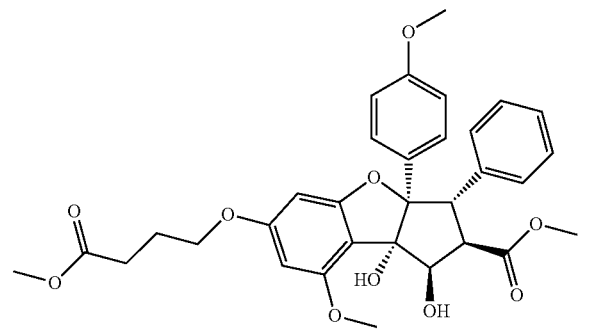

White solid, 3.8 mg (7%); obtained from compound 4 by carrying out an oxidation as follows: To a mixture of compound 4 (1 equiv.) and 2-methyl-2-butene (4.5 equiv.) in acetone (0.1 M) are added a solution of NaH$_2$PO$_4$ (3 equiv., 0.5 M) in water then sodium chlorite (3 equiv.), the reaction mixture is stirred vigorously for 18 hours. The mixture is diluted with water and ethyl acetate, the pH of the aqueous phase is adjusted to 6 by adding HCl (1 N), the organic phase is then extracted then dried over sodium sulfate, filtered and concentrated to give carboxylic acid in the form of a white foam. This compound is dissolved in a 1:1 mixture of methanol and toluene (0.05 M) then trimethylsilyldiazomethane is added (4 equiv.), the reaction mixture is stirred for 18 hours at room temperature. The solvents are then evaporated and the residue is purified on silica gel.

$^1$H NMR (CDCl$_3$, 400 MHz, δ, ppm): 7.12 (d, 2H, J=8.7 Hz), 7.08 (m, 3H), 6.89 (m, 2H), 6.70 (d, 2H, J=8.7 Hz), 6.28 (d, 1H, J=1.9 Hz), 6.14 (d, 1H, J=1.9 Hz), 5.04 (d, 1H, J=6.7 Hz), 4.32 (d, 1H, J=14.1 Hz), 4.06 (t, 2H, J=6.0 Hz), 3.92 (dd, 1H, J=6.7 Hz, 14.1 Hz), 3.89 (s, 3H), 3.74 (s, 3H), 3.73 (s, 3H), 3.68 (m, 1H), 3.67 (s, 3H), 2.57 (m, 2H), 2.16 (m, 2H); LCMS (ES+, m/z): 561.0 [M−OH]$^+$; LCMS (ES−, m/z): 622.9 [M+HCOO$^−$]$^−$.

Compound 8 rac-(1R,2R,3S,3aR,8bS)-methyl 6-(4-aminobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

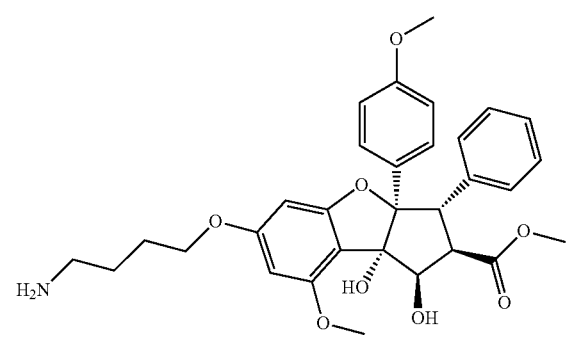 [SMILES: COC(=O)[C@H]1[C@@H](O)[C@@]2(O)c3c(OC)cc(OCCCCN)cc3O[C@@]2(c2ccc(OC)cc2)[C@@H]1c1ccccc1]

White solid, 45 mg (7%); obtained from compound 5 by following the azide synthesis then azide reduction procedures, this compound may also be obtained from rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate by following the phenol substitution procedure with 4-chlorobutan-1-ol as the alcohol, then the azide synthesis and reduction procedures. This compound may also be obtained from rac-(1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate by following the phenol substitution procedure with 4-hydroxybutanenitrile then the nitrile reduction procedure.

$^1$H NMR (DMSO-D$_6$, 400 MHz, δ, ppm): 7.02 (m, 5H), 6.87 (m, 2H), 6.59 (d, 2H, J=8.9 Hz), 6.26 (d, 1H, J=1.9 Hz), 6.10 (d, 1H, J=1.9 Hz), 5.07 (bs, 1H), 5.01 (d, 1H, J=4.4 Hz), 4.68 (m, 1H), 4.14 (d, 1H, J=14.1 Hz), 3.99 (t, 2H, J=6.5 Hz), 3.91 (dd, 5.7 Hz, 14.1 Hz), 3.73 (s, 3H), 3.60 (s, 3H), 3.54 (s, 3H), 2.60 (t, 2H, J=6.5 Hz), 1.74 (m, 2H), 1.50 (m, 2H); LCMS (ES+, m/z): 550.0 [M+H]$^+$; LCMS (ES−, m/z): 593.98 [M+HCOO$^-$]$^-$.

Compound 50 methyl (1R,2R,3S,3aR,8bS)-6-(4-aminobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

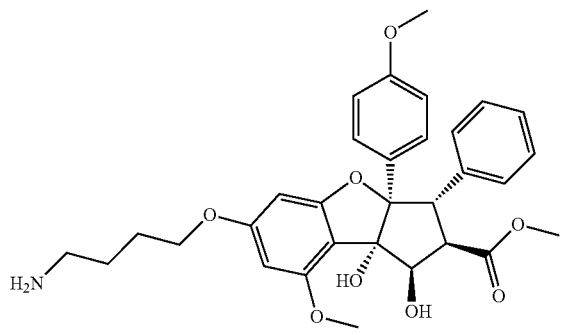 [SMILES: COC(=O)[C@H]1[C@@H](O)[C@@]2(O)c3c(OC)cc(OCCCCN)cc3O[C@@]2(c2ccc(OC)cc2)[C@@H]1c1ccccc1]

Beige solid, obtained from compound 8 by chiral separation by HPLC using a Chiralpak® IC 4.6×250 mm DAICEL column using as eluent a 50:50:0.05 heptane/ethanol/BUA (butylamine) mixture.

NMR and mass identical to compound 8; e.e. 93%; [α]$_D^{20}$=−54.0° (c 0.43 MeOH).

Compound 51 methyl (1S,2S,3R,3aS,8bR)-6-(4-aminobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

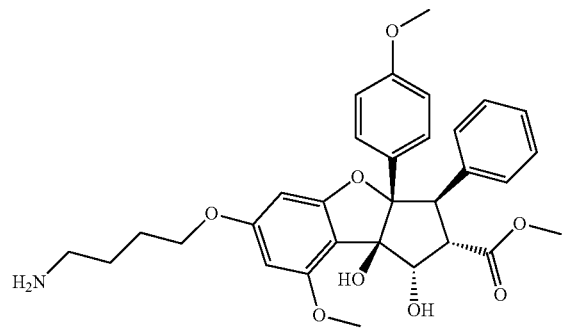 [SMILES: COC(=O)[C@@H]1[C@H](O)[C@]2(O)c3c(OC)cc(OCCCCN)cc3O[C@]2(c2ccc(OC)cc2)[C@H]1c1ccccc1]

Beige solid, obtained from compound 8 by chiral separation by HPLC using a Chiralpak® IC 4.6×250 mm DAICEL column using as eluent a 50:50:0.05 heptane/ethanol/BUA mixture.

NMR and mass identical to compound 8; e.e. 99%; [α]$_D^{20}$=+61.5° (c 0.47 MeOH).

Compound 52 rac-methyl (1R,2R,3S,3aR,8bS)-6-(4-(dimethylamino)butoxy)-1,8b-dihydroxy-8-methoxy-3a-(4-methoxyphenyl)-3-phenyl-2,3,3a,8b-tetrahydro-1H-cyclopenta[b]benzofuran-2-carboxylate

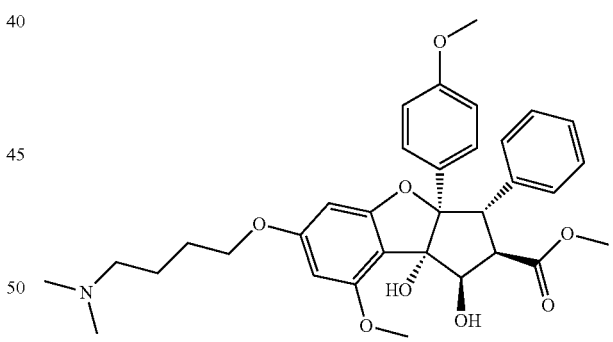

White solid, m=40.5 mg (38%); obtained from the chlorine compound according to the following procedure: in a pill machine, mix rac-(1R,2R,3S,3aR,8bS)-methyl 6-(4-chlorobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylate (100 mg, 0.176 mmol) in DMF (1.5 mL) then add 40% dimethylamine in water (501 µL, 3.95 mmol). Heat to 90° C. for 1 hour. Evaporate to dryness. A yellow oil is obtained. Purify on silica gel using as eluent a 90:10 CH$_2$Cl$_2$/MeOH mixture.

$^1$H NMR (DMSO-D$_6$, 400 MHz, δ, ppm): 7.01 (m, 5H), 6.86 (m, 2H), 6.58 (m, 2H), 6.28 (m, 1H), 6.10 (m, 1H), 5.07 (s, 1H), 5.045 (m, 1H), 4.68 (m, 1H), 4.13 (m, 1H), 4.02 (m, 2H), 3.91 (m, 1H), 3.73 (s, 3H), 3.59 (s, 3H), 3.53 (s, 3H), 2.96 (m, 2H), 2.64 (s, 6H), 1.76 (m, 4H); LCMS (ES+, m/z): 578.05 [M+H]⁺; LCMS (ES−, m/z): 622.01 [M+HCOO⁻]⁻.

Compound 53 rac-(1R,2R,3S,3aR,8bS)-6-(4-aminobutoxy)-1,8b-dihydroxy-8-methoxy-3a-(4-methoxyphenyl)-3-phenyl-2,3,3a,8b-tetrahydro-1H-cyclopenta[b]benzofuran-2-carboxylic acid

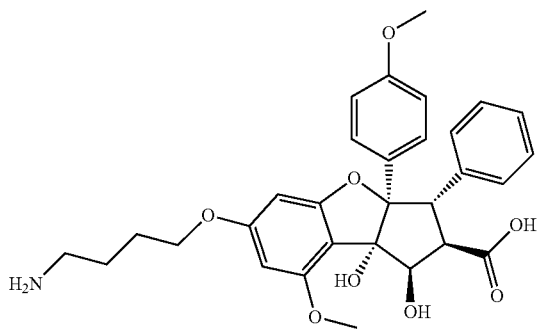 [SMILES: COc1ccc([C@@]23Oc4cc(OCCCCN)cc(OC)c4[C@]2(O)[C@H](O)[C@H](C(=O)O)[C@H]3c2ccccc2)cc1]

White solid, 366 mg (88%); obtained from compound 8: in a 20 mL flask, dissolve compound 8 (500 mg, 0.774 mmol) and K₂CO₃ (535 mg, 3.87 mmol) in methanol (5.00 mL) and water (5 mL). Stir at 70° C. for 4.5 hours; after returning to room temperature, the crude product is evaporated then the residue is purified on silica using as eluent a 50:50:4 CH₂Cl₂/MeOH/water mixture.

¹H NMR (DMSO-D₆, 400 MHz, δ, ppm): 7.02 (m, 5H), 6.89 (m, 2H), 6.58 (m, 2H), 6.28 (m, 1H), 6.07 (m, 1H), 4.98 (m, 2H), 4.65 (m, 1H), 4.09 (m, 1H), 4.02 (m, 2H), 3.73 (s, 3H), 3.59 (s, 3H), 2.88 (m, 2H), 1.74 (m, 4H); LCMS (ES+, m/z): 535.97 [M+H]⁺; LCMS (ES−, m/z): 533.87 [M−H]⁻.

Compound 54 rac-(1R,2R,3S,3aR,8bS)-1,8b-dihydroxy-6-(4-hydroxybutoxy)-8-methoxy-3a-(4-methoxyphenyl)-3-phenyl-2,3,3a,8b-tetrahydro-1H-cyclopenta[b]benzofuran-2-carboxamide

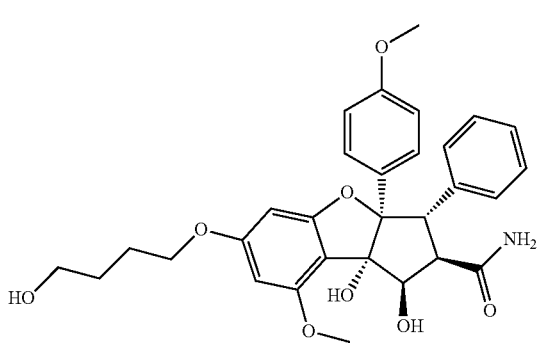 [SMILES: COc1ccc([C@@]23Oc4cc(OCCCCO)cc(OC)c4[C@]2(O)[C@H](O)[C@H](C(N)=O)[C@H]3c2ccccc2)cc1]

White solid, 475 mg (99%); obtained from compound 5 by following the hydrazide synthesis procedure (see above), then the hydrazide obtained (490 mg, 0.890 mmol) is reduced by adding it to a suspension of Raney nickel (313 mg, 2.67 mmol) in DMF (3 mL) and water (3 mL). The mixture obtained is heated to 100° C. for 1.5 hours. After returning to room temperature, the nickel is removed by filtration (AcOEt, CH₂Cl₂, MeOH) and the filtrate is concentrated under reduced pressure. The residue is purified on silica gel using as eluent a 90:10 CH₂Cl₂/MeOH mixture.

¹H NMR (DMSO-D₆, 400 MHz, δ, ppm): 7.66 (s, 1H), 6.99 (m, 8H), 6.58 (m, 2H), 6.24 (s, 1H), 6.08 (s, 1H), 4.95 (s, 1H), 4.64 (d, 1H, J=3.2 Hz), 4.54 (m, 1H), 4.69 (t, 1H, J=5.3 Hz), 4.14 (d, 1H, J=14.0 Hz), 3.99 (m, 1H), 3.78 (dd, 1H, J=5.3 Hz, 14.0 Hz), 3.72 (s, 3H), 3.59 (s, 3H), 3.46 (m, 2H), 1.75 (m, 2H), 1.57 (m, 2H); LCMS (ES+, m/z): 536.03 [M+H]⁺.

Compound 55 rac-(1R,2R,3S,3aR,8bS)-6-(4-aminobutoxy)-1,8b-dihydroxy-8-methoxy-3a-(4-methoxyphenyl)-3-phenyl-2,3,3a,8b-tetrahydro-1H-cyclopenta[b]benzofuran-2-carboxamide formate

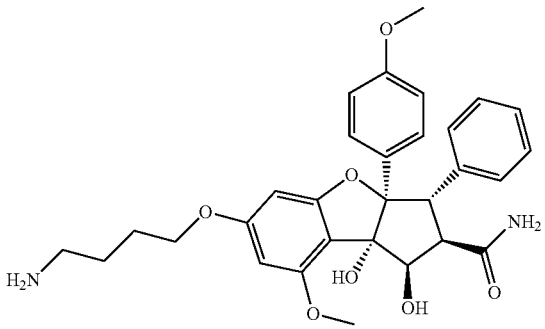 [SMILES: COc1ccc([C@@]23Oc4cc(OCCCCN)cc(OC)c4[C@]2(O)[C@H](O)[C@H](C(N)=O)[C@H]3c2ccccc2)cc1]

White solid, 105 mg (42%): obtained from compound 54 by following the procedure for synthesizing azide from the alcohol then the azide reduction procedure.

¹H NMR (DMSO-D⁶, 400 MHz, δ, ppm): 8.42 (s, 1H), 7.69 (s, 1H), 7.04 (m, 3H), 6.97 (m, 3H), 6.59 (d, 2H, J=8.9 Hz), 6.27 (d, 1H, J=1.9 Hz), 6.09 (d, 1H, J=1.9 Hz), 4.92 (bs, 1H), 4.66 (bs, 1H), 4.56 (d, 1H, J=5.5 Hz), 4.15 (d, 1H, J=14.3 Hz), 4.01 (t, 2H, J=6.0 Hz), 3.80 (dd, 1H, J=6.0 Hz, 14.3 Hz), 3.73 (s, 3H), 3.61 (s, 3H), 2.82 (t, 2H, J=7.5 Hz), 1.77 (m, 2H), 1.68 (m, 2H); LCMS (ES+, m/z): 535.02 [M+H]⁺; LCMS (ES−, m/z): 579.02 [M+HCOO⁻]⁻.

1.2. Compounds with R₁=NR'R" and R₂=OH

The compounds according to the invention can be synthesized according to the following reaction diagram:

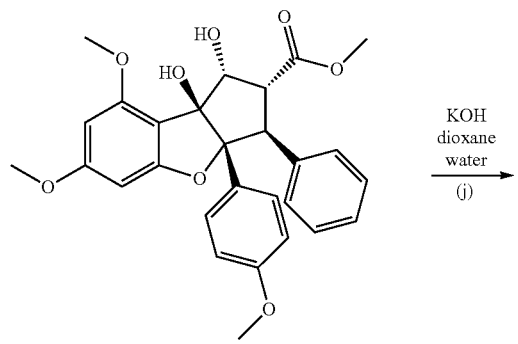

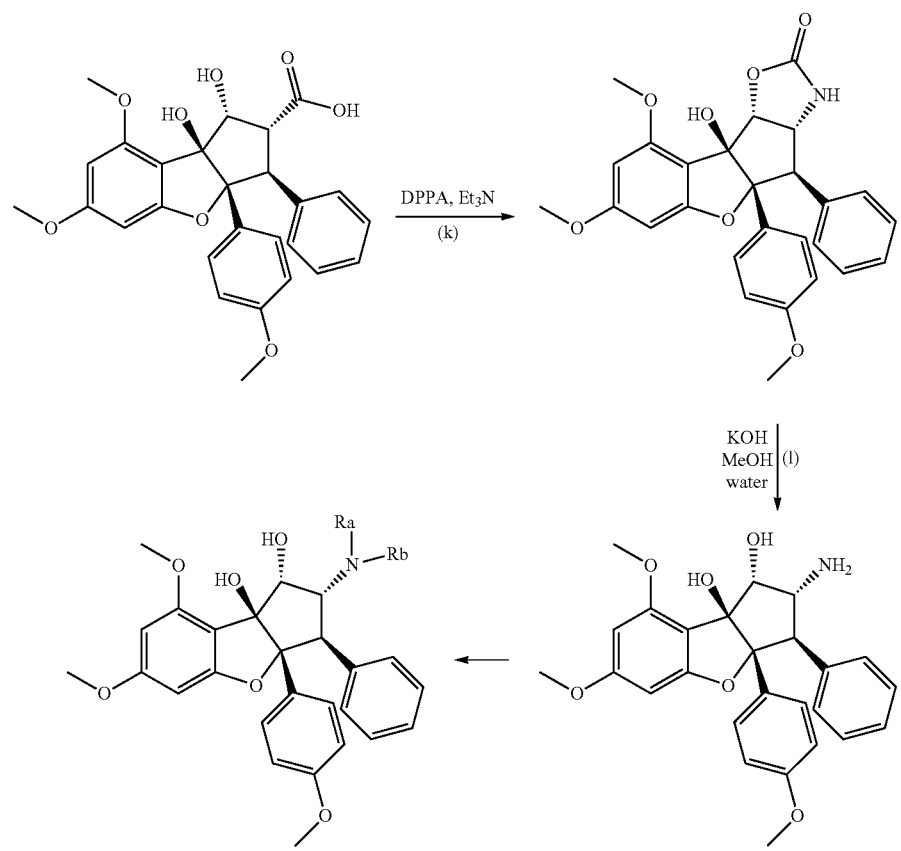

(j) Saponification procedure: In a 250 mL round-bottom flask, introduce rac-(1R,2R,3S,3aR,8bS)-methyl 1,8b-dihydroxy-6,8-dimethoxy-3a-(4-methoxyphenyl)-3-phenyl-2,3,3a,8b-tetrahydro-1H-cyclopenta[b]benzofuran-2-carboxylate (1.93 g, 3.92 mmol) in 24 mL of 1,4-dioxane. Prepare a solution of potassium hydroxide (0.930 g, 16.58 mmol) in water (3 mL) and add at 0° C. to the reaction mixture. Allow to return to room temperature and stir at 60° C. for 4 hours. Reduce the temperature of the mixture to 0° C. then add water (5 mL) and acidify the mixture with 1 N HCl solution until a pH of 5 is reached. Extract the product with ethyl acetate (twice). Dry the organic phase over $Na_2SO_4$, filter and concentrate the mixture. The acid is obtained in quantitative yield.

(k) Curtius rearrangement procedure: In a pill machine and under nitrogen, introduce carboxylic acid (200 mg, 0.418 mmol) in 10 mL of toluene. Add, at RT, diphenylphosphoryl azide (162 µL, 0.752 mmol) then triethylamine (58.1 µL, 0.418 mmol). Stir at 80° C. for 7 hours then stir at RT overnight. Concentrate the toluene. Take up the solid in water then rinse with ethyl acetate. The solid is not pure. Take up the solid in methanol, sonicate and filter. A white solid is collected. If the product does not precipitate, the residue is purified on silica gel.

(l) Oxazolidinone hydrolysis procedure: In a round-bottom flask, introduce rac-(3aR,4R,4aR,9bS,9cR)-9b-hydroxy-7,9-dimethoxy-4a-(4-methoxyphenyl)-4-phenyl-3,3a,4,4a,9b,9c-hexahydro-2H-benzofuro[3',2':3,4]cyclopenta[1,2-d]oxazol-2-one (1.45 g, 3.05 mmol) in 6 mL of methanol. Add room temperature KOH (1.027 g, 18.30 mmol) dissolved in water (3 mL). The mixture is heterogenous (suspended white solid). The reaction mixture is stirred at 75° C. for 72 hours. Evaporate the methanol then adjust the pH to 8 with saturated $NH_4Cl$ solution. A brown solid remains suspended. Filter it and rinse it with water then with diethyl ether; finally, dry it under vacuum to obtain the amine in 93% yield.

The compounds obtained by these various processes are characterized below.

Compound 9 rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol

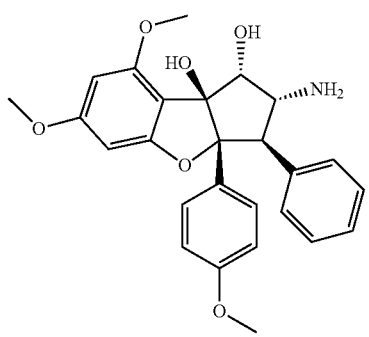 [SMILES: COc1ccc([C@@]23Oc4cc(OC)cc(OC)c4[C@]2(O)[C@H](O)[C@H](N)[C@H]3c2ccccc2)cc1]

White solid, 44 mg (93%); obtained from compound 40 by following the oxazolidinone hydrolysis procedure.

$^1$H NMR (DMSO-D$_6$, 400 MHz, δ, ppm): 7.04 (m, 7H), 6.58 (d, 2H, J=8.8 Hz), 6.21 (d, 1H, J=1.8 Hz), 6.08 (d, 1H, J=1.8 Hz), 4.82 (s, 1H), 4.16 (d, 1H J=4.7 Hz), 4.02 (dd, 1H, J=4.7 Hz, 13.0 Hz), 3.76 (s, 3H), 3.74 (s, 3H), 3.60 (s, 3H), 3.54 (d, 1H J=13.0 Hz); LCMS (ES+, m/z): 450.0 [M+H]$^+$; LCMS (ES−, m/z): 493.9 [M+HCOO$^-$]$^-$.

Compound 10 rac-N-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)formamide

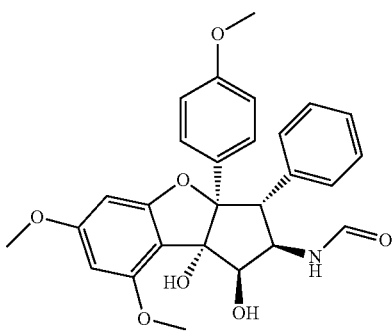 [SMILES: COc1ccc([C@@]23Oc4cc(OC)cc(OC)c4[C@]2(O)[C@H](O)[C@H](NC=O)[C@H]3c2ccccc2)cc1]

Pale yellow solid, 134 mg (84%); obtained from compound 9 as follows: In a round-bottom flask and under nitrogen, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (50 mg, 0.111 mmol) in 1 mL of THF, add ethyl formate (135 µL, 1.669 mmol) and a drop of acetic acid. Stir at reflux for 18 hours. The solvents are evaporated, the solid obtained is taken up in ethanol. A solid precipitates; filter it and rinse it with ethanol. After drying under vacuum, a light solid yellow is collected.

$^1$H NMR (DMSO-D$_6$, 400 MHz, δ, ppm): 8.00 (d, 1H, J=9.4 Hz), 7.96 (d, 1H, J=1.4 Hz), 7.01 (m, 7H), 6.60 (d, 2H, J=6.6 Hz), 6.25 (d, 1H, J=1.9 Hz), 6.10 (d, 1H, J=1.9 Hz), 5.19 (m, 1H), 5.10 (d, 1H, J=4.9 Hz), 5.04 (s, 1H), 4.27 (t, 1H, J=4.9 Hz), 3.93 (d, 1H, J=13.9 Hz), 3.77 (s, 3H), 3.73 (s, 3H), 3.60 (s, 3H); LCMS (ES+, m/z): 460.0 [M−OH]$^+$; LCMS (ES−, m/z): 522.1 [M+HCOO$^-$]$^-$.

Compound 11 rac-1-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)urea

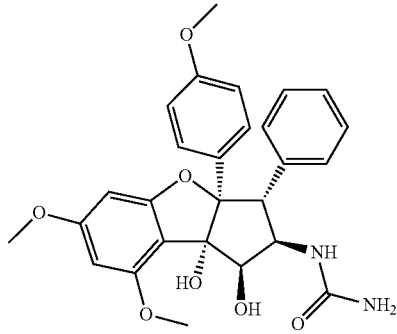 [SMILES: COc1ccc([C@@]23Oc4cc(OC)cc(OC)c4[C@]2(O)[C@H](O)[C@H](NC(N)=O)[C@H]3c2ccccc2)cc1]

White solid, 22 mg (50%); obtained from compound 9 as follows: In a round-bottom flask and under nitrogen, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (40 mg, 0.089 mmol) in a mixture of dichloromethane and propan-2-ol. Add, at room temperature, trimethylsilyl isocyanate (9.04 µL, 0.067 mmol). The mixture is clear. Stir at room temperature for 4 hours. Concentrate to dryness, take up the solid in a minimum volume of ethanol: filter the suspended solid. After drying, a white solid is collected.

$^1$H NMR (DMSO-D$_6$, 400 MHz, δ, ppm): 7.03 (m, 7H), 6.59 (d, 2H, J=8.8 Hz), 6.24 (d, 1H, J=1.7 Hz), 6.09 (d, 1H, J=1.7 Hz), 5.83 (d, 1H, J=9.5 Hz), 5.53 (s, 2H), 5.04 (m, 2H), 4.93 (s, 1H), 4.18 (m, 1H), 3.81 (m, 1H), 3.77 (s, 3H), 3.73 (s, 3H), 3.59 (s, 3H); LCMS (ES+, m/z): 492.9 [M+H]$^+$; LCMS (ES−, m/z): 536.9 [M+HCOO$^-$]$^-$.

Compound 12 rac-N-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)methanesulfonamide

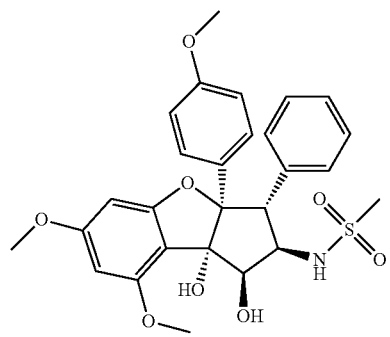

Pale yellow solid, 1.8 mg (3%); obtained from compound 9 as follows: In a round-bottom flask and under nitrogen, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (50 mg, 0.111 mmol) in 1.05 mL of dichloromethane, add, at 0° C., a mixture of N,N-diisopropylethylamine (DIEA, 29.1 µL, 0.167 mmol) and methanesulfonyl chloride (10.33 µL, 0.133 mmol). Stir at room temperature for 2 hours. Add 3 mL of 1 N HCl. Extract the organic phase then dry it over MgSO$_4$; filter and concentrate the mixture. Purify the residue on silica using as eluent a 100:0 to 90:10 DCM/AcOEt mixture.

$^1$H NMR (DMSO-D$_6$, 400 MHz, δ, ppm): 7.04 (m, 8H), 6.62 (m, 2H), 6.25 (m, 1H), 6.12 (m, 1H), 5.14 (m, 1H), 5.08 (s, 1H), 4.56 (m, 1H), 4.45 (m, 1H), 3.80 (m, 1H), 3.78 (s, 3H), 3.76 (s, 3H), 3.61 (s, 3H), 3.00 (s, 3H); LCMS (ES+, m/z): 509.9 [M−OH]$^+$; LCMS (ES−, m/z): 525.9 [M−H]$^−$.

Compound 13 rac-1-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)-3-methylthiourea

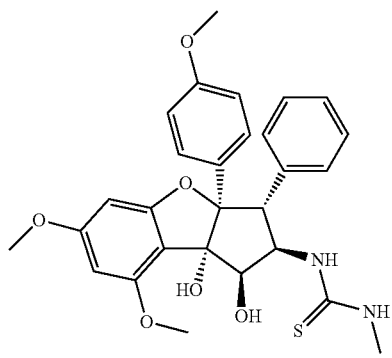

Beige solid, 33 mg (58%); obtained from compound 9 as follows: In a round-bottom flask, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (50 mg, 0.111 mmol) dissolved in tetrahydrofuran (2 mL). Add isothiocyanatomethane (9.76 mg, 0.133 mmol) and stir at room temperature for 2 hours. Concentrate the reaction mixture then add diethyl ether. Precipitation is observed. Filter the solid and rinse it with diethyl ether.

$^1$H NMR (DMSO-D$_6$, 400 MHz, δ, ppm): 7.06 (m, 9H), 6.25 (m, 1H), 6.09 (m, 1H), 5.04 (m, 1H), 4.92 (s, 1H), 4.34 (m, 1H), 3.77 (s, 3H), 3.72 (s, 3H), 3.60 (s, 3H), 2.53 (s, 3H); LCMS (ES+, m/z): 522.97 [M+H]$^+$; LCMS (ES−, m/z): 521.0 [M−H]$^−$.

Compound 14 rac-1-(3-(diethylamino)propyl)-3-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)thiourea

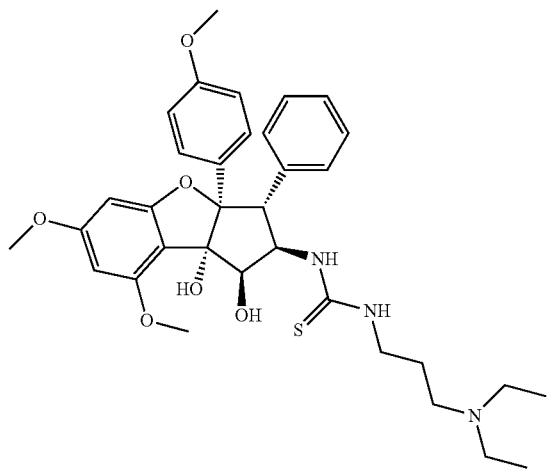 [SMILES: CCN(CC)CCCNC(=S)N[C@H]1[C@@H](O)[C@@]2(O)c3c(OC)cc(OC)cc3O[C@@]2(c2ccc(OC)cc2)[C@@H]1c1ccccc1]

Brown solid, 3.9 mg (5%); obtained from compound 9 by following a procedure identical to that for synthesizing compound 13 using N,N-diethyl-3-isothiocyanatopropan-1-amine instead of isothiocyanatomethane.

LCMS (ES+, m/z): 622.1 [M+H]$^+$; LCMS (ES−, m/z): 620.0 [M−H]$^−$.

Compound 15 rac-(1R,2R,3R,3aR,8bS)-6,8-dimethoxy-3a-(4-methoxyphenyl)-2-(methylamino)-3-phenyl-1,2,3,3a-tetrahydro-8bH-cyclopenta[b]benzofuran-1,8b-diol

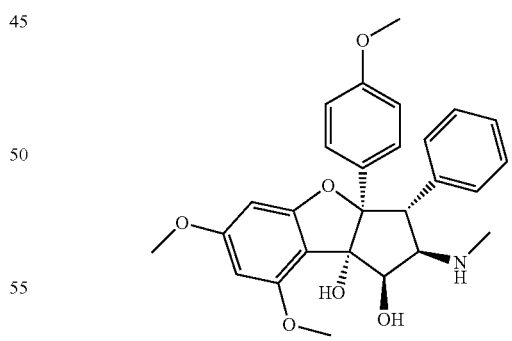

Brown solid, 3 mg (7%); obtained from compound 40 as follows: in a round-bottom flask and under nitrogen, introduce rac-(3aR,4R,4aR,9bS,9cR)-9b-hydroxy-7,9-dimethoxy-4a-(4-methoxyphenyl)-4-phenyl-3,3a,4,4a,9b,9c-hexahydro-2H-benzofuro[3',2':3,4]cyclopenta[1,2-d]oxazol-2-one (43.4 mg, 0.091 mmol) in 1 mL of THF, add, at 0° C., lithium aluminum hydride (15.31 µL, 0.365 mmol) and heat to 80° C. for 3 hours. Add at 0° C. 30 µL of water. Stir at room temperature for 5 minutes. Next add 30 µL of 10% NaOH then 100 μL of water. Stir at room temperature for 5 minutes. Filter on Dicalite® and rinse with THF and with ethyl acetate; concentrate the filtrate. The residue is purified on silica gel using as eluent a 100:0 to 80:20 DCM/MeOH mixture.

$^1$H NMR (CD$_3$OD, 400 MHz, δ, ppm): 7.14 (m, 2H), 7.05 (m, 3H), 6.93 (m, 2H), 6.63 (m, 2H), 6.23 (m, 1H), 6.16 (m, 1H), 4.65 (d, 1H), 3.85 (s, 3H), 3.83 (m, 1H), 3.81 (s, 3H), 3.67 (s, 3H), 3.63 (m, 1H), 2.46 (s, 3H); LCMS (ES+, m/z): 464.0 [M+H]$^+$; LCMS (ES−, m/z): 507.9 [M+HCOO$^-$]$^-$.

Compound 16 rac-N-((1R,2R,3R,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-yl)acetamide

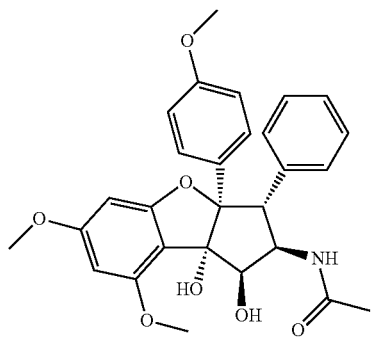 [SMILES: COc1ccc([C@@]23Oc4cc(OC)cc(OC)c4[C@]2(O)[C@H](O)[C@H](NC(C)=O)[C@H]3c2ccccc2)cc1]

Beige solid, 12 mg (23%); obtained from compound 9 as follows: In a round-bottom flask, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (50 mg, 0.111 mmol) dissolved in tetrahydrofuran (500 μL). Cool to 0° C. and add DIEA (38.9 μL, 0.222 mmol) and acetyl chloride (8.73 mg, 0.111 mmol), then allow to return to room temperature and stir for 4 hours. Add water and ethyl acetate, combine the organic phases and wash with saturated NaCl solution, then with water, dry the organic phase over Na$_2$SO$_4$ and concentrate. Triturate the crude product in diethyl ether and filter the solid.

LCMS (ES+, m/z): 491.9 [M+H]$^+$; LCMS (ES−, m/z): 535.9 [M+HCOO$^-$]$^-$.

Compound 17 rac-(1R,2R,3R,3aR,8bS)-2-amino-6-(4-aminobutoxy)-8-methoxy-3a-(4-methoxyphenyl)-3-phenyl-2,3,3a,8b-tetrahydro-1H-cyclopenta[b]benzofuran-1,8b-diol, di-formic Acid Salt

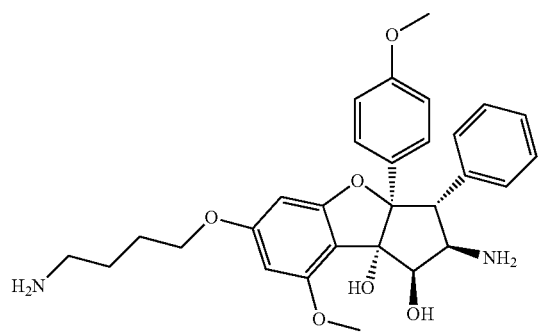 [SMILES: COc1ccc([C@@]23Oc4cc(OCCCCN)cc(OC)c4[C@]2(O)[C@H](O)[C@H](N)[C@H]3c2ccccc2)cc1]

White solid, 1.2 mg (3%); obtained from compound 43 by following the azide reduction then the oxazolidinone hydrolysis procedures.

$^1$H NMR (CD$_3$OD, 400 MHz, δ, ppm): 8.51 (bs, 2H), 7.12 (m, 5H), 6.90 (m, 2H), 6.68 (m, 2H, J=8.7 Hz), 6.28 (s, 1H), 6.20 (s, 1H), 4.74 (d, 1H, J=5.9 Hz), 4.39 (dd, 1H, J=5.9 Hz, 13.7 Hz), 4.06 (m, 2H), 3.89 (d, 1H, J=13.7 Hz), 3.87 (s, 3H), 3.69 (s, 3H), 3.02 (m, 2H), 1.88 (m, 4H); LCMS (ES+, m/z): 506.89 [M+H]$^+$; LCMS (ES−, m/z): 550.84 [M+HCOO$^-$]$^-$.

1.3. Compounds with R$_1$=Heterocycle and R$_2$=OH

The compounds according to the invention can be synthesized according to the following reaction diagram:

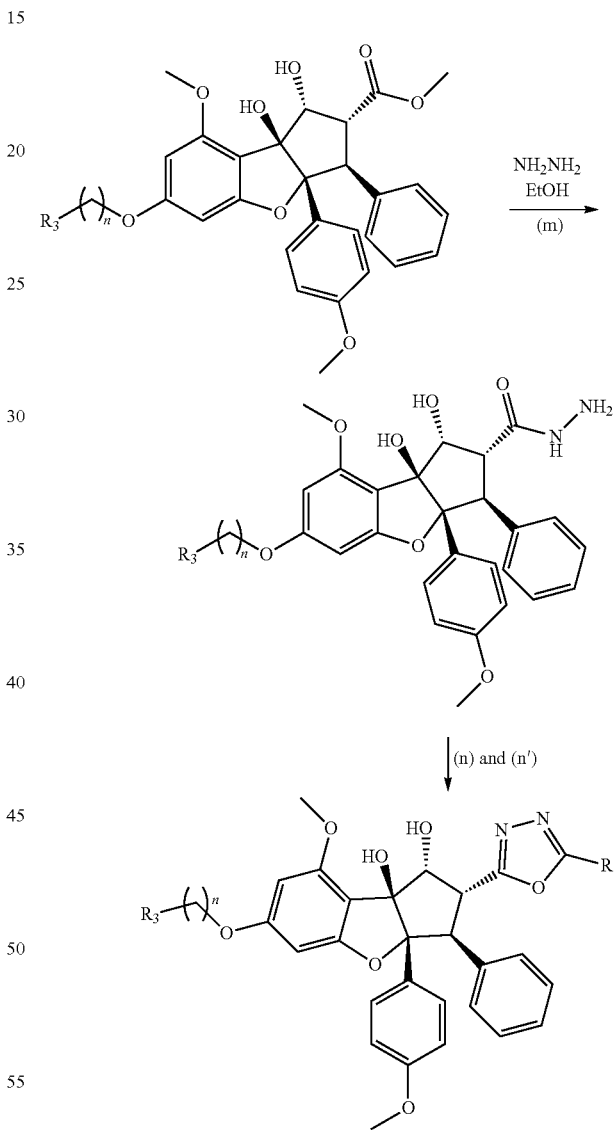

(m) Procedure for synthesizing the hydrazide (example n=1, R$_3$=H): In a sealed tube, introduce rac-(1R,2R,3S,3aR,8bS)-methyl 1,8b-dihydroxy-6,8-dimethoxy-3a-(4-methoxyphenyl)-3-phenyl-2,3,3a,8b-tetrahydro-1H-cyclopenta[b]benzofuran-2-carboxylate (2 g, 4.06 mmol) in 7 mL of ethanol. Add, at 0° C., hydrazine hydrate (1.275 mL, 40.6 mmol) then stir at 80° C. for 24 hours. Concentrate the mixture to dryness then take up the solid in ethanol. Filter the solid, rinse it with cold ethanol then dry it.

(n) Procedure for synthesizing the oxadiazole (example n=1, $R_3$=H, R=$NH_2$): In a round-bottom flask, introduce rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2 carbohydrazide (200 mg, 0.406 mmol) in 700 μL of 1,4-dioxane. Add, at room temperature, $NaHCO_3$ (34.1 mg, 0.406 mmol) and water (70 μL). A 0° C., add cyanogen bromide (162 μL, 0.487 mmol) then at room temperature for 5 hours. After concentrating the mixture, add water and sonicate; a solid is suspended. Dissolve the solid in ethyl acetate. Extract the organic phase and wash it with saturated $NaHCO_3$ solution. Dry the organic phase over $Na_2SO_4$, filter then concentrate. Purify the residue on silica gel using as eluent 100:0 to 95:5 DCM/MeOH.

(n') Procedure for synthesizing substituted amino-oxadiazoles (example n=1, $R_3$=H, R=NHMe): To a solution of rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide (40 mg, 0.081 mmol) in tetrahydrofuran (1.5 mL) is added isothiocyanatomethane (7.54 mg, 0.103 mmol) then 1-(3-dimethylaminopropyl)-3-ethylcarbodiimide hydrochloride (15.57 mg, 0.081 mmol) at 0° C. The mixture is stirred at 80° C. for 18 hours. The reaction mixture is concentrated and the residue obtained is purified on silica gel using as eluent a 100:0 to 97:3 DCM/MeOH mixture.

Compound 18 rac-(1R,2R,3S,3aR,8bS)-2-(5-amino-1,3,4-oxadiazol-2-yl)-6,8-dimethoxy-3a-(4-methoxyphenyl)-3-phenyl-2,3,3a,8b-tetrahydro-1H-cyclopenta[b]benzofuran-1,8b-diol

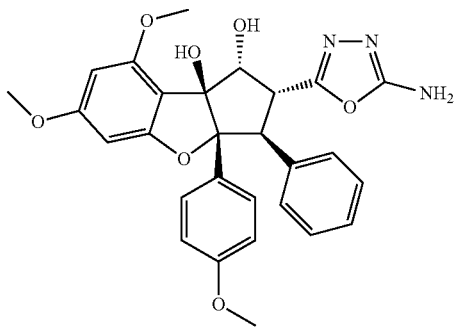 [SMILES: COc1ccc([C@@]23Oc4cc(OC)cc(OC)c4[C@]2(O)[C@H](O)[C@H](c2nnc(N)o2)[C@H]3c2ccccc2)cc1]

White solid, 99 mg (47%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide by following the procedure for synthesizing the oxadiazole.

$^1$H NMR (DMSO-$D_6$, 400 MHz, δ, ppm): 7.02 (m, 5H), 6.86 (m, 2H), 6.73 (s, 2H), 6.60 (d, 2H, J=8.9 Hz), 6.28 (d, 1H, J=1.8 Hz), 6.11 (d, 1H, J=1.8 Hz), 5.16 (s, 1H), 4.99 (d, 1H, J=4.4 Hz), 4.61 (m, 1H), 4.26 (m, 2H), 3.78 (s, 3H), 3.72 (s, 3H), 3.60 (s, 3H); LCMS (ES+, m/z): 518.0 [M+H]$^+$; LCMS (ES-, m/z): 516.0 [M-H]$^-$.

Compound 19

(1R,2R,3S,3aR,8bS)-2-(5-amino-1,3,4-oxadiazol-2-yl)-6,8-dimethoxy-3a-(4-methoxyphenyl)-3-phenyl-2,3,3a,8b-tetrahydro-1H-cyclopenta[b]benzofuran-1,8b-diol

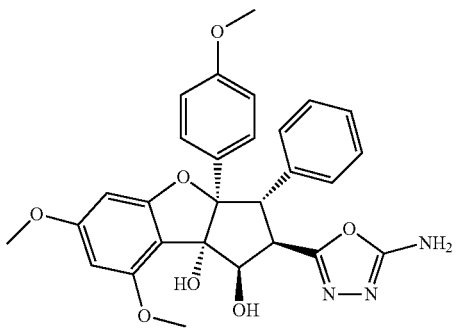 [SMILES: COc1ccc([C@@]23Oc4cc(OC)cc(OC)c4[C@]2(O)[C@H](O)[C@H](c2nnc(N)o2)[C@H]3c2ccccc2)cc1]

White solid, 205 mg (41%); obtained from compound 18 by chiral separation on HPLC using a Chiralpak® IC 4.6×250 mm DAICEL column and as eluent an 80:10:10: 0.05 heptane/ethanol/methanol/diethylamine mixture.

LCMS (ES+, m/z): 518.0 [M+H]$^+$; LCMS (ES-, m/z): 516.0 [M-H]$^-$ e.e. 96.7%; $[α]_D^{20}$=-27.7 (c 0.59 MeOH)

Compound 20 rac-(1R,2R,3S,3aR,8bS)-2-(5-amino-1,3,4-oxadiazol-2-yl)-6-(2-hydroxyethoxy)-8-methoxy-3a-(4-methoxyphenyl)-3-phenyl-2,3,3a,8b-tetrahydro-1H-cyclopenta[b]benzofuran-1,8b-diol

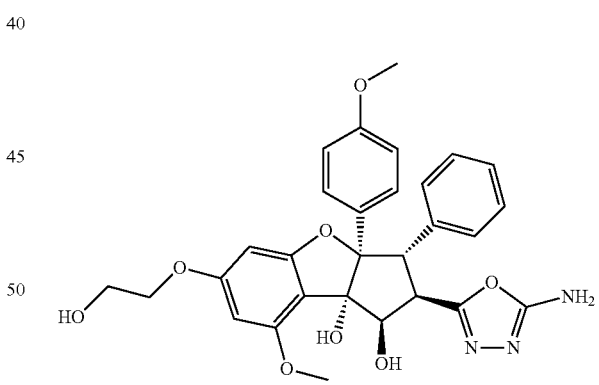

White solid, 51 mg (51%); obtained from the compound rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol with prop-2-en-1-ol, for synthesizing the hydrazide, for forming the oxadiazole, for dihydroxylation, for oxidative cleavage and finally for reduction of the aldehyde.

$^1$H NMR (DMSO-$D_6$, 400 MHz, δ, ppm): 7.03 (m, 5H), 6.87 (m, 2H), 6.74 (s, 2H), 6.61 (d, 2H, J=8.8 Hz), 6.28 (m, 1H), 6.12 (m, 1H), 5.17 (s, 1H), 5.01 (d, 1H, J=4.4 Hz), 4.88 (t, 1H, J=5.5 Hz), 4.61 (m, 1H), 4.27 (m, 2H), 4.01 (m, 2H), 3.73 (m, 2H+3H), 3.61 (s, 3H); LCMS (ES+, m/z): 548 [M+H]⁺; LCMS (ES−, m/z): 592 [M+HCOO⁻]⁻.

Compound 21 rac-(1R,2R,3S,3aR,8bS)-2-(5-amino-1,3,4-oxadiazol-2-yl)-6-(2-(dimethylamino)ethoxy)-8-methoxy-3a-(4-methoxyphenyl)-3-phenyl-2,3,3a,8b-tetrahydro-1H-cyclopenta[b]benzofuran-1,8b-diol

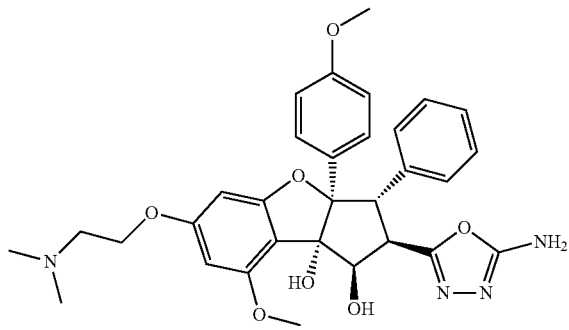 [SMILES: COc1ccc([C@@]23Oc4cc(OCCN(C)C)cc(OC)c4[C@]2(O)[C@H](O)[C@H](c2nnc(N)o2)[C@H]3c2ccccc2)cc1]

White solid; obtained from the compound rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol with prop-2-en-1-ol, for synthesizing the hydrazide, for forming the oxadiazole, for dihydroxylation, for oxidative cleavage and finally for reductive amination using dimethylamine.

¹H NMR (DMSO-D₆, 400 MHz, δ, ppm): 7.03 (m, 5H), 6.87 (m, 2H), 6.74 (s, 2H), 6.61 (d, 2H, J=8.9 Hz), 6.29 (m, 1H), 6.11 (m, 1H), 5.17 (s, 1H), 5.00 (d, 1H, J=4.3 Hz), 4.61 (m, 1H), 4.27 (s, 2H), 3.73 (s, 3H), 3.61 (s, 3H), 2.63 (m, 2H), 2.23 (s, 6H); LCMS (ES+, m/z): 575.01 [M+H]⁺; LCMS (ES−, m/z): 572.94 [M−H]⁻.

Compound 22 rac-(1R,2R,3S,3aR,8bS)-2-(5-amino-1,3,4-oxadiazol-2-yl)-8-methoxy-3a-(4-methoxyphenyl)-6-(2-(4-methylpiperazin-1-yl)ethoxy)-3-phenyl-2,3,3a,8b-tetrahydro-1H-cyclopenta[b]benzofuran-1,8b-diol

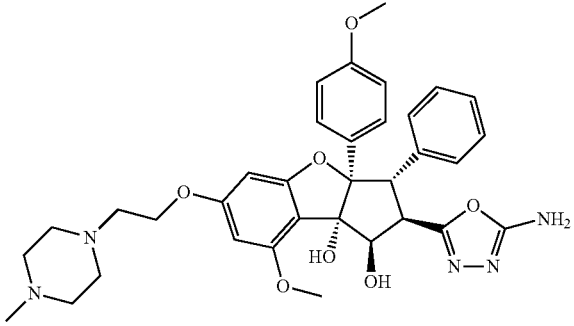 [SMILES: COc1ccc([C@@]23Oc4cc(OCCN5CCN(C)CC5)cc(OC)c4[C@]2(O)[C@H](O)[C@H](c2nnc(N)o2)[C@H]3c2ccccc2)cc1]

White solid, 56 mg (24%); obtained from the compound rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol with prop-2-en-1-ol, for synthesizing the hydrazide, for forming the oxadiazole, for dihydroxylation, for oxidative cleavage and finally for reductive amination using 1-methylpiperazine.

¹H NMR (DMSO-D₆, 400 MHz, δ, ppm): 7.03 (m, 5H), 6.87 (m, 2H), 6.74 (s, 2H), 6.61 (m, 2H), 6.29 (s, 1H), 6.12 (s, 1H), 5.17 (s, 1H), 5.01 (m, 1H), 4.61 (m, 1H), 4.26 (s, 2H), 4.10 (m, 2H), 3.73 (s, 3H), 3.61 (s, 3H), 2.50 (m, 8H), 2.16 (s, 3H); LCMS (ES+, m/z): 630.07 [M+H]⁺; LCMS (ES−, m/z): 674.00 [M+HCOO⁻]⁻.

Compound 23 rac-(1R,2R,3S,3aR,8bS)-2-(5-amino-1,3,4-oxadiazol-2-yl)-8-methoxy-3a-(4-methoxyphenyl)-6-(2-morpholinoethoxy)-3-phenyl-2,3,3a,8b-tetrahydro-1H-cyclopenta[b]benzofuran-1,8b-diol

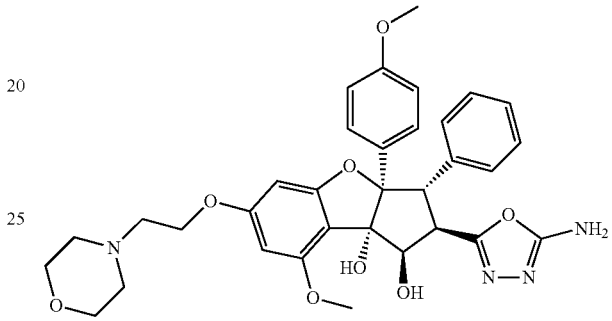

White solid, 60 mg (26%); obtained from the compound rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol with prop-2-en-1-ol, for synthesizing the hydrazide, for forming the oxadiazole, for dihydroxylation, for oxidative cleavage and finally for reductive amination using morpholine.

¹H NMR (DMSO-D₆, 400 MHz, δ, ppm): 7.03 (m, 5H), 6.87 (m, 2H), 6.74 (s, 2H), 6.61 (m, 2H), 6.29 (s, 1H), 6.12 (s, 1H), 5.17 (s, 1H), 5.01 (m, 1H), 4.61 (m, 1H), 4.26 (s, 2H), 4.12 (m, 2H), 3.73 (s, 3H), 3.60 (m, 7H), 2.70 (m, 4H), 2.50 (m, 4H); LCMS (ES+, m/z): 616.98 [M+H]⁺; LCMS (ES−, m/z): 660.87 [M+HCOO⁻]⁻.

Compound 24 rac-(1R,2R,3S,3aR,8bS)-6,8-dimethoxy-3a-(4-methoxyphenyl)-2-(5-(methylamino)-1,3,4-oxadiazol-2-yl)-3-phenyl-2,3,3a,8b-tetrahydro-1H-cyclopenta[b]benzofuran-1,8b-diol

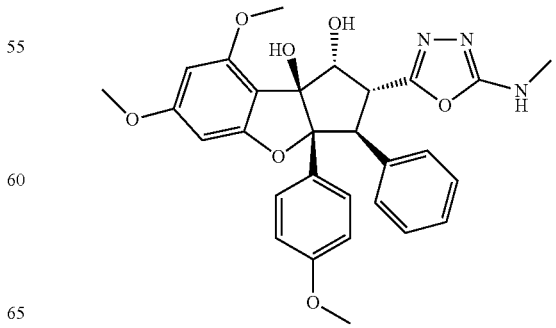

White solid, 100 mg (30%); obtained from the rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide described above and by applying the procedure for synthesizing substituted amino-oxadiazoles using isothiocyanatomethane.

¹H NMR (DMSO-D₆, 400 MHz, δ, ppm): 7.14 (q, 1H, J=5.0 Hz), 7.03 (m, 5H), 6.87 (m, 2H), 6.61 (d, 2H, J=8.9 Hz), 6.29 (d, 1H, J=1.8 Hz), 6.12 (d, 1H, J=1.8 Hz), 5.17 (s, 1H), 5.01 (d, 1H, J=4.3 Hz), 4.61 (m, 1H), 4.27 (m, 2H), 3.78 (s, 3H), 3.73 (s, 3H), 3.61 (s, 3H), 2.66 (d, 3H, J=5.0 Hz); LCMS (ES+, m/z): 532 [M+H]⁺; LCMS (ES−, m/z): 576 [M+HCOO⁻]⁻.

Compound 25 rac-(1R,2R,3S,3aR,8bS)-6,8-dimethoxy-3a-(4-methoxyphenyl)-3-phenyl-2-(5-(propylamino)-1,3,4-oxadiazol-2-yl)-2,3,3a,8b-tetrahydro-1H-cyclopenta[b]benzofuran-1,8b-diol

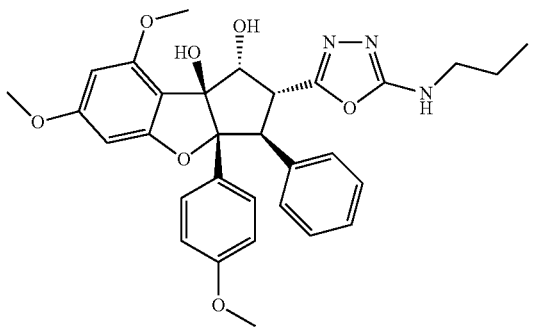 [SMILES: CCCNc1nnc([C@H]2[C@@H](O)[C@@]3(O)c4c(OC)cc(OC)cc4O[C@@]3(c3ccc(OC)cc3)[C@@H]2c2ccccc2)o1]

White solid, 63 mg (37%); obtained from the rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide described above and by applying the procedure for synthesizing substituted amino-oxadiazoles using 1-isothiocyanatopropane.

¹H NMR (DMSO-D₆, 400 MHz, δ, ppm): 7.25 (t, 1H, J=5.8 Hz), 7.03 (m, 5H), 6.87 (m, 2H), 6.61 (d, 2H, J=8.9 Hz), 6.29 (d, 1H, J=1.9 Hz), 6.12 (d, 1H, J=1.9 Hz), 5.17 (bs, 1H), 5.01 (bs, 1H), 4.62 (bs, 1H), 4.27 (m, 2H), 3.10 (s, 3H), 3.73 (s, 3H), 3.61 (s, 3H), 2.98 (m, 2H), 1.43 (hex., 2H, J=7.2 Hz), 0.8 (t, 3H, J=7.2 Hz); LCMS (ES+, m/z): 560.1 [M+H]⁺; LCMS (ES−, m/z): 604.1 [M+HCOO⁻]⁻.

Compound 26 rac-(1R,2R,3S,3aR,8bS)-2-(5-((3-(diethylamino)propyl)amino)-1,3,4-oxadiazol-2-yl)-6,8-dimethoxy-3a-(4-methoxyphenyl)-3-phenyl-2,3,3a,8b-tetrahydro-1H-cyclopenta[b]benzofuran-1,8b-diol

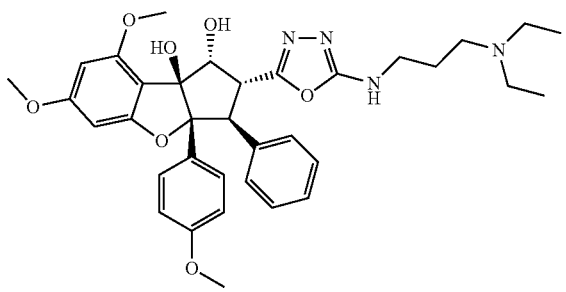 [SMILES: CCN(CC)CCCNc1nnc([C@H]2[C@@H](O)[C@@]3(O)c4c(OC)cc(OC)cc4O[C@@]3(c3ccc(OC)cc3)[C@@H]2c2ccccc2)o1]

Beige solid, 2.8 mg (5%); obtained from the rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide described above and by applying the procedure for synthesizing substituted amino-oxadiazoles using N,N-diethyl-3-isothiocyanatopropan-1-amine.

LCMS (ES+, m/z): 631.1 [M+H]⁺; LCMS (ES−, m/z): 663.1 [M+HCOO⁻]⁻

Compound 27 rac-(1R,2R,3S,3aR,8bS)-2-(5-hydroxy-1,3,4-oxadiazol-2-yl)-6,8-dimethoxy-3a-(4-methoxyphenyl)-3-phenyl-2,3,3a,8b-tetrahydro-1H-cyclopenta[b]benzofuran-1,8b-diol

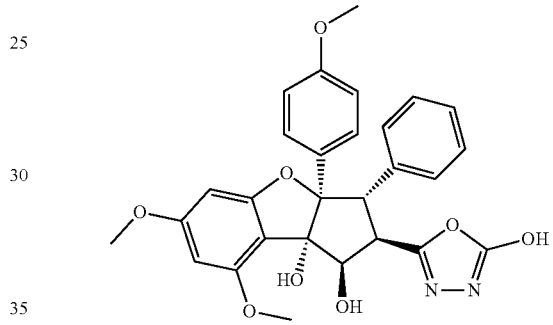

White solid, 82 mg (65%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide as follows: In a round-bottom flask and under nitrogen, introduce rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide (40 mg, 0.081 mmol) in 0.4 mL of tetrahydrofuran then Et₃N (23.66 µL, 0.170 mmol). Add, at room temperature, 1,1'-carbonyldiimidazole (16.33 mg, 0.101 mmol). Stir at room temperature for 18 hours. Dilute the mixture with ethyl acetate. Wash with 1 N HCl solution then with saturated NaCl solution. Dry the organic phase over MgSO₄, filter then concentrate. A white solid is collected.

¹H NMR (DMSO-D₆, 400 MHz, δ, ppm): 11.92 (s, 1H), 7.00 (m, 7H), 6.59 (d, 2H, J=8.9 Hz), 6.28 (d, 1H, J=1.9 Hz), 6.11 (d, 1H, J=1.9 Hz), 5.17 (m, 2H), 4.63 (m, 1H), 4.20 (m, 2H), 3.78 (s, 3H), 3.73 (s, 3H), 3.60 (s, 3H); LCMS (ES+, m/z): 501.0 [M−OH]⁺; LCMS (ES−, m/z): 517.0 [M−H]⁻.

Compound 28 rac-(1R,2R,3S,3aR,8bS)-2-(5-mercapto-1,3,4-oxadiazol-2-yl)-6,8-dimethoxy-3a-(4-methoxyphenyl)-3-phenyl-2,3,3a,8b-tetrahydro-1H-cyclopenta[b]benzofuran-1,8b-diol

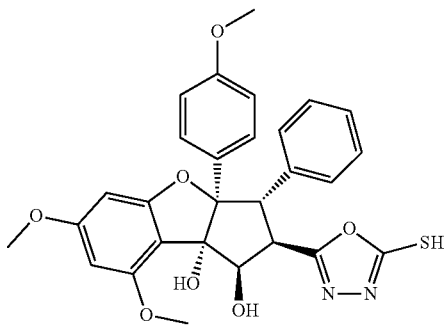 [SMILES: COc1ccc([C@@]23Oc4cc(OC)cc(OC)c4[C@]2(O)[C@H](O)[C@H](c2nnc(O)o2)[C@H]3c2ccccc2)cc1]

White solid, 26 mg (49%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide as follows: In a round-bottom flask, introduce rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide (50 mg, 0.102 mmol) in ethanol (1 mL). Add KOH (17.09 mg, 0.305 mmol) and $CS_2$ (12.24 µL, 0.203 mmol) and heat to 90° C. for 1 hour. Concentrate the reaction mixture and take it up in ethyl acetate and in water. Add saturated $NaHCO_3$ solution to the aqueous phase and extract again with ethyl acetate. Combine the organic phases and wash them with saturated NaCl solution then dry them over $Na_2SO_4$ and concentrate. The residue is purified on silica gel using as eluent a 98:2 DCM/MeOH mixture.

$^1$H NMR (DMSO-$D_6$, 400 MHz, δ, ppm): 14.19 (s, 1H), 7.01 (m, 7H), 6.59 (d, 2H, J=9.0 Hz), 6.28 (d, 1H, J=1.9 Hz), 6.11 (d, 1H, J=1.9 Hz), 5.26 (d, 1H, J=4.6 Hz), 5.22 (s, 1H), 4.67 (t, 1H, J=4.6 Hz), 4.43 (dd, 1H, J=4.6 Hz, 14.1 Hz), 4.25 (d, 1H, J=14.1 Hz), 3.77 (s, 3H), 3.72 (s, 3H), 3.60 (s, 3H); LCMS (ES+, m/z): 535.0 [M+H]$^+$; LCMS (ES−, m/z): 532.9 [M−H]$^−$.

Compound 29 rac-(1R,2S,3S,3aR,8bS)-2-(5-amino-4H-1,2,4-triazol-3-yl)-6,8-dimethoxy-3a-(4-methoxyphenyl)-3-phenyl-2,3,3a,8b-tetrahydro-1H-cyclopenta[b]benzofuran-1,8b-diol

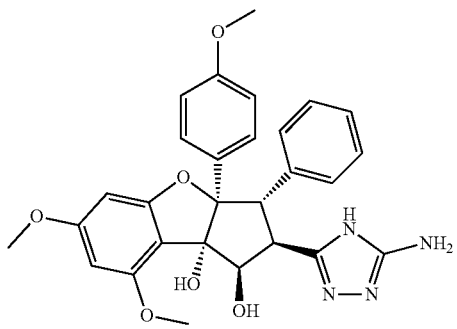 [SMILES: COc1ccc([C@@]23Oc4cc(OC)cc(OC)c4[C@]2(O)[C@H](O)[C@H](c2nnc(N)[nH]2)[C@H]3c2ccccc2)cc1]

White solid, 1 mg (2%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide as follows: To a solution of rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide (50 mg, 0.102 mmol) in water (0.6 mL) is added 2-methylisothiourea (9.15 mg, 0.102 mmol) then sodium hydroxide (6.09 mg, 0.152 mmol) at 0° C. The mixture is stirred at 75° C. for 5 hours. The crude product is purified by preparative HPLC.

$^1$H NMR (DMSO-$D_6$, 400 MHz, δ, ppm): 7.05 (m, 2H), 6.96 (m, 4H), 6.90 (m, 1H), 6.57 (m, 2H), 6.24 (m, 1H), 6.08 (m, 1H), 5.60 (bs, 2H), 4.95 (m, 3H), 4.40 (m, 1H), 4.34 (m, 1H), 4.11 (m, 1H), 3.76 (s, 3H), 3.70 (s, 3H), 3.58 (s, 3H); HRMS: C28H29N4O6 [M+H]$^+$ calc. 517.2082 found 517.2060.

Compound 30 rac-(1R,2S,3S,3aR,8bS)-6,8-dimethoxy-3a-(4-methoxyphenyl)-2-(5-methyl-4H-1,2,4-triazol-3-yl)-3-phenyl-2,3,3a,8b-tetrahydro-1H-cyclopenta[b]benzofuran-1,8b-diol

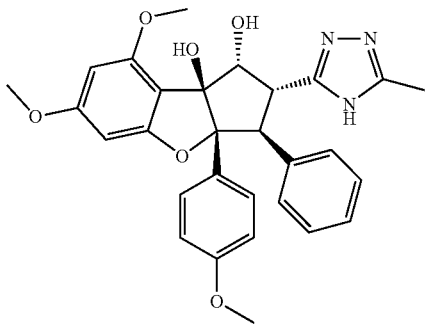

White solid, 59 mg (37%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide as follows: To a solution of ethyl acetamidate hydrochloric acid salt (301 mg, 2.436 mmol) in acetonitrile (16 mL) is added triethylamine (849 µL, 6.09 mmol) then rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carbohydrazide (600 mg, 1.218 mmol). The mixture is stirred at 90° C. for 48 hours. Concentrate the reaction mixture and purify the residue on silica gel using as eluent a 98:2 DCM/MeOH mixture.

$^1$H NMR (CDCl$_3$, 400 MHz, δ, ppm): 7.19 (d, 2H, J=8.9 Hz), 7.00 (m, 5H), 6.65 (d, 2H, J=8.9 Hz), 6.29 (d, 1H, J=1.9 Hz), 6.13 (d, 1H, J=1.9 Hz), 4.91 (d, 1H, J=5.0 Hz), 4.51 (dd, 1H, J=5.0 Hz, 14.1 Hz), 4.37 (d, 1H, J=14.1 Hz), 3.86 (s, 3H), 3.84 (s, 3H), 3.70 (s, 3H), 3.07 (m, 1H), 2.32 (s, 3H); LCMS (ES+, m/z): 516.0 [M+H]$^+$; LCMS (ES−, m/z): 513.9 [M−H]$^−$.

Compound 31 rac-(1R,2R,3S,3aR,8bS)-2-(3-isopropyl-1,2,4-oxadiazol-5-yl)-6,8-dimethoxy-3a-(4-methoxyphenyl)-3-phenyl-2,3,3a,8b-tetrahydro-1H-cyclopenta[b]benzofuran-1,8b-diol

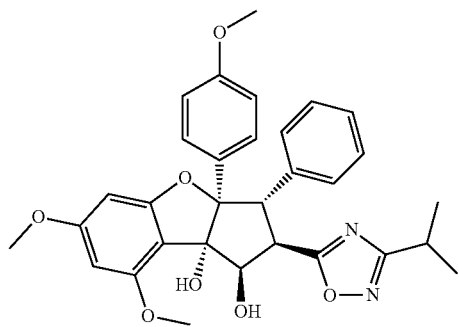 [SMILES: COc1ccc([C@@]23Oc4cc(OC)cc(OC)c4[C@]2(O)[C@H](O)[C@H](c2nc(C(C)C)no2)[C@H]3c2ccccc2)cc1]

White solid, 6.4 mg (11%); obtained from the compound rac-(1R,2R,3S,3aR,8bS)-methyl 1,8b-dihydroxy-6,8-dimethoxy-3a-(4-methoxyphenyl)-3-phenyl-2,3,3a,8b-tetrahydro-1H-cyclopenta[b]benzofuran-2-carboxylate as follows: In a round-bottom flask and under nitrogen, introduce rac-(1R,2R,3S,3aR,8bS)-methyl 1,8b-dihydroxy-6,8-dimethoxy-3a-(4-methoxyphenyl)-3-phenyl-2,3,3a,8b-tetrahydro-1H-cyclopenta[b]benzofuran-2-carboxylate (50 mg, 0.102 mmol) in 0.5 mL of toluene. The mixture is clear. Add, at room temperature, (Z)—N'-hydroxyisobutyrimidamide (11.41 mg, 0.112 mmol) then $K_2CO_3$ (15.43 mg, 0.112 mmol). Stir at reflux. After 4 hours, very little product forms. Heat at reflux for 18 hours. Dilute the mixture with ethyl acetate then wash with water. Dry the organic phase over $MgSO_4$, filter then concentrate. Purify the residue on silica using as eluent 95:5 DCM/MeOH.

$^1$H NMR (DMSO-$D_6$, 400 MHz, δ, ppm): 7.11 (d, 2H, J=8.9 Hz), 7.01 (m, 3H), 6.86 (m, 2H), 6.61 (d, 2H, J=8.9 Hz), 6.30 (d, 1H, J=1.7 Hz), 6.11 (d, 1H, J=1.7 Hz), 5.24 (s, 1H), 5.14 (m, 1H), 4.71 (m, 1H), 4.59 (dd, 1H, J=5.1 Hz, 14.2 Hz), 4.41 (d, 1H, J=14.2 Hz), 3.78 (s, 3H), 3.71 (s, 3H), 3.61 (s, 3H), 2.91 (hept., 1H, J=6.9 Hz), 1.15 (d, 6H, J=6.9 Hz); LCMS (ES+, m/z): 545.0 [M+H]$^+$; LCMS (ES−, m/z): 588.9 [M+HCOO$^-$]$^-$.

1.4. Compounds with $R_1$ and $R_2$ Forming a Heterocycle

The compounds according to the invention can be synthesized according to the following reaction diagram:

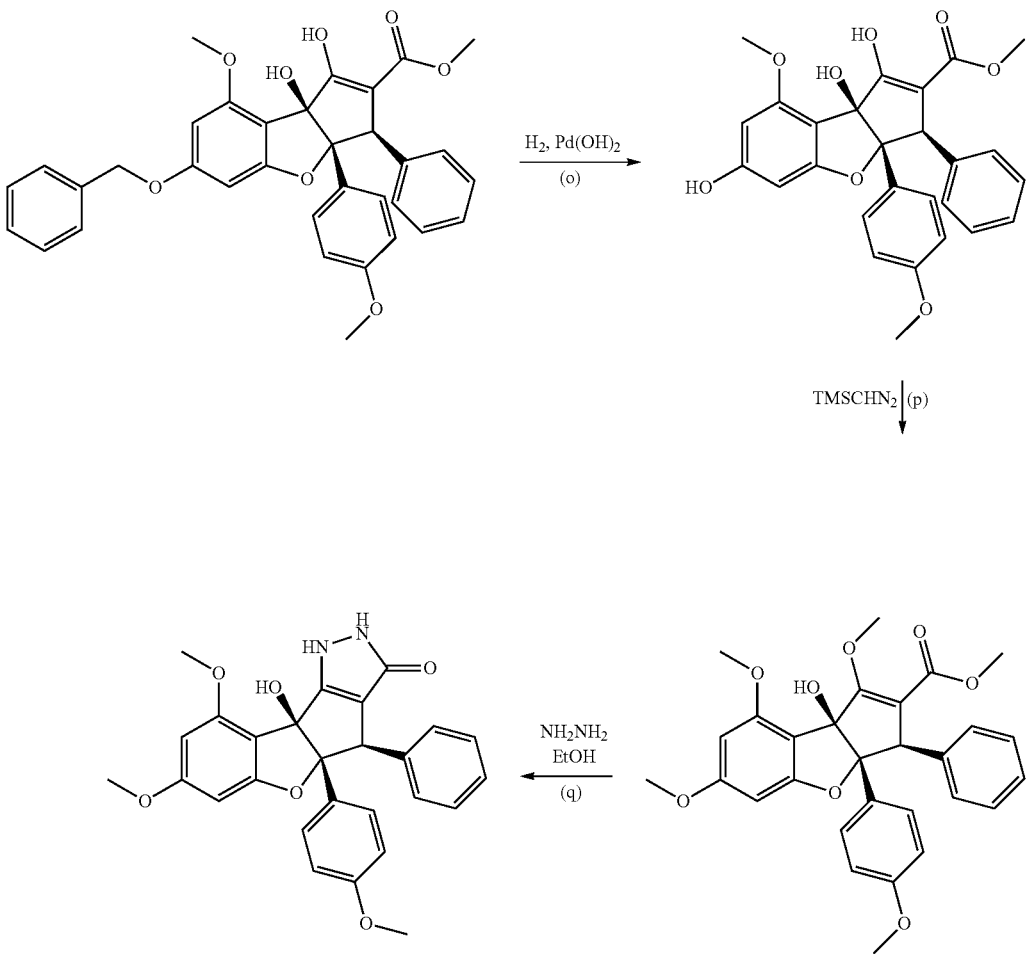

(o) Procedure for deprotection of the phenol: To rac-methyl (3R,3aR,8bS)-6-(benzyloxy)-1,8b-dihydroxy-8-methoxy-3a-(4-methoxyphenyl)-3-phenyl-3a,8b-dihydro-3H-cyclopenta[b]benzofuran-2-carboxylate (inter-1 described in: Journal of the American Chemical Society, 2009, 131, 1607-1616) (1 g, 1.765 mmol) in ethyl acetate (10 mL) degassed with nitrogen is added palladium hydroxide. The mixture is then stirred under hydrogen pressure (1 bar) for 18 hours at room temperature. The palladium is filtered on Celite® and rinsed with ethyl acetate then an 80:20 to 10:90 $CH_2Cl_2$/MeOH mixture. The filtrate is evaporated and the residue obtained (inter-2) is used without further purification.

(p) Procedure for methylation of the phenol: In a 100 mL Heck flask introduce the compound previously obtained (0.869 g, 1.824 mmol), add the solvents (10 mL of MeOH and 5 mL of toluene). Add dropwise trimethylsilyl diazomethane solution (2 M in hexane), stopper the flask and stir at room temperature for 18 hours. Take up several times in dichloromethane and acetonitrile then evaporate to obtain a homogeneous foam. Purify the residue on silica gel using as eluent 100:0 to 80:20 DCM/AcOEt to obtain rac-methyl (3R,3aR,8bS)-8b-hydroxy-1,6,8-trimethoxy-3a-(4-methoxyphenyl)-3-phenyl-3a,8b-dihydro-3H-cyclopenta[b]benzofuran-2-carboxylate in the form of a white solid (inter-3, 540 mg, 58% in 2 steps).

$^1$H NMR (CDCl$_3$, 400 MHz, δ, ppm): 7.10 (m, 5H), 6.98 (m, 2H), 6.57 (d, 2H, J=8.9 Hz), 6.22 (d, 1H, J=1.9 Hz), 6.06 (d, 1H, J=1.9 Hz), 4.51 (s, 1H), 4.19 (s, 3H), 3.83 (s, 3H), 3.82 (s, 3H), 3.68 (s, 3H), 3.52 (s, 3H); LCMS (ES+, m/z): 487.25 [M-OH]$^+$; LCMS (ES-, m/z): 549.32 [M+HCOO$^-$]$^-$.

(q) Procedure for forming the pyrazolone ring: In a microwave flask fitted with a magnetic bar are added the compound obtained previously (0.250 g, 0.496 mmol), ethanol (4 mL) then hydrazine monohydrate (2.070 mL, 27.3 mmol). The stoppered flask is placed in a microwave device and the reaction mixture is subjected to two 1-minute heating cycles at 180° C. After evaporation to dryness, take up the solid in a minimum of methanol, filter the solid and dry under vacuum.

Compound 32 rac-(4R,4aR,9bS)-9b-hydroxy-7,9-dimethoxy-4a-(4-methoxyphenyl)-4-phenyl-1,2,4,4a-tetrahydrobenzofuro[2',3':4,5]cyclopenta[1,2-c]pyrazol-3(9bH)-one

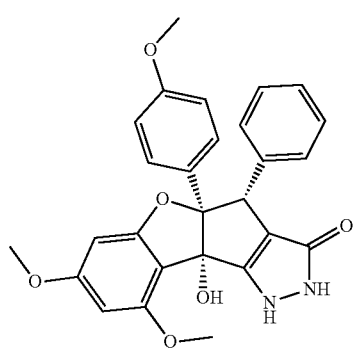 [SMILES: COc1ccc([C@@]23Oc4cc(OC)cc(OC)c4[C@]2(O)c2[nH][nH]c(=O)c2[C@H]3c2ccccc2)cc1]

Beige solid, 136 mg (58%); obtained according to the procedure described above.

$^1$H NMR (DMSO-D$_6$, 400 MHz, δ, ppm): 11.73 (bs, 1H), 9.53 (bs, 1H), 7.06 (m, 4H), 6.98 (m, 3H), 6.37 (d, 1H, J=1.9 Hz), 6.14 (d, 1H, J=1.9 Hz), 5.41 (bs, 1H), 4.21 (s, 1H), 3.78 (s, 6H), 3.57 (s, 3H); LCMS (ES+, m/z): 473.18 [M+H]$^+$.

The compounds according to the invention can also be synthesized according to the following reaction diagram:

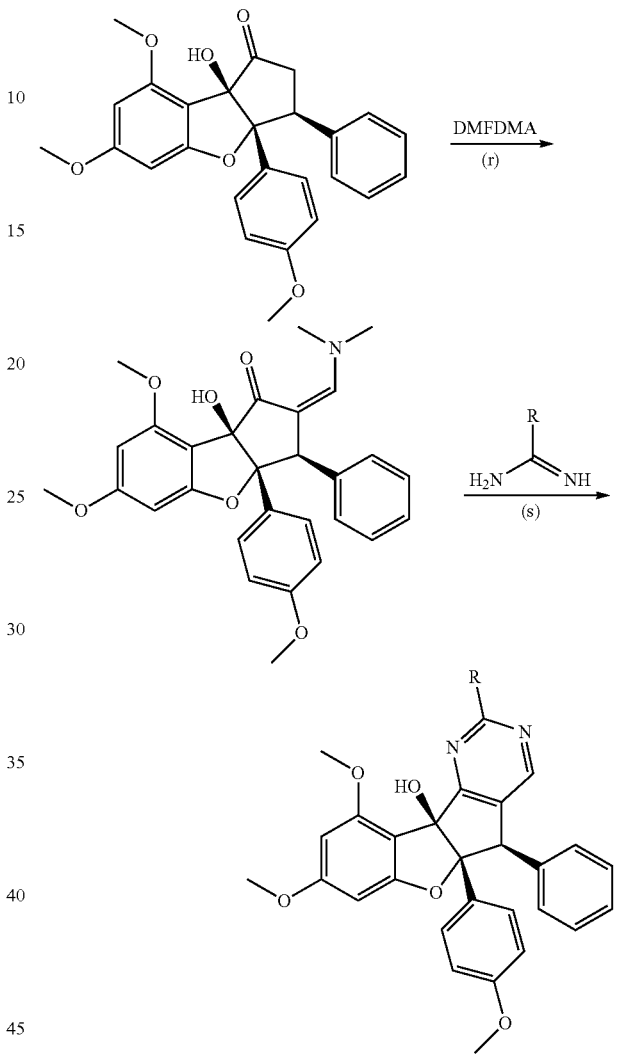

(r) Procedure for forming the enamine: rac-(3R,3aS,8bS)-8b-hydroxy-6,8-dimethoxy-3a-(4-methoxyphenyl)-3-phenyl-2,3,3a,8b-tetrahydro-1H-cyclopenta[b]benzofuran-1-one (Journal of the American Chemical Society, 2006, 128(24), 7754-7755) and dimethylformamide dimethylacetal (DMFDMA, 5 equiv.) are stirred in DMF (0.5 M) at 60° C. for 5 hours. The DMF is evaporated under vacuum then the residue is taken up then evaporated three times with dichloromethane to lead to a yellow foam (accompanied by a by-product of mass M–H$_2$O).

(s) Procedure for addition of guanidines: In a round-bottom flask, introduce the rac-(3R,3aR,8bR,Z)-2-((dimethylamino)methylene)-8b-hydroxy-6,8-dimethoxy-3a-(4-methoxyphenyl)-3-phenyl-2,3,3a,8b-tetrahydro-1H-cyclopenta[b]benzofuran-1-one obtained previously, potassium carbonate (3 equiv.) and guanidine hydrochloride (2 equiv.) as well as ethanol (0.2 M). Stir magnetically at 60° C. for 18 hours. The precipitate is filtered, then rinsed with water then with ethyl ether; finally, it is dried under vacuum at 40° C. When the product does not precipitate, the solvents are evaporated and the residue is purified on silica gel.

Compound 33 rac-(5aR,10bS)-2-amino-8,10-dimethoxy-5a-(4-methoxyphenyl)-5-phenyl-5a,10b-dihydro-5H-benzofuro[2',3':4,5]cyclopenta[1,2-d]pyrimidin-10b-ol

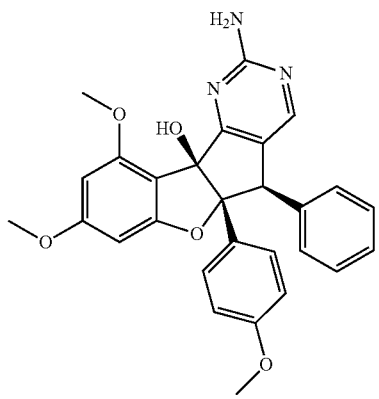 [SMILES: COc1ccc([C@@]23Oc4cc(OC)cc(OC)c4[C@]2(O)c2nc(N)ncc2[C@H]3c2ccccc2)cc1]

White solid, 549 mg (63%); obtained from the compound rac-(3R,3aR,8bR,Z)-2-((dimethylamino)methylene)-8b-hydroxy-6,8-dimethoxy-3a-(4-methoxyphenyl)-3-phenyl-2,3,3a,8b-tetrahydro-1H-cyclopenta[b]benzofuran-1-one by following the procedure for addition of guanidines using guanidine.

$^1$H NMR (DMSO-D$_6$, 400 MHz, δ, ppm): 7.80 (s, 1H), 7.08 (m, 3H), 6.83 (m, 4H), 6.74 (bs, 2H), 6.58 (m, 2H), 6.42 (s, 1H), 6.16 (s, 1H), 5.58 (s, 1H), 4.22 (s, 1H), 3.79 (s, 3H), 3.71 (s, 3H), 3.59 (s, 3H); LCMS (ES+, m/z): 484.18 [M+H]$^+$.

Compound 34 rac-(5aR,10bS)-8,10-dimethoxy-5a-(4-methoxyphenyl)-2-morpholino-5-phenyl-5a,10b-dihydro-5H-benzofuro[2',3':4,5]cyclopenta[1,2-d]pyrimidin-10b-ol

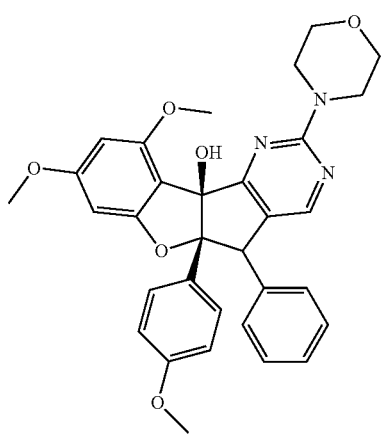 [SMILES: COc1ccc([C@@]23Oc4cc(OC)cc(OC)c4[C@]2(O)c2nc(N4CCOCC4)ncc2C3c2ccccc2)cc1]

Beige solid, 9 mg (15%); obtained from the compound rac-(3R,3aR,8bR,Z)-2-((dimethylamino)methylene)-8b-hydroxy-6,8-dimethoxy-3a-(4-methoxyphenyl)-3-phenyl-2,3,3a,8b-tetrahydro-1H-cyclopenta[b]benzofuran-1-one by following the procedure for addition of guanidines using morpholine-4-carboximidamide.

$^1$H NMR (DMSO-D$_6$, 400 MHz, δ, ppm): 7.97 (s, 1H), 7.08 (m, 3H), 6.88 (m, 2H), 6.82 (d, 2H, J=8.5 Hz), 6.56 (d, 2H, J=8.5 Hz), 6.41 (s, 1H), 6.14 (s, 1H), 5.70 (s, 1H), 4.27 (s, 1H), 3.85 (m, 4H), 3.79 (s, 3H), 3.73 (m, 4H), 3.71 (s, 3H), 3.58 (s, 3H); LCMS (ES+, m/z): 554.07 [M+H]$^+$

Compound 35 rac-N-((5R,5aR,10bS)-10b-hydroxy-8,10-dimethoxy-5a-(4-methoxyphenyl)-5-phenyl-5a,10b-dihydro-5H-benzofuro[2',3':4,5]cyclopenta[1,2-d]pyrimidin-2-yl)cyanamide

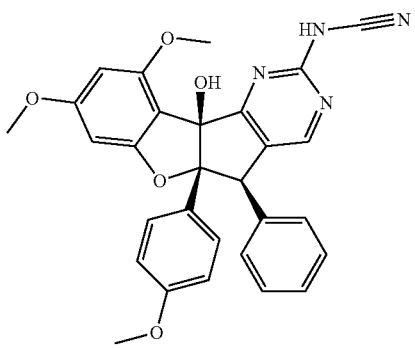 [SMILES: COc1ccc([C@@]23Oc4cc(OC)cc(OC)c4[C@]2(O)c2nc(NC#N)ncc2[C@H]3c2ccccc2)cc1]

White solid, 24 mg (46%); obtained from the compound rac-(3R,3aR,8bR,Z)-2-((dimethylamino)methylene)-8b-hydroxy-6,8-dimethoxy-3a-(4-methoxyphenyl)-3-phenyl-2,3,3a,8b-tetrahydro-1H-cyclopenta[b]benzofuran-1-one by following the procedure for addition of guanidines using cyano-guanidine.

$^1$H NMR (DMSO-D$_6$, 400 MHz, δ, ppm): 7.70 (s, 1H), 7.06 (m, 3H), 6.83 (m, 4H), 6.55 (m, 2H), 6.38 (s, 1H), 6.14 (s, 1H), 5.60 (bs, 1H), 4.20 (s, 1H), 3.79 (s, 3H), 3.72 (s, 3H), 3.58 (s, 3H); LCMS (ES+, m/z): 508.96 [M+H]$^+$

Compound 36 rac-(5aR,10bS)-8,10-dimethoxy-5a-(4-methoxyphenyl)-2-(methylthio)-5-phenyl-5a,10b-dihydro-5H-benzofuro[2',3':4,5]cyclopenta[1,2-d]pyrimidin-10b-ol

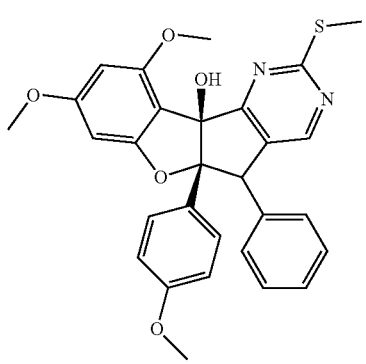

Beige solid, 18 mg (28%): obtained from the compound rac-(3R,3aR,8bR,Z)-2-((dimethylamino)methylene)-8b-hydroxy-6,8-dimethoxy-3a-(4-methoxyphenyl)-3-phenyl-2,3,3a,8b-tetrahydro-1H-cyclopenta[b]benzofuran-1-one by following the procedure for addition of guanidines using methyl carbamimidothioate.

$^1$H NMR (DMSO-D$_6$, 400 MHz, δ, ppm): 8.21 (s, 1H), 7.10 (m, 3H), 6.88 (m, 2H), 6.79 (d, 2H, J=8.5 Hz), 6.58 (d, 2H, J=8.5 Hz), 6.44 (s, 1H), 6.17 (s, 1H), 5.99 (s, 1H), 4.40 (s, 1H), 3.80 (s, 3H), 3.72 (s, 3H), 3.59 (s, 3H), 2.65 (s, 3H); LCMS (ES+, m/z): 514.90 [M+H]$^+$.

Compound 37 rac-(5R,5aR,10bS)-2-amino-4-ethoxy-8,10-dimethoxy-5a-(4-methoxyphenyl)-5-phenyl-5a,10b-dihydro-5H-benzofuro[2',3':4,5]cyclopenta[1,2-d]pyrimidin-10b-ol

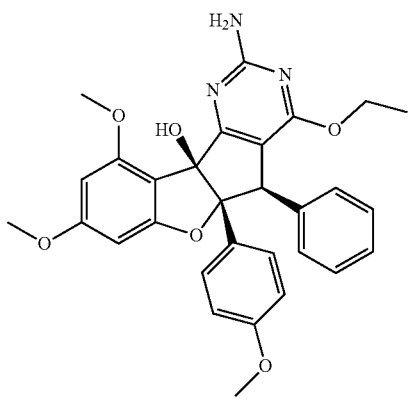 [SMILES: CCOc1nc(N)nc2c1[C@@H](c1ccccc1)[C@]1(c3ccc(OC)cc3)Oc3cc(OC)cc(OC)c3[C@]21O]

Pale yellow solid, 6 mg (7%); obtained from rac-(3R,3aR,8bR)-2-(bis(methylthio)methylene)-6,8-dimethoxy-3a-(4-methoxyphenyl)-3-phenyl-8b ((trimethyl silyl)oxy)-2,3,3a,8b-tetrahydro-1H-cyclopenta[b]benzofuran-1-one (described in the Journal of Organic Chemistry, 1989, 54(1), 77-83) by following the procedure for addition of guanidines using guanidine.

$^1$H NMR (CDCl$_3$, 400 MHz, δ, ppm): 7.02 (m, 5H), 6.82 (m, 2H), 6.55 (m, 2H), 6.26 (d, 1H, J=1.9 Hz), 6.05 (d, 1H, J=1.9 Hz), 5.42 (bs, 2H), 5.49 (s, 1H), 4.26 (qd, 1H, J=7.0 Hz; 10.6 Hz), 4.14 (qd, 1H, J=7.0 Hz; 10.6 Hz), 3.81 (s, 3H), 3.79 (s, 3H), 3.66 (s, 3H), 1.02 (t, 3H, J=7.0 Hz); LCMS (ES+, m/z): 528.24 [M+H]$^+$.

Compound 38

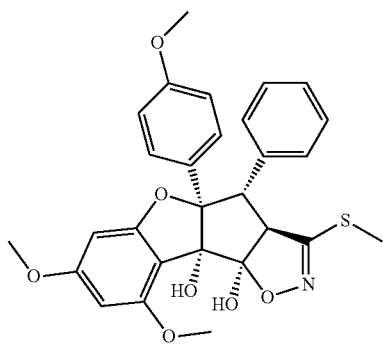

Pale yellow solid, 15 mg (90%); obtained from rac-(3R,3aR,8bR)-2-(bis(methylthio)methylene)-6,8-dimethoxy-3a-(4-methoxyphenyl)-3-phenyl-8b ((trimethylsilyl)oxy)-2,3,3a,8b-tetrahydro-1H-cyclopenta[b]benzofuran-1-one (described in the Journal of Organic Chemistry, 1989, 54(1), 77-83) as follows: In a round-bottom flask, mix hydroxylamine hydrochloride (11.41 mg, 0.164 mmol) and triethylamine (22.83 μL, 0.164 mmol) in ethanol (0.5 mL), stir at 50° C. for 15 min then add rac-(3R,3aR,8bR)-2-(bis(methylthio)methylene)-6,8-dimethoxy-3a-(4-methoxyphenyl)-3-phenyl-8b ((trimethylsilyl)oxy)-2,3,3a,8b-tetrahydro-1H-cyclopenta[b]benzofuran-1-one (20 mg, 0.033 mmol), stir at 65° C. for 24 hours. Add water and ethyl acetate, extract twice with ethyl acetate, wash once with H$_2$O/NaCl, dry over MgSO$_4$, filter then evaporate. The residue is purified on silica gel using as eluent 90:10 CH$_2$Cl$_2$/AcOEt.

$^1$H NMR (DMSO-D$_6$, 400 MHz, S, ppm): 7.09 (d, 2H, J=8.7 Hz), 7.05 (m, 3H), 6.80 (m, 2H), 6.66 (d, 2H, J=8.7 Hz), 6.17 (d, 1H, J=1.9 Hz), 6.08 (d, 1H, J=1.9 Hz), 5.26 (s, 1H), 3.85 (s, 3H), 3.82 (d, 1H, J=13.5 Hz), 3.76 (s, 3H), 3.66 (s, 3H), 3.37 (d, 1H, J=13.5 Hz), 2.35 (s, 1H), 2.24 (s, 3H); LCMS (ES+, m/z): 504.0 [M−OH]$^+$; LCMS (ES−, m/z): 520.0 [M−H]$^−$ Compound 39 rac-(4R,4aR,9bS)-7,9-dimethoxy-4a-(4-methoxyphenyl)-3-(methylthio)-4-phenyl-1,4,4a,9b-tetrahydrobenzofuro[2',3':4,5]cyclopenta[1,2-c]pyrazol-9b-ol

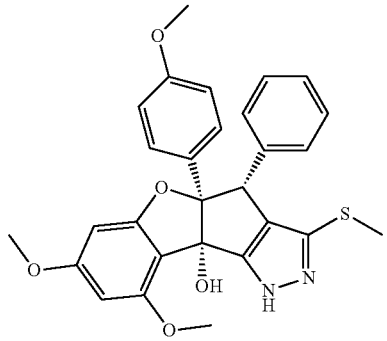

Pale yellow solid, 8.8 mg (53%); obtained from rac-(3R,3aR,8bR)-2-(bis(methylthio)methylene)-6,8-dimethoxy-3a-(4-methoxyphenyl)-3-phenyl-8b ((trimethylsilyl)oxy)-2,3,3a,8b-tetrahydro-1H-cyclopenta[b]benzofuran-1-one (described in the Journal of Organic Chemistry, 1989, 54(1), 77-83) as follows: In a round-bottom flask, mix rac-(3R,3aR,8bR)-2-(bis(methylthio)methylene)-6,8-dimethoxy-3a-(4-methoxyphenyl)-3-phenyl-8b ((trimethylsilyl)oxy)-2,3,3a,8b-tetrahydro-1H-cyclopenta[b]benzofuran-1-one (20 mg, 0.033 mmol) in ethanol (0.5 mL) then add hydrazine monohydrate (17 μL, 0.164 mmol), heat to 50° C. for 24 hours. Add water and ethyl acetate, extract twice with ethyl acetate, wash once with H$_2$O/NaCl, dry over MgSO$_4$, filter then evaporate. The residue is purified on silica gel using as eluent 40:60 then 20:80 cyclohexane/AcOEt.

$^1$H NMR (CDCl$_3$, 400 MHz, δ, ppm): 7.01 (m, 7H), 6.50 (d, 2H, J=8.9 Hz), 6.22 (d, 1H, J=1.9 Hz), 5.99 (d, 1H, J=1.9 Hz), 4.49 (s, 1H), 3.75 (s, 3H), 3.69 (s, 3H), 3.58 (s, 3H), 2.27 (s, 3H); LCMS (ES+, m/z): 500.9 [M+H]$^+$; LCMS (ES−, m/z): 502.9 [M−H]$^−$.

The compounds according to the invention can be synthesized according to the following reaction diagram:

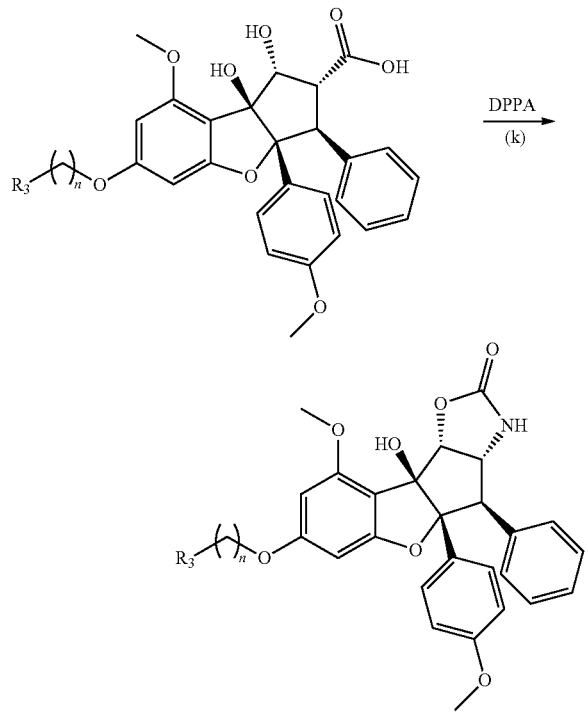

(k) Curtius rearrangement procedure: Described previously for the example with R₃=H and n=1.

Compound 40 rac-(3aR,4R,4aR,9bS,9cR)-9b-hydroxy-7,9-dimethoxy-4a-(4-methoxyphenyl)-4-phenyl-3,3a,4,4a,9b,9c-hexahydro-2H-benzofuro[3',2':3,4]cyclopenta[1,2-d]oxazol-2-one

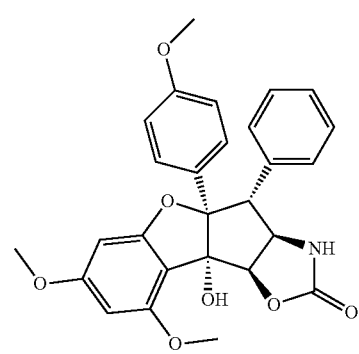 [SMILES: COc1ccc([C@@]23Oc4cc(OC)cc(OC)c4[C@]2(O)[C@@H]2OC(=O)N[C@@H]2[C@H]3c2ccccc2)cc1]

White solid, 93 mg (47%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carboxylic acid by following the Curtius rearrangement procedure.

¹H NMR (DMSO-D₆, 400 MHz, δ, ppm): 8.15 (s, 1H), 7.11 (m, 3H), 7.01 (d, 2H, J=8.5 Hz), 6.9 (m, 2H), 6.70 (d, 2H, J=8.5 Hz), 6.34 (d, 1H, J=1.8 Hz), 6.22 (d, 1H, J=1.8 Hz), 5.37 (s, 1H), 5.32 (d, 1H, J=8.7 Hz), 4.79 (dd, 1H, J=8.7 Hz; 10.5 Hz), 3.79 (s, 6H), 3.66 (s, 3H), 3.36 (d, 1H, J=10.5 Hz); LCMS (ES+, m/z): 457.88 [M-OH]⁺; LCMS (ES-, m/z): 473.92 [M-H]⁻, 519.92 [M+HCOO⁻]⁻.

Compound 41 rac-(3aR,4R,4aR,9bS,9cR)-7-((4,5-dihydroxypentyl)oxy)-9b-hydroxy-9-methoxy-4a-(4-methoxyphenyl)-4-phenyl-3,3a,4,4a,9b,9c-hexahydro-2H-benzofuro[3',2':3,4]cyclopenta[1,2-d]oxazol-2-one

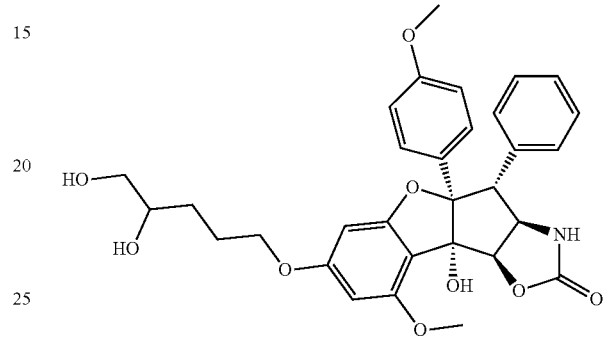

White solid, 41 mg (77%): obtained from rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol with pent-4-en-1-ol, for saponification, for Curtius rearrangement, then for dihydroxylation.

¹H NMR (CDCl₃, 400 MHz, δ, ppm): 7.14 (m, 3H), 7.05 (m, 2H), 6.86 (m, 2H), 6.74 (m, 2H), 6.21 (d, 1H, J=1.9 Hz), 6.115 (m, 1H, J=1.9 Hz), 5.56 (d, 1H, J=8.1 Hz), 5.04 (s, 1H), 4.66 (dd, 1H, J=8.2 Hz, 10.8 Hz), 4.03 (m, 2H), 3.91 (s, 3H), 3.80 (m, 1H), 3.74 (s, 3H), 3.70 (dd, 1H, J=3.1 Hz, 10.8 Hz), 3.63 (d, 1H, J=10.8 Hz), 3.49 (dd, 1H, J=7.5 Hz, 10.8 Hz), 1.92 (m, 2H), 1.66 (m, 2H); LCMS (ES+, m/z): 563.99 [M+H]⁺.

Compound 42 rac-(3aR,4R,4aR,9bS,9cR)-9b-hydroxy-7-(4-hydroxybutoxy)-9-methoxy-4a-(4-methoxyphenyl)-4-phenyl-3,3a,4,4a,9b,9c-hexahydro-2H-benzofuro[3',2':3,4]cyclopenta[1,2-d]oxazol-2-one

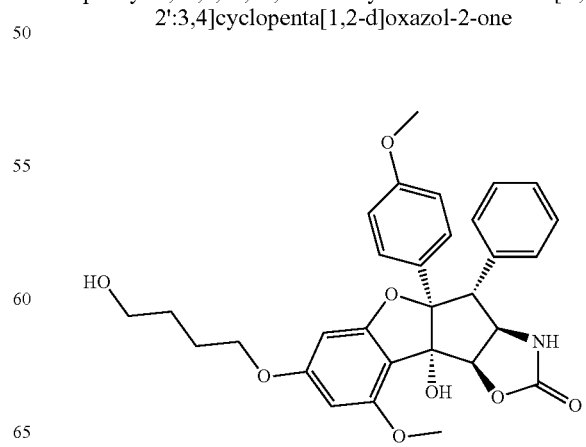

White solid, 249 mg (98%): obtained from compound 41 by following the oxidative cleavage procedure followed by the aldehyde reduction procedure.

$^1$H NMR (CDCl$_3$, 400 MHz, δ, ppm): 7.14 (m, 3H), 7.05 (m, 2H), 6.86 (m, 2H), 6.74 (m, 2H), 6.21 (d, 1H, J=1.9 Hz), 6.15 (d, 1H, J=1.9 Hz), 5.56 (d, 1H, J=8.2 Hz), 5.05 (s, 1H), 4.65 (dd, 1H, J=8.3 Hz, 10.8 Hz), 4.03 (t, 1H, J=6.3 Hz), 3.91 (s, 3H), 3.74 (t, 1H, J=6.3 Hz), 3.73 (s, 3H), 3.63 (d, 1H, J=10.8 Hz), 1.91 (m, 2H), 1.77 (m, 2H); LCMS (ES+, m/z): 534.00 [M+H]$^+$.

Compound 43 rac-(3aR,4R,4aR,9bS,9cR)-7-(4-azidobutoxy)-9b-hydroxy-9-methoxy-4a-(4-methoxyphenyl)-4-phenyl-3,3a,4,4a,9b,9c-hexahydro-2H-benzofuro[3',2':3,4]cyclopenta[1,2-d]oxazol-2-one

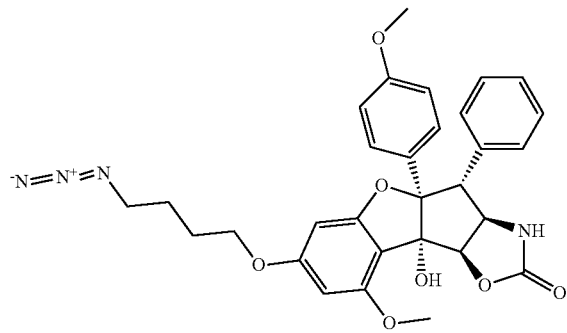

Beige solid, 104 mg (39%); obtained from compound 42 by following the procedure for synthesizing the azide from the alcohol.

$^1$H NMR (CDCl$_3$, 400 MHz, δ, ppm): 7.14 (m, 3H), 7.05 (m, 2H), 7.86 (m, 2H), 6.74 (m, 2H), 6, 20 (d, 1H, J=1.9 Hz), 6.15 (d, 1H, J=1.9 Hz), 5.56 (d, 1H, J=8.3 Hz), 5.00 (s, 1H), 4.66 (dd, 1H, J=8.3 Hz, 10.8 Hz), 4.02 (m, 2H), 3.91 (s, 3H), 3.74 (s, 3H), 3.65 (m, 2H), 3.40 (t, 1H, J=6.7 Hz), 2.01 (m, 2H), 1.90 (m, 2H), 1.82 (m, 2H); LCMS (ES−, m/z): 556.84 [M−H]$^-$.

Compound 44 rac-(3aR,4R,4aR,9bS,9cR)-7-(4-aminobutoxy)-9b-hydroxy-9-methoxy-4a-(4-methoxyphenyl)-4-phenyl-3,3a,4,4a,9b,9c-hexahydro-2H-benzofuro[3',2':3,4]cyclopenta[1,2-d]oxazol-2-one

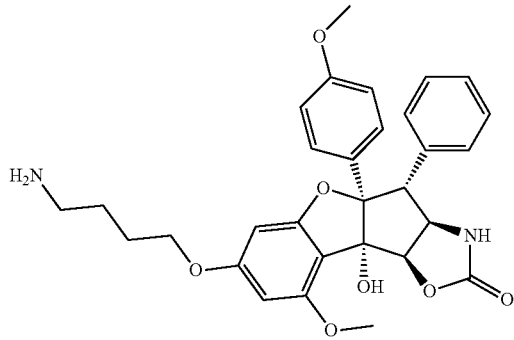 [SMILES: COc1ccc([C@@]23Oc4cc(OCCCCN)cc(OC)c4[C@]2(O)[C@@H]2OC(=O)N[C@@H]2[C@H]3c2ccccc2)cc1]

Beige solid, 26 mg (54%); obtained from compound 43 by following the azide reduction procedure.

$^1$H NMR (DMSO-D$_6$, 400 MHz, δ, ppm): 8.15 (s, 1H), 7.51 (bs, 1H), 7.11 (m, 3H), 7.00 (m, 2H), 6.94 (m, 2H), 6.69 (m, 2H), 6.33 (d, 1H, J=1.9 Hz), 6.18 (d, 1H, J=1.9 Hz), 5.36 (s, 1H), 5.32 (d, 1H, J=8.4 Hz), 4.78 (dd, 1H, J=8.4 Hz, 10.4 Hz), 4.03 (t, 1H, J=6.4 Hz), 3.79 (s, 3H), 3.66 (s, 3H), 3.33 (m, 1H), 2.85 (t, 1H, J=7.3 Hz), 1.78 (m, 2H), 1.71 (m, 2H); LCMS (ES+, m/z): 533.01 [M+H]$^+$.

Compound 45 rac-(3aR,4R,4aR,9bS,9cR)-7-(2-aminoethoxy)-9b-hydroxy-9-methoxy-4a-(4-methoxyphenyl)-4-phenyl-3,3a,4,4a,9b,9c-hexahydro-2H-benzofuro[3',2':3,4]cyclopenta[1,2-d]oxazol-2-one

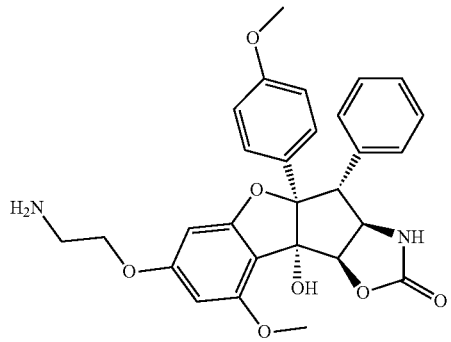 [SMILES: COc1ccc([C@@]23Oc4cc(OCCN)cc(OC)c4[C@]2(O)[C@@H]2OC(=O)N[C@@H]2[C@H]3c2ccccc2)cc1]

White solid, 332 mg (63%); obtained from the compound rac-methyl (1R,2R,3S,3aR,8bS)-1,6,8b-trihydroxy-8-methoxy-3a-(4-methoxyphenyl)-3-phenyl-2,3,3a,8b-tetrahydro-1H-cyclopenta[b]benzofuran-2-carboxylate by following the procedures for substitution of the phenol, saponification and Curtius rearrangement. Finally, the procedures for dihydroxylation, oxidative cleavage, reduction of the alcohol, transformation to azide then azide reduction led to the desired product.

$^1$H NMR (DMSO-D$_6$, 400 MHz, δ, ppm): 8.14 (s, 1H), 7.11 (m, 3H), 7.00 (m, 2H), 6.94 (m, 2H), 6.69 (m, 2H), 6.32 (d, 1H, J=1.9 Hz), 6.21 (d, 1H, J=1.9 Hz), 5.37 (bs, 1H), 5.32 (d, 1H, J=8.6 Hz), 4.78 (dd, 1H, J=8.6 Hz, 10.8 Hz), 3.96 (t, 2H, J=5.6 Hz), 3.78 (s, 3H), 3.65 (s, 3H), 3.35 (d, 1H, J=10.8 Hz), 2.88 (t, 2H, J=5.6 Hz), 1.90 (bs, 2H); LCMS (ES+, m/z): 504.94 [M+H]$^+$.

Compound 46 rac-(3aR,4R,4aR,9bS,9cR)-9b-hydroxy-7,9-dimethoxy-4a-(4-methoxyphenyl)-4-phenyl-3,3a,4,4a,9b,9c-hexahydro-2H-benzofuro[3',2':3,4]cyclopenta[1,2-d]oxazole-2-thione

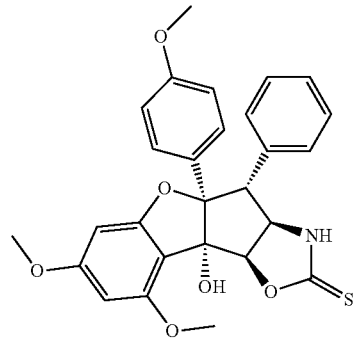 [SMILES: COc1ccc([C@@]23Oc4cc(OC)cc(OC)c4[C@]2(O)[C@@H]2OC(=S)N[C@@H]2[C@H]3c2ccccc2)cc1]

Pale yellow solid, 54 mg (33%); obtained from compound 9 as follows: In a flask, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (150 mg, 0.334 mmol) in 1 M sodium carbonate solution (667 μL, 0.667 mmol), add CS$_2$ (30.2 μL, 0.501 mmol) and heat to 110° C. for 15 minutes. Allow to return to room temperature. A precipitate forms; filter and dry. The product is obtained in the form of a pale yellow solid.

$^1$H NMR (DMSO-D$_6$, 400 MHz, δ, ppm): 10.45 (bs, 1H), 7.12 (m, 3H), 7.99 (m, 4H), 6.69 (m, 2H), 6.35 (d, 1H, J=1.9 Hz), 6.25 (d, 1H, J=1.9 Hz), 5.64 (m, 1H), 5.50 (s, 1H), 5.04 (m, 1H), 3.83 (s, 3H), 3.79 (s, 3H), 3.65 (s, 3H), 3.39 (d, 1H, J=10.9 Hz);

LCMS (ES+, m/z): 491.88 [M+H]$^+$

Compound 47 rac-(3aR,4R,4aR,9bS,9cR)-2-amino-7,9-dimethoxy-4a-(4-methoxyphenyl)-4-phenyl-4,4a,9b,9c-tetrahydro-3aH-benzofuro[3',2':3,4]cyclopenta[1,2-d]oxazol-9b-ol

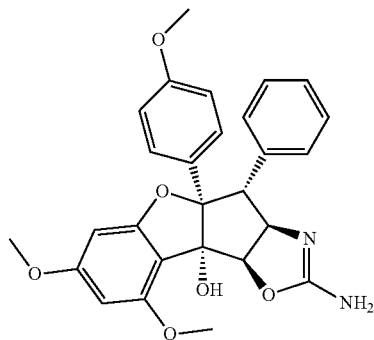 [SMILES: COc1ccc([C@@]23Oc4cc(OC)cc(OC)c4[C@]2(O)[C@@H]2OC(N)=N[C@@H]2[C@H]3c2ccccc2)cc1]

White solid, 12 mg (35%); obtained from compound 9 as follows: In a pill machine and under nitrogen, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (34 mg, 0.076 mmol) in 1.0 mL of ethanol; add, at room temperature, cyanogen bromide (30.3 μL, 0.091 mmol) then stir for 18 hours. Concentrate the reaction mixture then add saturated NaHCO$_3$ solution. A solid remains suspended. Filter it and rinse it with water then dry under vacuum. The product is purified on silica using as eluent a 95:5 DCM/MeOH mixture.

$^1$H NMR (DMSO-D$_6$, 400 MHz, δ, ppm): 7.05 (m, 7H), 6.69 (m, 2H), 6.29 (s, 1H), 6.18 (s, 1H), 5.72 (s, 1H), 5.13 (d, 2H, J=8.4 Hz), 4.75 (t, 1H, J=10.4 Hz), 3.80 (s, 3H), 3.77 (s, 3H), 3.65 (s, 3H); LCMS (ES+, m/z): 475.01 [M+H]$^+$.

Compound 48 rac-(4aR,5R,5aR,10bS,10cR)-10b-hydroxy-8,10-dimethoxy-5a-(4-methoxyphenyl)-5-phenyl-4,4a,5,5a,10b,10c-hexahydrobenzofuro[2',3':4,5]cyclopenta[1,2-b][1,4]oxazin-3(2H)-one

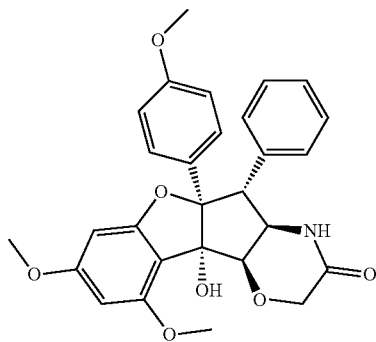 [SMILES: COc1ccc([C@@]23Oc4cc(OC)cc(OC)c4[C@]2(O)[C@@H]2OCC(=O)N[C@@H]2[C@H]3c2ccccc2)cc1]

White solid, 1.7 mg (2%); obtained from compound 9 as follows: In a flask, introduce rac-(1R,2R,3R,3aR,8bS)-2-amino-6,8-dimethoxy-3a-(4-methoxyphenyl)-3-phenyl-2,3,3a,8b-tetrahydro-1H-cyclopenta[b]benzofuran-1,8b-diol (69 mg, 0.154 mmol) dissolved in THF (2.5 mL). Cool to 0° C. and add 60% NaH in oil (6.45 mg, 0.161 mmol) then methyl 2-chloroacetate (18.32 mg, 0.169 mmol). Stir at 0° C. for 3 hours then at 30° C. for 3 hours. Hydrolyze with saturated NaHCO$_3$ solution and extract twice with ethyl acetate, combine the organic phases, wash with saturated NH$_4$Cl solution then with saturated NaCl solution. Dry the organic phase over Na$_2$SO$_4$ and concentrate. The residue is purified on silica gel using as eluent a 99:1 DCM/MeOH mixture.

LCMS (ES−, m/z): 488.1 [M−H]$^-$.

Compound 49 rac-(6R,6aS,11 bR)-11 b-hydroxy-9,11-dimethoxy-6a-(4-methoxyphenyl)-6-phenyl-3,4,6,6a,11 b,11c-hexahydro-2H-benzofuro[3',2':3,4]cyclopenta[1,2-f][1,4]oxazepin-5(5aH)-one

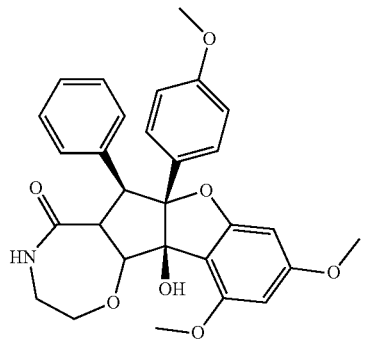 [SMILES: COc1ccc([C@@]23Oc4cc(OC)cc(OC)c4[C@]2(O)C2OCCNC(=O)C2[C@H]3c2ccccc2)cc1]

White foam, 6 mg (15%); obtained from the compound rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carboxylic acid as follows: In a flask, introduce rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carboxylic acid (300 mg, 0.627 mmol) dissolved in DCM (7 mL), add di(1H-imidazol-1-yl)methanone (122 mg, 0.752 mmol, CDI) and stir for 18 hours at room temperature. Add water and decant. Collect the organic phase and dry over $Na_2SO_4$ and concentrate. In a flask, introduce rac-(1R,2R,3S,3aR,8bS)-1,8b-dihydroxy-6,8-dimethoxy-3a-(4-methoxyphenyl)-3-phenyl-2,3,3a,8b-tetrahydro-1H-cyclopenta[b]benzofuran-2-carboxylic 1H-imidazole-1-carboxylic anhydride (100 mg, 0.175 mmol) in THF (2 mL). Add 2-chloroethanamine hydrochloric acid salt (60.8 mg, 0.524 mmol) and DIEA (183 µL, 1.048 mmol) and heat to 50° C. for 6 hours. Filter the precipitate then concentrate the filtrate; the residue is used as such.

In a flask, introduce rac-(1 R,2R,3S,3aR,8bS)—N-(2-chloroethyl)-1,8b-dihydroxy-6,8-dimethoxy-3a-(4-methoxyphenyl)-3-phenyl-2,3,3a,8b-tetrahydro-1H-cyclopenta[b]benzofuran-2-carboxamide (45 mg, 0.083 mmol) in THF (1 mL). Cool to 0° C. and add NaH (4.00 mg, 0.100 mmol). Stir at room temperature for 30 minutes then heat to 50° C. for 2 hours. Add water and extract twice with ethyl acetate, combine the organic phases and dry them over $Na_2SO_4$, concentrate. The residue is purified on silica gel using as eluent a 97.5:2.5 DCM/MeOH mixture.

$^1$H NMR (DMSO-$D_6$, 400 MHz, δ, ppm): 6.99 (m, 5H), 6.88 (d, 2H, J=7.4 Hz), 6.58 (d, 2H, J=9.0 Hz), 6.27 (d, 1H, J=1.9 Hz), 6.10 (d, 1H, J=1.9 Hz), 5.76 (s, 1H), 5.05 (s, 1H), 4.81 (d, 1H, J=4.0 Hz), 4.59 (m, 1H), 4.18 (d, 1H, J=14.0 Hz), 4.06 (m, 2H), 3.80 (m, 1H), 3.78 (s, 3H), 3.73 (s, 3H), 3.59 (s, 3H), 3.55 (m, 2H); LCMS (ES+, m/z): 504.30 $[M+H]^+$.

2—Biological Activity of the Compounds According to the Invention

2.1. Antiproliferative Activity of the Compounds According to the Invention ($IC_{50}$ in M)

Culture of Lines and Measurement of Cell Viability:

The HCT116 line (ATCC, CCL-247) derived from colon cancer was cultured in MEM (Minimum Essential Medium Eagle) supplemented with 2 mM L-glutamine (Sigma, G7513), 5% fetal calf serum (Sigma, F7524) and antibiotics (Sigma, A59-55). The protocol for determining cytotoxic activity consists in seeding cells on 96-well plates (Perkin Elmer, 6005668) at a density of 1500 cells per well. After 24 hours of incubation, the test compound is applied in each well, using serial dilutions in the solvent dimethylsulfoxide (DMSO) (Sigma, D8418), from 10 mM stock solutions in 100% DMSO. Each dilution was added to the cells 24 hours after seeding. Under these conditions, the final solvent concentration is 0.1% DMSO. A reading of cell proliferation was carried out 72 hours after addition of the products with the ATPLite™ kit (Perkin Elmer, 6016947) and according to the manufacturer's recommendations. The analysis of the proliferation results was carried out by comparison with conditions where only the carrier solvent (culture medium, 0.1% DMSO) was added to the cells. The dose-response curves obtained were analyzed using the PRISM 4.03 software (GraphPad Software Inc.), or by an equivalent analytical method, to determine the concentration of each compound which inhibits 50% of cell proliferation ($EC_{50}$).

By way of example, the cytotoxic properties of several compounds of the invention evaluated on the HCT116 line (human colon cancer cell line) are reported in Table 1.

TABLE 1

$EC_{50}$ value of compounds according to the invention and silvestrol. The $EC_{50}$ values are expressed in concentration units (mol/L).

| product | HCT116 ($EC_{50}$) |
|---|---|
| silvestrol | 2.46E−09 |
| 47 | 1.10E−09 |
| 50 | 1.22E−09 |
| 42 | 2.16E−09 |
| 40 | 2.52E−09 |
| 46 | 2.59E−09 |
| 8 | 2.61E−09 |
| 15 | 3.83E−09 |
| 2 | 4.03E−09 |
| 41 | 4.20E−09 |
| 52 | 4.90E−09 |

2.2. Antitumor Activity of Compounds According to the Invention

Subcutaneous xenografts were established with MDA-MD-231 breast cancer cells (ATCC: HTB-26) in SCID mice (Harlan, U.K.). The animals were treated and cared after in accordance with the *Guide For the Care and Use of Laboratory Animals* (National Research Council, 1996) and with European Directive 86/609/EEC, under the supervision of a staff expert authorized to conduct experimental studies with laboratory animals.

All the experiments were conducted pursuant to French and local regulations (Department of Veterinary Services, Haute-Garonne, Toulouse) according to the directives of an ethics committee, based on the UKCCCR *Guidelines for the Welfare of Animals in Experimental Neoplasia*, as indicated above. The implantation of MDA-MB-231 human tumor fragments is carried subcutaneously in the flanks of SCID mice using a trocar and, for the study of tumor growth, the tumors are allowed to reach a median volume of 70-130 $mm^3$ before starting the studies.

After randomization in the treatment cages, the inhibitors were administered intravenously according to a g1d5×3 treatment scheme (5 injections per week for 3 weeks). The mice were monitored and weighed daily. The tumors were measured with a slide caliper and the tumor volumes ($mm^3$) were estimated using the following formula: volume=0.5 (length×width$^2$). Each experimental group consists of 5 individuals. The efficacy of the treatment was evaluated by analysis of the measurement of the median volume of the treated tumors compared with the median volume of the tumors receiving only carrier (control). The T/C evaluation criterion corresponds to: [(median volume of the treated group, T/median volume of the control group, C)×100]. This T/C ratio is expressed as a percentage. The optimal T/C value corresponds to the ratio which reflects the maximum inhibition of growth obtained during the study. The maximum gains or losses of weight, expressed as a percentage of the initial weight of the animals, as well as the percentage of drug-related deaths (i.e., the percentage of treated animals that died before the assessment) were used to provide an evaluation of the toxicity of the compounds. In accordance with the NCI (National Cancer Institute) criterion, a dose is deemed toxic if it induces weight loss greater than −20% relative to the initial weight of the mouse or if it induces more than 20% deaths (Corbett et al. *J Exp Ther Oncol* 1996, 1:95-108). The results obtained are reported in Table 2.

TABLE 2

Antitumor activity of compounds according to the invention and silvestrol

| | | MDA-MB-231 | | | |
|---|---|---|---|---|---|
| Compound | Treatment scheme | Dose (mg/kg) | Deaths (%) | Opt. T/C (%) | Activity |
| Silvestrol | q1d5 × 3 | 1.4 | 100 | | Toxic |
| | | 1 | 100 | | Toxic |
| | | 0.7 | 40 | 63 | Toxic |
| | | 0.5 | 0 | 83 | No activity |
| | | 0.2 | 0 | 92 | No activity |
| 2 | q1d5 × 3 | 0.2 | 0 | 37 | Active |
| 24 | q1d5 × 3 | 2.8 | 0 | 25 | Active |
| 30 | q1d5 × 3 | 0.7 | 0 | 15 | Active |
| 46 | q1d5 × 3 | 1.4 | 0 | 39 | Active |
| 19 | q1d5 × 3 | 1.3 | 0 | 26 | Active |
| 18 | q1d5 × 3 | 3.5 | 0 | 6 | Active |
| | | 2.5 | 0 | 40 | Active |
| 21 | q1d5 × 3 | 1 | 0 | 22 | Active |
| 22 | q1d5 × 3 | 1.4 | 0 | 21 | Active |

Silvestrol is highly toxic above a dose of 0.7 mg/kg. Below this dose, silvestrol has no antitumor activity. In contrast, the compounds according to the invention are active at low doses at which they induce a significant decrease in tumor size. No toxicity was observed during administration of the compounds according to the invention.

The invention claimed is:

1. A method for treating cancer, comprising administering to a person in need of said treatment an effective dose of a compound of the following formula (I):

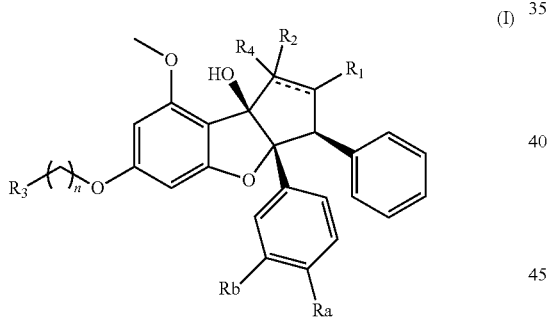

in the form of one of the enantiomers thereof or a mixture of the enantiomers thereof, or a pharmaceutically acceptable salt and/or solvate thereof, wherein:

the solvate is an ethanolate or hydrate,

═══ represents a single bond or a double bond, n represents an integer between 1 and 10, $R_1$ represents $CO_2R_{10}$, $CONH_2$, $NR_{11}R_{12}$, $NR_{13}COR_{14}$, $NR_{15}CONR_{16}R_{17}$, $NR_{18}CSNR_{19}R_{20}$, $NR_{21}SO_2R_{22}$, $NR_{23}CO_2R_{24}$ or an optionally substituted heteroaryl, $R_2$ represents OH, or $R_1$ and $R_2$ together form, with the carbon atoms which bear them, an optionally substituted heterocycle, the optionally substituted heterocycle not being:

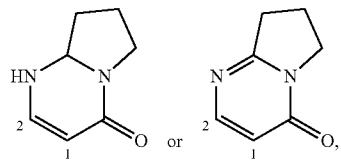

carbon 1 designating the carbon atom bearing the group $R_1$ and carbon 2 designating the carbon atom bearing the group $R_2$, $R_3$ represents H, $OR_{25}$, $CHOHCH_2OH$, $CHO$, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$, $(NR_{32}(CH_2)_wNR_{33}(CH_2)_x)_y(CH_2)_zR_{34}$, $ONR_{84}R_{85}$, optionally substituted aryl or optionally substituted heteroaryl, $R_4$ is absent when ═══ represents a double bond and $R_4$ represents H or OH when ═══ represents a single bond, $R_{10}$ to $R_{30}$, $R_{32}$, $R_{33}$, $R_{38}$ and $R_{39}$ represent, independently of each other, H or a $(C_1-C_6)$alkyl, aryl, aryl-$(C_1-C_6)$alkyl or $(C_1-C_6)$alkylaryl group, said $(C_1-C_6)$alkyl, aryl, aryl-$(C_1-C_6)$alkyl or $(C_1-C_6)$alkylaryl group being optionally substituted by one or more groups selected from $(C_1-C_6)$alkyl, $OR_{35}$ and $NR_{36}R_{37}$, or $R_{11}$ and $R_{12}$, or $R_{16}$ and $R_{17}$, or $R_{19}$ and $R_{20}$, or $R_{26}$ and $R_{27}$, or $R_{29}$ and $R_{30}$, together form, with the nitrogen atom which bears them, an optionally substituted nitrogen-containing heterocycle, $R_{31}$ and $R_{34}$ represent, independently of each other, H, $OR_{35}$, $NR_{36}R_{37}$ or a $(C_1-C_6)$alkyl, aryl, aryl-$(C_1-C_6)$alkyl, $ONR_{86}R_{87}$ or $(C_1-C_6)$alkylaryl group, said group being optionally substituted by one or more groups selected from $(C_1-C_6)$alkyl, $OR_{35}$ and $NR_{36}R_{37}$, $R_{35}$ to $R_{37}$ and $R_{84}$ to $R_{87}$ represent, independently of each other, H or a $(C_1-C_6)$alkyl, aryl or aryl-$(C_1-C_6)$alkyl group, Ra represents a halogen atom, CN or a $(C_1-C_6)$alkoxy group, Rb represents H or a $(C_1-C_6)$alkoxy group, or Ra and Rb together form an —$OCH_2O$— chain, and m, p, r, q, w, x, y, and z represent, independently of each other, an integer between 1 and 4, provided that when $R_1$ represents $CO_2R_{10}$ or $CONH_2$, $R_3$ represents $CHOHCH_2OH$, $CHO$, $N_3$, $NR_{26}R_{27}$, $CO_2R_{28}$, $CONR_{29}R_{30}$, $NR_{38}COR_{39}$, $(O(CH_2)_mO(CH_2)_p)_r(CH_2)_qR_{31}$ or $(NR_{32}(CH_2)_wNR_{33}(CH_2)_x)_y(CH_2)_zR_{34}$.

2. The method according to claim 1, wherein:

$R_1$ is selected from optionally substituted triazoles and oxadiazoles, or $R_1$ and $R_2$ together form, with the carbon atoms which bear them, an optionally substituted heterocycle selected from optionally substituted pyrimidine, pyrazole, pyrazolone, oxazoline, isoxazoline, oxazalanone, oxazalanethione, morpholinone and oxazepane rings, the optionally substituted heterocycle not being:

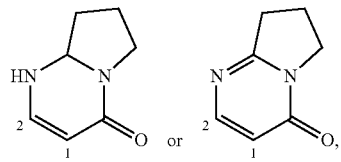 [SMILES: O=C1C=CNC2CCCN12 ; O=c1ccnc2n1CCC2]

carbon 1 designating the carbon atom bearing the group $R_1$ and carbon 2 designating the carbon atom bearing the group $R_2$.

3. The method according to claim 1, wherein n is between 1 and 4.

4. The method according to claim 1, wherein:
=== represents a single bond,
$R_1$ represents $CO_2R_{10}$ or $CONH_2$,
$R_3$ represents $CHOHCH_2OH$, $CHO$, $N_3$, $NR_{26}R_{27}$, $CO_2R_{28}$, $CONR_{29}R_{30}$, $NR_{38}COR_{39}$, $(O(CH_2)_m O(CH_2)_p)_r(CH_2)_qR_{31}$, or $(NR_{32}(CH_2)_wNR_{33}(CH_2)_x)_y (CH_2)_zR_{34}$,
$R_4$ represents H, and
$R_{10}$ represents H or a $(C_1-C_6)$alkyl group.

5. The method according to claim 1, wherein:
=== represents a single bond,
$R_1$ represents $NR_{11}R_{12}$, $NR_{13}COR_{14}$, $NR_{15}CONR_{16}R_{17}$, $NR_{18}CSNR_{19}R_{20}$ or $NR_{21}SO_2R_{22}$, and
$R_4$ represents H.

6. The method according to claim 5, wherein $R_3$ represents H.

7. The method according to claim 1, wherein:
=== represents a single bond,
$R_1$ represents

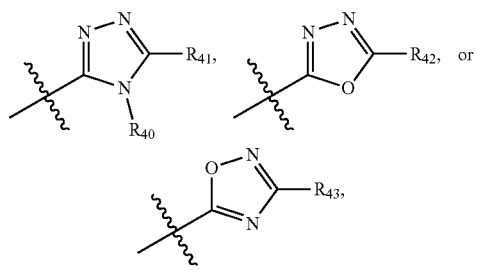

$R_4$ represents H,
$R_{40}$ represents H or a $(C_1-C_6)$alkyl, aryl or aryl-$(C_1-C_6)$alkyl group,
$R_{41}$ to $R_{43}$ represent, independently of each other, H or a $(C_1-C_6)$alkyl, aryl, aryl-$(C_1-C_6)$alkyl, $OR_{44}$, $SR_{45}$ or $NR_{46}R_{47}$ group,
$R_{44}$ to $R_{47}$ represent, independently of each other, H or a $(C_1-C_6)$alkyl, aryl or aryl-$(C_1-C_6)$alkyl group, said group being optionally substituted by one or more groups selected from $(C_1-C_6)$alkyl, $OR_{48}$, $NR_{49}R_{50}$ and polyamines, or
$R_{46}$ and $R_{47}$ together form, with the nitrogen atom which bears them, a nitrogen-containing heterocycle optionally substituted by a $(C_1-C_6)$alkyl group, and
$R_{48}$ to $R_{50}$ represent, independently of each other, H or a $(C_1-C_6)$alkyl, aryl or aryl-$(C_1-C_6)$alkyl group.

8. The method according to claim 1, wherein the moiety

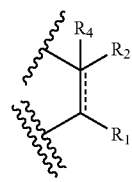

represents:

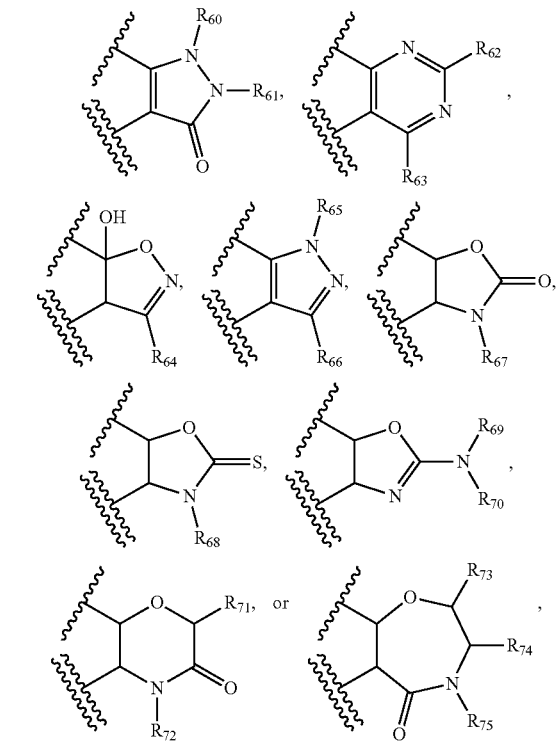

with:

$R_{60}$, $R_{61}$, $R_{65}$, $R_{67}$, $R_{68}$, $R_{72}$ and $R_{75}$ representing, independently of each other, H or a $(C_1-C_6)$alkyl, aryl or aryl-$(C_1-C_6)$alkyl group, $R_{69}$ and $R_{70}$ representing, independently of each other, H or a $(C_1-C_6)$alkyl, aryl or aryl-$(C_1-C_6)$alkyl group, or together forming, with the nitrogen atom which bears them, a nitrogen-containing heterocycle optionally substituted by a $(C_1-C_6)$alkyl group, $R_{62}$, $R_{63}$, $R_{64}$, $R_{66}$, $R_{71}$, $R_{73}$ and $R_{74}$ representing, independently of each other, H or a $(C_1-C_6)$alkyl, aryl, aryl-$(C_1-C_6)$alkyl, $OR_{76}$, $SR_{77}$ or $NR_{78}R_{79}$ group, and $R_{76}$ to $R_{79}$ representing, independently of each other, H or a $(C_1-C_6)$alkyl, aryl, aryl-$(C_1-C_6)$alkyl or CN group, or $R_{78}$ and $R_{79}$ together forming, with the nitrogen atom which bears them, a nitrogen-containing heterocycle optionally substituted by a $(C_1-C_6)$alkyl group.

9. The method according to claim 1, wherein, when === represents a single bond, $R_1$ and $R_2$ are located on the same side of the cyclopentane ring to which they are linked.

10. The method according to claim 9, wherein, when === represents a single bond, $R_1$ and $R_2$ are located on the same side of the cyclopentane ring to which they are linked, and on the side opposite to the OH, phenyl and m-Rb-p-Ra-phenyl groups also linked to this cyclopentane ring.

11. The method according to claim 1, wherein the compound of formula (I) is selected from the following compounds, in the form of one of the enantiomers thereof or a mixture of the enantiomers thereof:

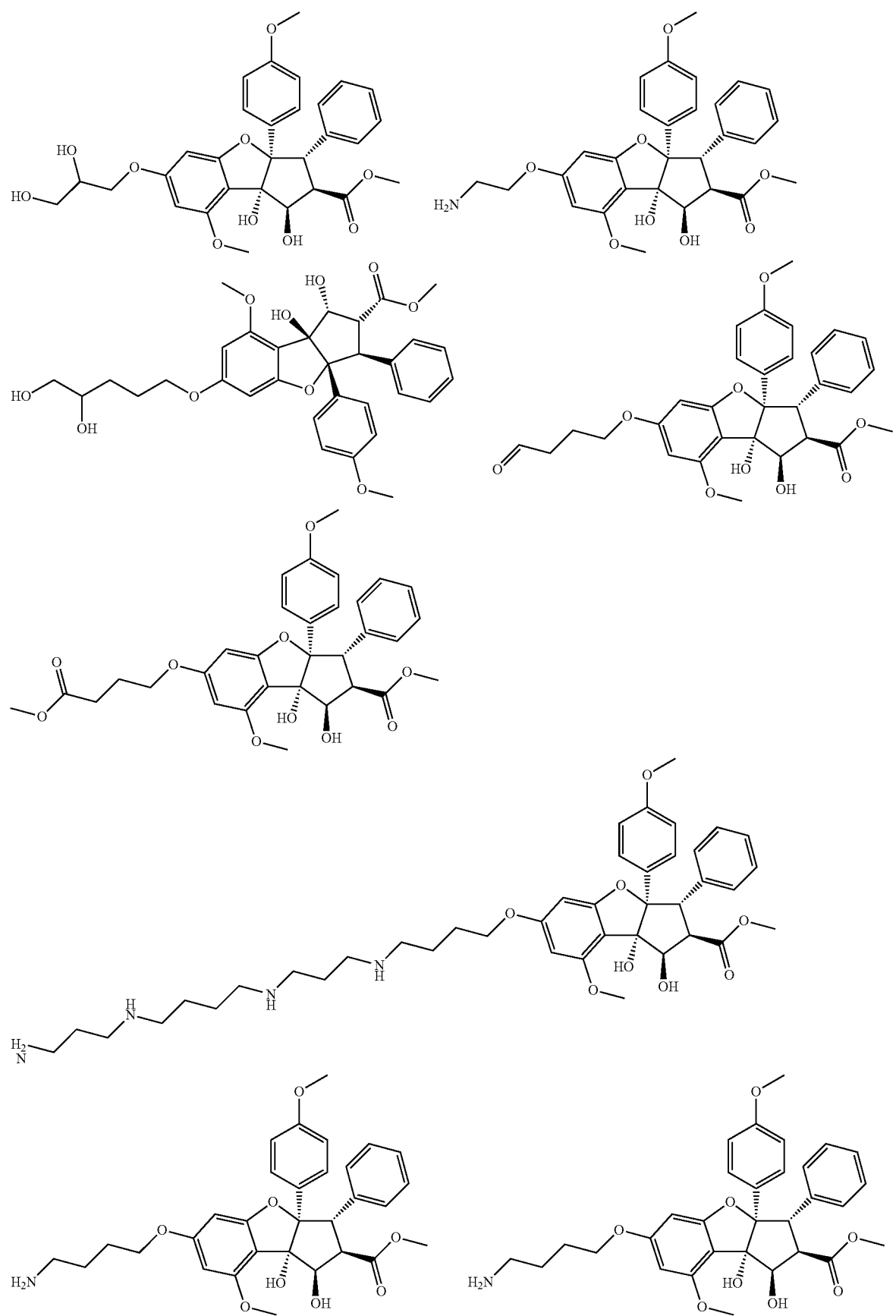

75 76
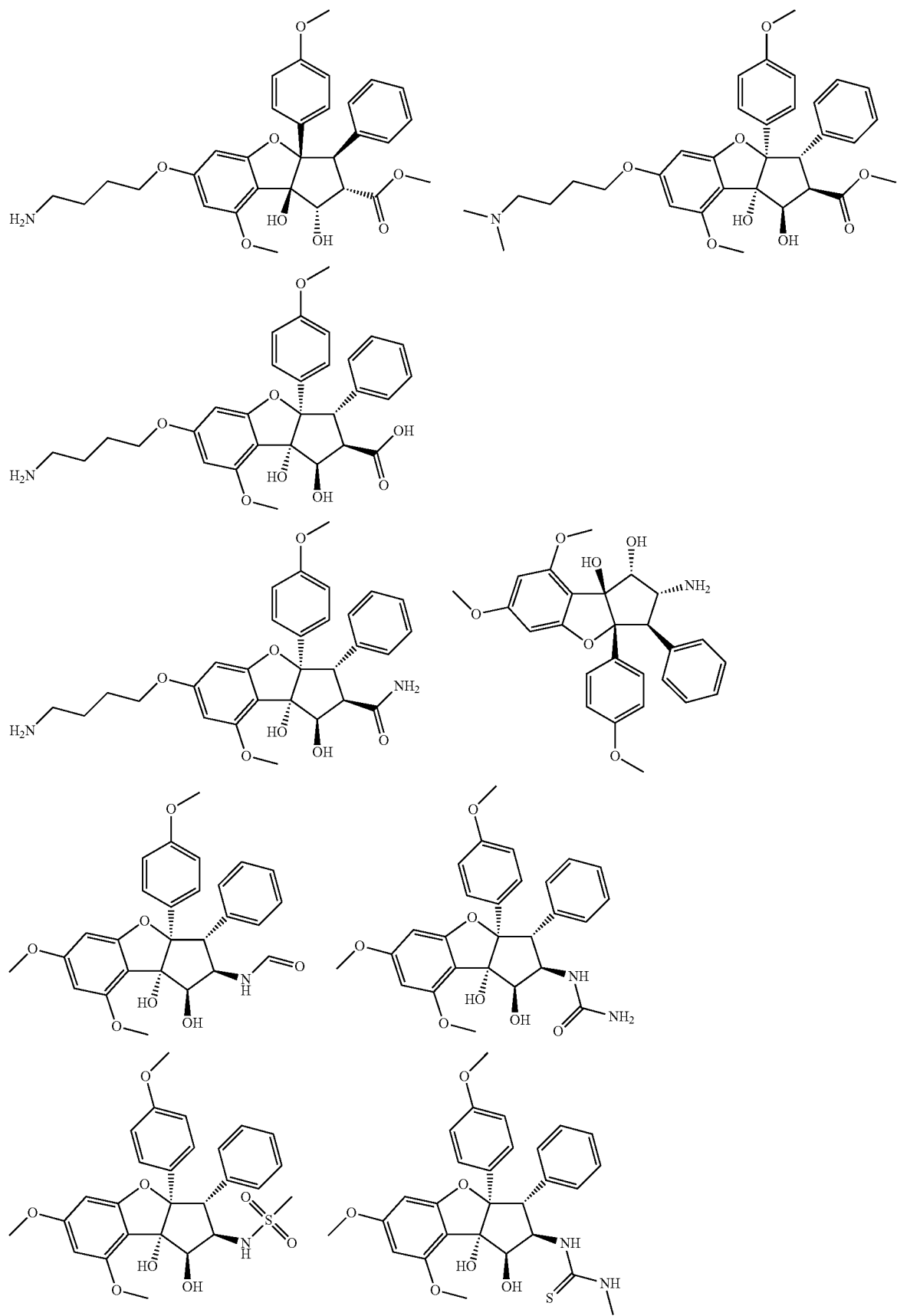

-continued
77
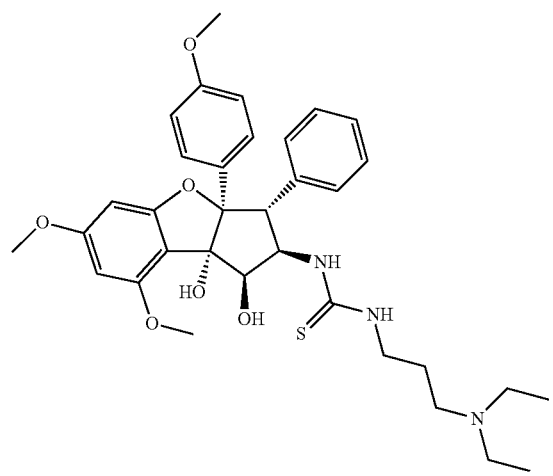
78
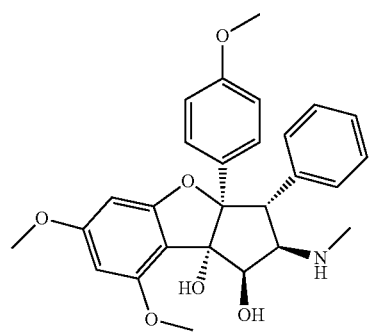
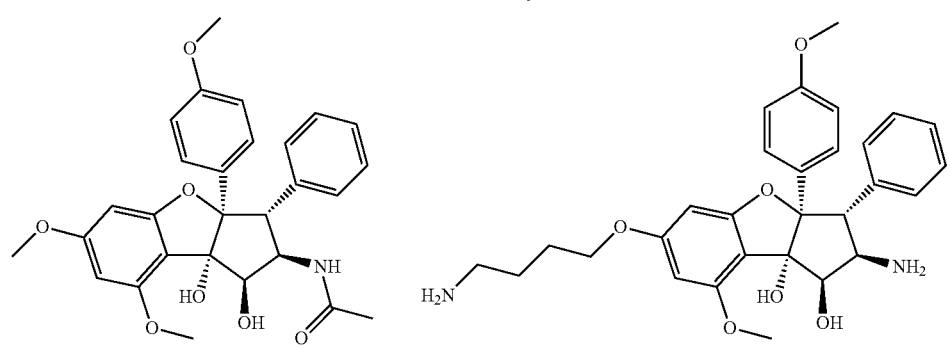
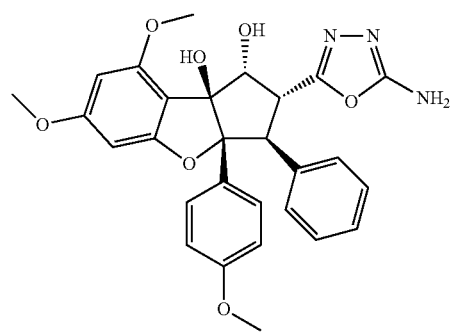
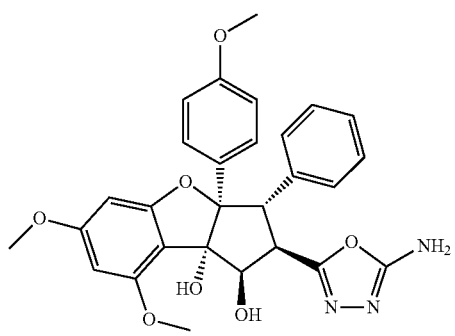
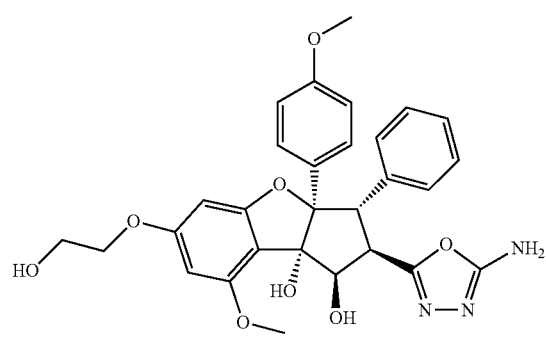
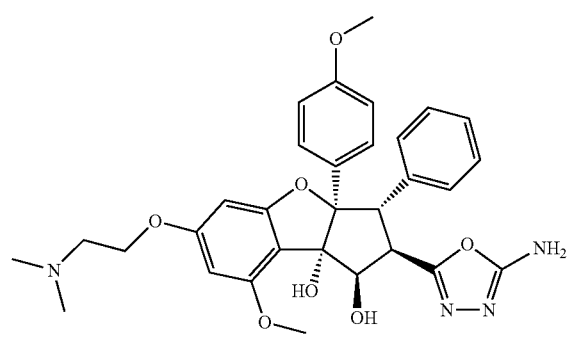

-continued
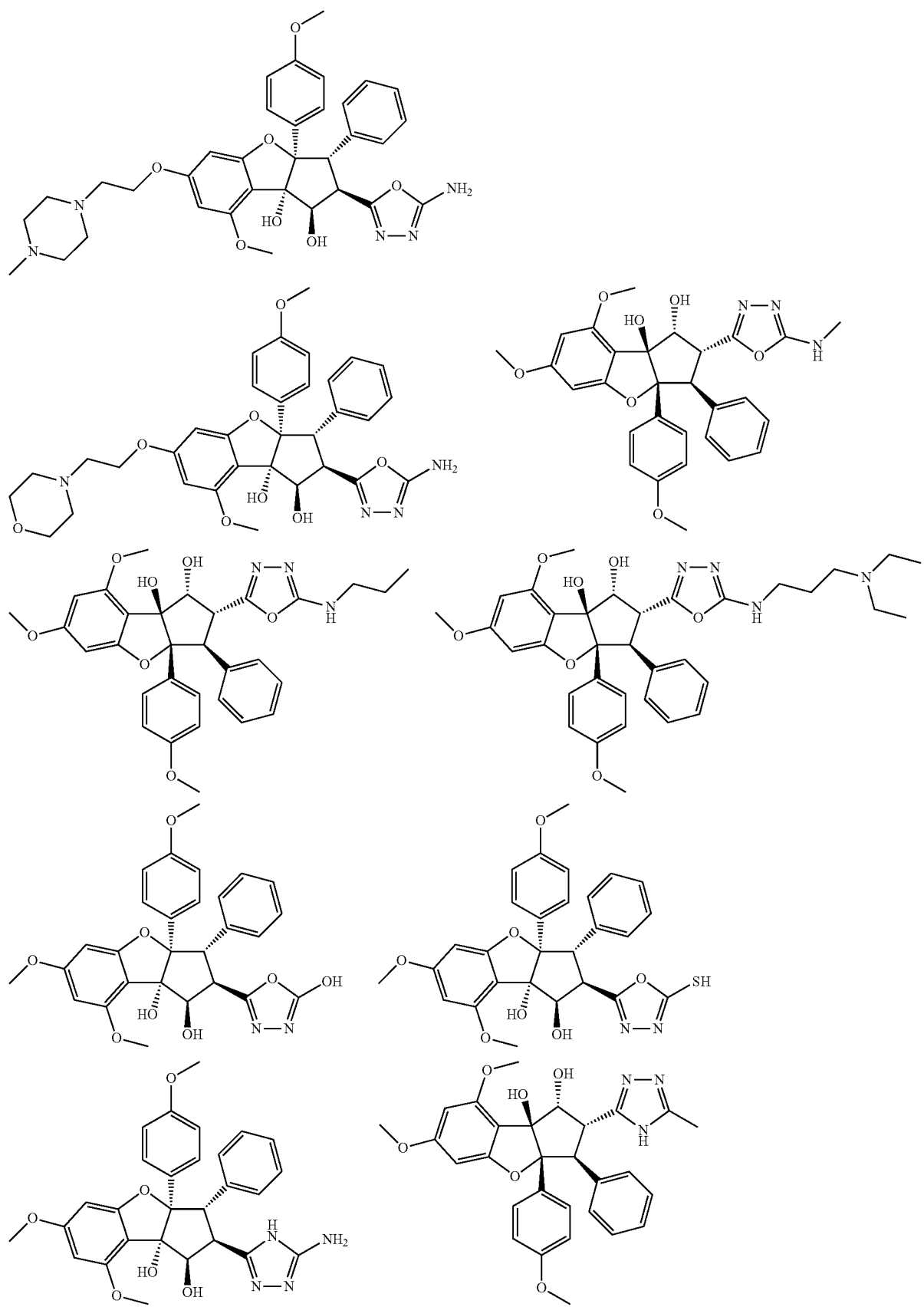

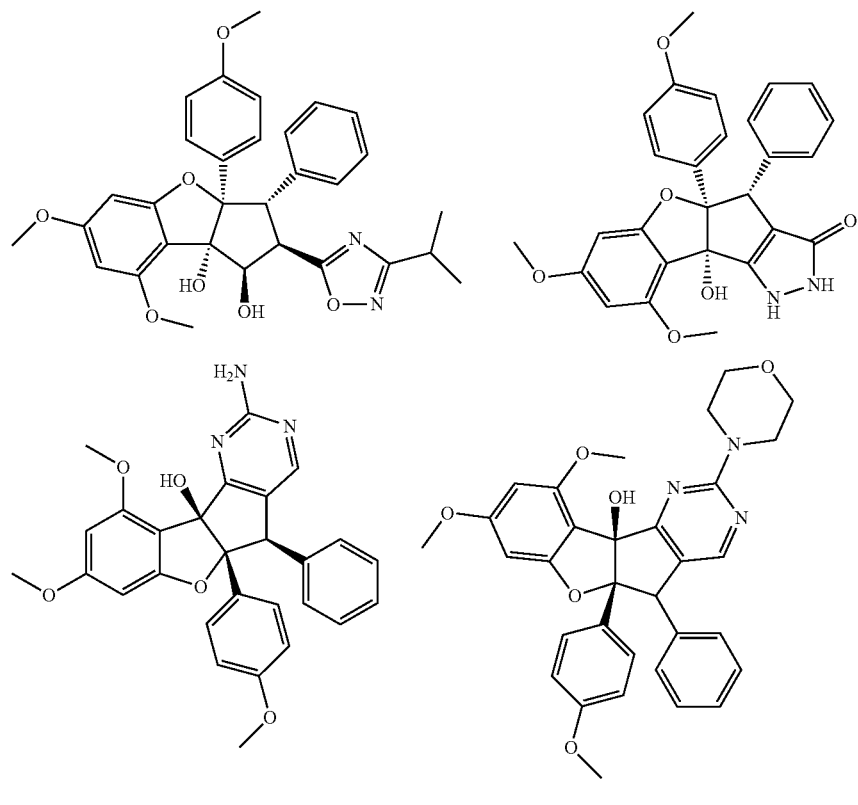
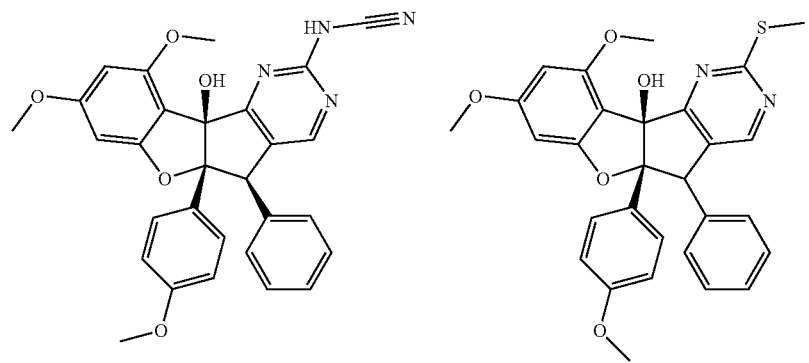
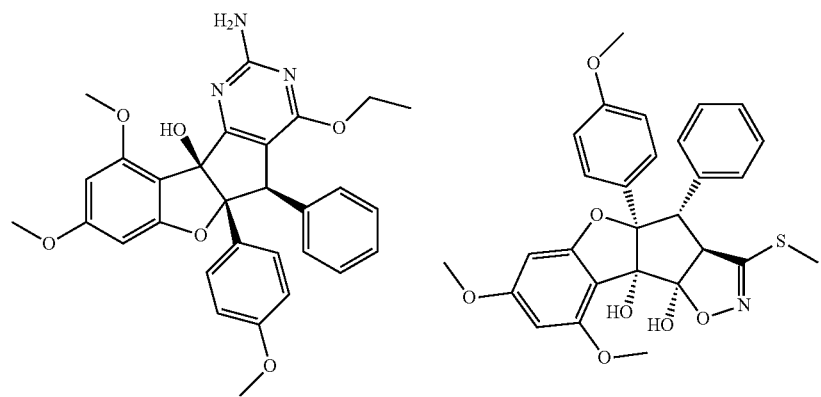

-continued
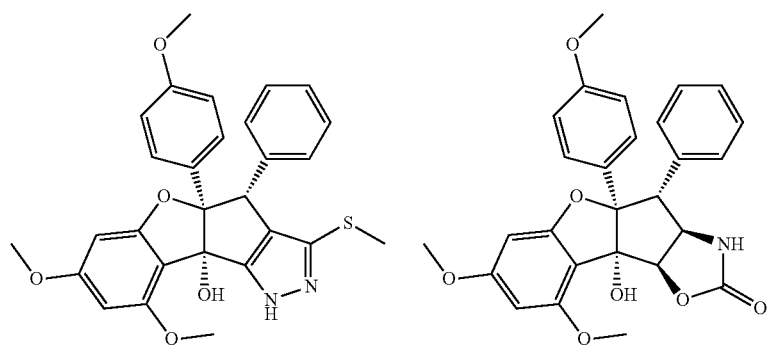
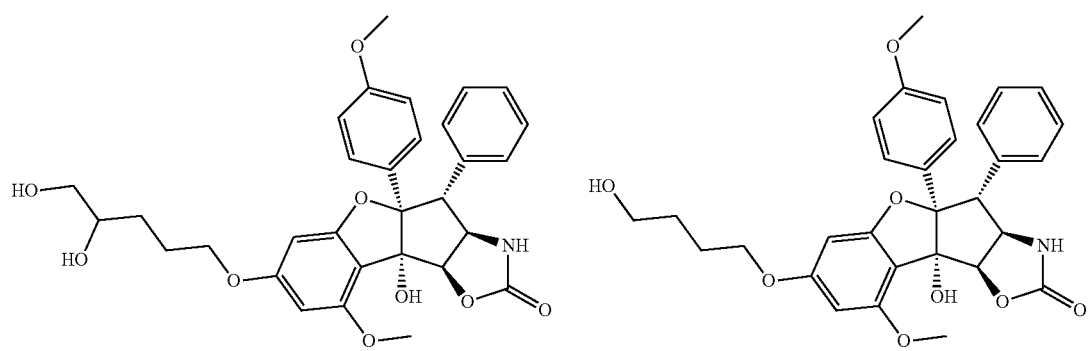
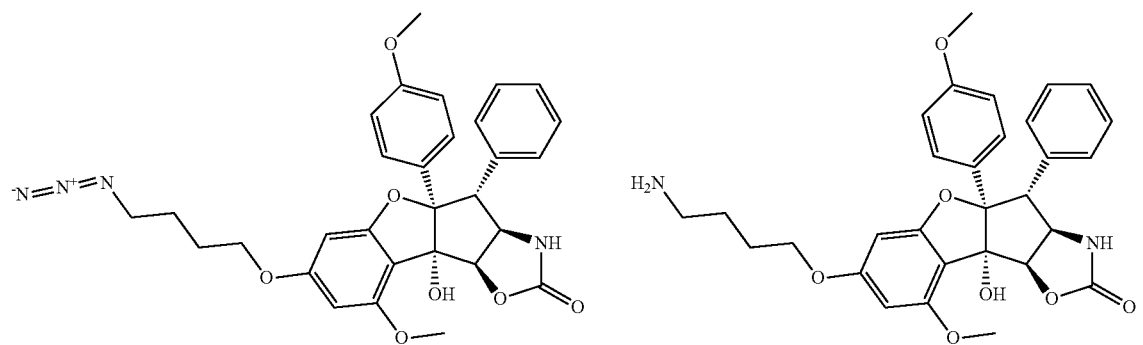
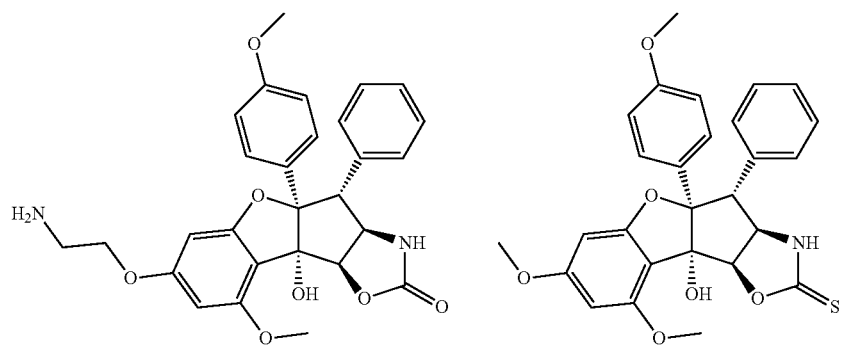

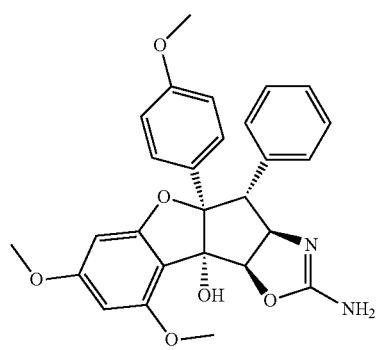
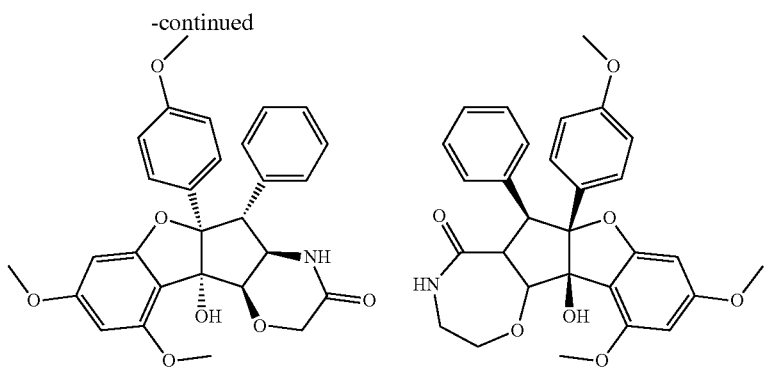
and the pharmaceutically acceptable salts and/or solvates of the above-mentioned compounds.
* * * * *

UNITED STATES PATENT AND TRADEMARK OFFICE
CERTIFICATE OF CORRECTION

PATENT NO. : 10,519,125 B2  
APPLICATION NO. : 15/829630  
DATED : December 31, 2019  
INVENTOR(S) : Frédéric Marion et al.

Page 1 of 1

It is certified that error appears in the above-identified patent and that said Letters Patent is hereby corrected as shown below:

On the Title Page

At item (63), Related U.S. Application Data, Change:  
"Continuation of application No. 15/323,650, filed as application No. PCT/EP2015/065294 on Jul. 6, 2015, now Pat. No. 10,047,064."  
To:  
--Divisional of application No. 15/323,650, filed as application No. PCT/EP2015/065294 on Jul. 6, 2015, now Pat. No. 10,047,064.--

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*